US011060103B2

(12) United States Patent
Van Rie et al.

(10) Patent No.: US 11,060,103 B2
(45) Date of Patent: Jul. 13, 2021

(54) GENES ENCODING INSECTICIDAL PROTEINS

(71) Applicant: BASF AGRICULTURAL SOLUTIONS SEED, US LLC, Research Triangle Park, NC (US)

(72) Inventors: Jeroen Van Rie, Eeklo (BE); Frank Meulewaeter, Merelbeke (BE); Gerben Van Eldik, Zwijnaarde (BE)

(73) Assignee: BASF AGRICULTURAL SOLUTIONS SEED, US LLC, Research Triangle Park, NC (US)

(*) Notice: Subject to any disclaimer, the term of this patent is extended or adjusted under 35 U.S.C. 154(b) by 640 days.

(21) Appl. No.: 15/394,485

(22) Filed: Dec. 29, 2016

(65) Prior Publication Data

US 2017/0107534 A1    Apr. 20, 2017

Related U.S. Application Data

(63) Continuation of application No. 12/293,772, filed as application No. PCT/EP2007/002342 on Mar. 16, 2007, now abandoned.

(60) Provisional application No. 60/784,310, filed on Mar. 21, 2006.

(30) Foreign Application Priority Data

Mar. 21, 2006 (EP) ..................................... 06075679

(51) Int. Cl.
*C12N 15/82* (2006.01)
*C07K 14/325* (2006.01)
*A01N 37/18* (2006.01)
*C12N 9/04* (2006.01)

(52) U.S. Cl.
CPC ......... *C12N 15/8286* (2013.01); *A01N 37/18* (2013.01); *C07K 14/325* (2013.01); *C12N 9/0006* (2013.01); *C12Y 101/0104* (2013.01)

(58) Field of Classification Search
CPC .................................................. C12N 15/8286
See application file for complete search history.

(56) References Cited

U.S. PATENT DOCUMENTS

| | | | |
|---|---|---|---|
| 4,407,956 A | 10/1983 | Howell | |
| 4,536,475 A | 8/1985 | Anderson | |
| 4,684,611 A | 8/1987 | Schilperoort et al. | |
| 5,254,799 A | 10/1993 | De Greve et al. | |
| 5,273,746 A * | 12/1993 | Payne | A01N 63/00 424/93.2 |
| 5,510,471 A | 4/1996 | Lebrun et al. | |
| 5,635,618 A | 6/1997 | Capellades et al. | |
| 6,033,874 A | 3/2000 | Baum et al. | |
| 6,140,553 A | 10/2000 | D'Halluin | |
| 6,204,246 B1 * | 3/2001 | Bosch | A01N 63/02 514/21.2 |
| 6,211,431 B1 | 4/2001 | Boevink et al. | |
| 6,291,156 B1 | 9/2001 | Estruch et al. | |
| 6,855,873 B1 * | 2/2005 | Van Mellaert | C07K 14/325 800/302 |
| 7,049,491 B2 | 5/2006 | Jansens et al. | |
| 7,169,971 B2 * | 1/2007 | Arnaut | C07H 21/04 435/252.3 |
| 7,501,559 B2 | 3/2009 | Van Mellaert et al. | |
| 2003/0167517 A1 | 9/2003 | Arnaut et al. | |
| 2003/0226171 A1 | 12/2003 | Jansens et al. | |
| 2005/0097633 A1 | 5/2005 | Diehn et al. | |
| 2010/0024075 A1 * | 1/2010 | Aroian | C07K 14/325 800/301 |

FOREIGN PATENT DOCUMENTS

| | | |
|---|---|---|
| CN | 1840655 | 10/2006 |
| EP | 0067553 | 5/1982 |
| EP | 0116718 | 12/1983 |
| EP | 0193259 | 9/1986 |
| EP | 0233247 | 8/1987 |
| EP | 0242246 | 10/1987 |
| EP | 0270356 | 6/1988 |
| EP | 0270822 | 6/1988 |
| EP | 0408403 | 6/1988 |
| EP | 1099760 | 5/2001 |
| WO | WO 1984/02913 | 8/1984 |
| WO | WO 85/01856 | 5/1985 |
| WO | WO 1987/00518 | 1/1987 |
| WO | WO 90/08999 | 6/1990 |
| WO | WO 07/107302 | 1/1991 |
| WO | WO 1992/09696 | 6/1992 |
| WO | WO 1996/06932 | 3/1996 |
| WO | WO 1997/48819 | 12/1997 |

(Continued)

OTHER PUBLICATIONS

Schunmann et al, Functional Plant Biology (2003) 30:443-452.*
Pang et al, Plant Physiol. (1996) 112:893-900.*
Rose, Plant J. (2004) 40:744-751.*
Alcantara, et al., (2004) Archives of Insect Biochemistry and Physiology, vol. 55, No. 4, pp. 169-177.
An et al., (1996) Plant Journal, vol. 10, pp. 107-121.
Ballester et al., "Integrative Model of Binding of Bacillus Thuringiensis Toxins in Susceptible and Resistant Larvae of the Diamondback Moth (Plutella Xylostells)" Applied and Environmental Microbiology, vol. 65, No. 4, 141 3-1419, Accepted Jan. 1999.

(Continued)

*Primary Examiner* — Mykola V. Kovalenko
(74) *Attorney, Agent, or Firm* — Arent Fox LLP

(57) ABSTRACT

The present invention relates to novel gene sequences encoding insecticidal proteins produced by *Bacillus thuringiensis* strains. Particularly, new chimeric genes encoding a CryIC, CryIB or CryID protein are provided which are useful to protect plants from insect damage. Also included herein are plant cells or plants comprising such genes and methods of making or using them, as well as plant cells or plants comprising one of such chimeric gene and at least one other such chimeric genes.

12 Claims, No Drawings

Specification includes a Sequence Listing.

(56) References Cited

FOREIGN PATENT DOCUMENTS

| WO | WO 98/15630 | 4/1998 |
| WO | WO 2000/26371 | 5/2000 |
| WO | WO 2000/42207 | 7/2000 |
| WO | WO 2000/71733 | 11/2000 |
| WO | WO 01/02579 | 1/2001 |
| WO | WO 2002/057664 | 7/2002 |

OTHER PUBLICATIONS

Bernhard and Utz (1993), Bacillus Thuringiensis, An Environmental Biopesticide: Theory and Practice, pp. 255-267.
Boevink, et al., (1995) Virology, vol. 207, pp. 354-361.
Bradford et al., (1976) Anal. Biochem., vol. 72, pp. 248-254.
Breitler et al., (2001) Molecular Breeding, vol. 7, pp. 259-274.
Brown and Simpson, (1998) Ann. Rev. Plant Physiol. Plant Mol. Biol., vol. 49, pp. 77-95.
Brown et al., (1996) Plant Mol Biol, vol. 32, pp. 531-535.
Brown, (1986) Nucleic Acids Res., vol. 14, pp. 9549-9559.
Cao et al., "Broccoli Plants with Pyramid Cry1AC and Cry1C Bt genes Control Diamondback Moths Resistant to Cry1A and Cry1C Proteins" Theoretical and Applied Genetics, vol. 105, No. 2-3, 258-264, Accepted May 2001.
Cao, et al. (1999), Molecular Breeding, vol. 5, pp. 131-141.
Cao, et al., (2002) Theoretical and Applied Genetics, vol. 105, No. 2-3, pp. 258-264.
Castle, et al (Current Opinion in Biotechnology 2006, 17:105-112).
Cheng, et al., (1998) Proc Natl Acad Sci USA, vol. 95, pp. 2767-2772.
Christensen, et al., (1992) Plant Mol. Biol., vol. 18, pp. 675-689.
Christou et al., (1990) Trends Biotechnology, vol. 8, pp. 145-151.
Cordero, et al., (1994) The Plant Journal, vol. 6, pp. 141-150.
Cornejo et al., (1993) Plant Mol. Biol., vol. 23, pp. 567-581.
Cornelissen & Vandewiele, (1989) Nucleic Acids Research, vol. 17, pp. 19-29.
Crickmore et al., "Revision of the Nomenclature for the Bacillus Thuringiensis Pesticidal Crystal Proteins," Microbiology Molecular Biology Reviews 62(3), 807-1, 3, Sep. 1998.
De Block, et al., (1989) Plant Physiology, vol. 91, pp. 694-701.
De Greve, et al., (1983) Journal of Mol. Appl. Genetics, vol. 1, No. 6, pp. 499-511.
De Pater, et al. (1992), Plant Journal, vol. 2, pp. 837-844.
Deblaere, et al., (1985) Nucl. Acids Res. vol. 13, pp. 4777-4788.
Dennis, et al., (1984) Nucleic Acids Res., vol. 12, No. 9, pp. 3983-4000.
Depicker, et al., (1982) Journal of Molecular and Applied Genetics, vol. 1, pp. 561-573.
Desmond Mascarenhas et al., "Intron-mediated enhancement of heterologous gene expression in maize," Plant Molecular Biology, 1990, vol. 15, pp. 913-920.
Duan, et al., (1996) Nature Bio-Technology, vol. 14, pp. 494-498.
Dulmage, (1981) Biological Control in Crop Production, pp. 129-141.
Eckes, et al., (1986) Molecular and General Genetics, vol. 205, pp. 14-22.
Estruch, et al., (1996) Proc. Natl. Acad Sci USA, vol. 93, pp. 5389-5394.
Ferre et al., "Resistance to the Bacillus Thuringiensis Bioinsecticide in a Field Population of Piutella Xylostella is due to a Change in a Midgut Membrane Receptor," Proc. Nall. Acad. Sci. USA, vol. 88, 5119-5123, Jun. 1991.
Ffrench-Constant and Bowen, (2000) Cell Mol. Life Sci., vol. 57, pp. 828-833.
Franck, et al., (1980) Cell, vol. 21, pp. 285-294.
Friedberg (Brief. Bioinformatics (2006) 7:225-242).
Fromm, et al., (1990) Bio/Technology, vol. 8, pp. 833-839.
Fujimoto, et al., (1993) Biotechnology, vol. 11, No. 10, pp. 1151-1155.
Gardner, et al., (1981) Nucleic Acids Research, vol. 9, pp. 2871-2888.
Genbank Accession No. X04049, Nov. 14, 2006.
Genbank Accession No. X78988, Apr. 18, 2005.
Ghareyazie, et al., (1997) Molecular Breeding, vol. 3, 401-414.
Gielen, et al., (1984) Embo Journal, vol. 3, 835-846.
Goff, et al., (Science (2002) vol. 296, pp. 96-100).
Gordon-Kamm, et al., (1990) The Plant Cell, vol. 2, pp. 603-618.
Hinchee, et al., (1988) Bio/Technology, vol. 6, pp. 915-922.
Ho, et al., (2006) Crop Science, vol. 46, pp. 781-789 (Abstract).
Hofte, et al., (1988) Appl. And Environm. Microbiol. vol. 54, pp. 2010-2017.
Hull and Howell, (1978) Virology, vol. 86, pp. 482-493.
International Search Report for International Application No. PCT/EP2007/002342 dated Sep. 27, 2007.
Itoh, et al., (1984) Plasmid, vol. 11, pp. 206-220.
Jansens et al., "Transgenic Corn Expressing a Cry9C Insecticidal Protein from Bacillus Thuringiensis Protected from European Corn Borer Damage," Crop Science 37, 1616-1624, Sep. 1997.
Judy Callis et al., "Introns increase gene expression in cultured maize cells," Genes & Development, 1987, vol. 1, pp. 1183-1200.
Kota, et al., (PNAS vol. 96 pp. 1840-1845) 1999).
Last, et al., (1990) Theor. Appl. Genet., vol. 81, pp. 581-588.
Lin et al., "Expression of a Bacillus Thuringiensis Cry1C Gene in Plastid Confers High Insecticidal Efficacy Against Tobacco Cutworm-a Spodoptera Insect," Bot. Bull. Acad. Sin. 44, 199-210, Accepted Apr. 2003.
Liu et al., "Cross-Resistance and Stability of Resistance to Bacillus Thuringienis Toxin Cry1C in Diamondback Moth" Applied and Environmental Microbiolgy, vol. 67, No. 7, 2316-2319, Jul. 2001.
Macdonald, et al., (Nucleic Acid Research (vol. 19) 1994 pp. 5575-5581.
Mahillon et al. (1989), FEMS Microbiol. Letters, vol. 60, pp. 205-210.
Maqbool, et al., (1998) Molecular Breeding, vol. 4, pp. 501-507.
Marshall, et al. (1996) Plant Physiology, vol. 111, pp. 1251-1261.
Mcelroy, et al. (The Plant Cell, vol. 2 163-171, Feb. 1990, pp. 163-170.
Nakamura, et al (Nucl. Acids Res. 2000 28, 292).
Nayak, et al., (1997) Proc. Natl. Acad. Sci. USA, vol. 94, pp. 2111-2116.
Needleman and Wunsch (1970) J. Mol. Biol., vol. 48, pp. 443-453.
Odell, et al. (1985) Nature, vol. 313: pp. 810-812.
Oelmuller, et al. (1993), Mol. Gen. Genet., vol. 237, pp. 261-272.
Pang et al, An improved green fluorescent protein gene as a vital marker in plants, Plant Physiol. (1996) 112:893-900.
Rao, et al. (1998) Plant Journal, vol. 15, No. 4, pp. 469-477.
Rice, et al. (2000) Trends in Genetics, vol. 16, pp. 276-277.
Schunmann et al., A Suite of Novel Promoters and Terminators for Plant Biotechnology, Functional Plant Biology (2003) 30:443-452.
Shcherban, et al. (1995) Proc. Natl. Acad. Sci. USA, vol. 92, pp. 9245-9249.
Stanssens et al. (1989) Nucleic Acids Research, vol. 12, pp. 4441-4454.
Strizhov, et al., (1996) Proc. Natl. Acad. Sci., vol. 93: pp. 15012-15017.
Tang Wei et al., "Development of Insect-Resistant Transgenic Indica Rice with a Synthetic Cry1C Gene," Molecular Breeding, vol. 18, No. 1, Aug. 1-10, 2006.
Tang, et al. (Mol. Breeding 2006, pp. 1-10).
Thompson, et al. (1987) The EMBO Journal, vol. 6, pp. 2519-2523.
Van Den Broeck (Nature, vol. 313, Jan. 1985, pp. 358-363.
Van Der Salm, et al. (1994) Plant Molecular Biology, vol. 26, No. 1, pp. 51-59.
Van Rie, et al. (1990) Science, vol. 247, pp. 72-74.
Velten, et al. (1984) EMSO Journal, vol. 3, pp. 2723-2730.
Velton and Schell (1985) Nucleic Acids Research, vol. 13, pp. 6981-6998.
Verdaguer, et al. (1998) Plant Mol. Biol., vol. 37, pp. 1055-1067.
Waterfield, et al. (2001) Trends Microbial, vol. 9, pp. 185-191.
White, et al. (1989) Trends in Genet., vol. 5, pp. 185-189.
Wong, et al. (1992) Plant Moiec. B.

(56) References Cited

OTHER PUBLICATIONS

Written Opinion for International Application No. PCT/EP2007/002342 dated Sep. 27, 2007.
Wu, et al., (1997) Plant Cell Reports, vol. 17, pp. 129-132.
Wunn, et al., (1996) Biotechnology, vol. 4, No. 2, pp. 171-176.
Yu et al, Cloning and sequence analysis of the cry1Ca6 gene from Bacillus thuringiensis, strain A2-F; Direct submission to EMBL/GenBank/DDBJ Databases; Submitted Dec. 1999, EMBL Accession No. AAF37224.1.
Zhang et al, Direct Sequence Submission to EMBL/GenBank/DDBJ Databases; Submitted Apr. 2001; Identified as Bacillus thurigiensis Cry1Ba protein; EMBL Accession No. AAK63251.1.
Zhang, et al., (1991) The Plant Cell vol. 3, pp. 1155-1165.
Zhao et al., "Transgenic Plants Expressing Two Bacillus Thuringiensis Toxins Delay Insect Resistance Evolution," Nature Biotechnology 21, 1493-1497, Dec. 2003.
Zhao et al., Concurrent Use of Transgenic Plants Expressing a Single and Two Bacillus Thuringiensis Genes Speeds Insect Adaptation to Pyramided Plants, PNAS, vol. 102, No. 24, 8426-8430, Jun. 2005.
Zhao, et al (Journal of Economic Entomology, 94(6): 1547-1552. 2001).
Rose, "The effect of intron location on intron-mediated enhancement of gene expression in *Arabidopsis*," The Plant Journal, 2004, vol. 40, pp. 744-751.
Wong et al., "*Arabidopsis thaliana* small subunit leader and transit peptide enhance the expression of Bacillus thuringiensis proteins in transgenic plants," Plant Mole. Biol. vol. 20, 1992, pp. 81-93.

\* cited by examiner

GENES ENCODING INSECTICIDAL PROTEINS

CROSS REFERENCE TO RELATED APPLICATION

This application is a continuation of U.S. application Ser. No. 12/293,772, filed Sep. 19, 2008, which is a 35 U.S.C. 371 National Phase of PCT Application No. PCT/EP2007/002342, filed Mar. 16, 2007, which claims priority to provisional U.S. Application No. 60/784,310, filed Mar. 21, 2006, and EP06075679.8, filed Mar. 21, 2006. The disclosure of these prior applications are hereby incorporated by reference in their entirety.

INTRODUCTION

The present invention relates to new gene sequences encoding insecticidal proteins produced by *Bacillus thuringiensis* strains. Particularly, new chimeric genes encoding a Cry1C protein are provided which are useful to protect plants from insect damage. Also included herein are plant cells or plants comprising such genes and methods of making or using them, as well as plant cells or plants comprising such cry1C chimeric gene and at least one other gene encoding an insecticidal protein, such as new gene sequences encoding a Cry1B or Cry1D protein.

BACKGROUND OF THE INVENTION

Strain and proteins derived from *Bacillus thuringiensis* (abbreviated herein as "Bt") are well known for their specific toxicity to insect pests, and they have been used since almost a century to control insect pests. Some transgenic plant species expressing Bt proteins are now available, and they successfully limit insect damage on plants. Despite the isolation of quite a number of insecticidal Bt proteins, only a few Bt proteins have been expressed in transgenic plants that have been commercialized, and this only in some crops. Most commercialized transgenic Bt plants belong to the bigger field crops such as corn and cotton. In smaller market crops such as vegetables, only a few plant species have been transformed with Bt genes so as to render them resistant to major Lepidopteran insect pests, but to date no Lepidopteran-resistant vegetable Bt-plant or seed is deregulated and marketed. Zhao et al. (2003) have described transgenic broccoli plants expressing a Cry1Ac or a Cry1C Bt toxin, as well as crosses between these plants so that both the Cry1Ac and Cry1C toxins are expressed in the same plants, but these plants have not been commercialized. NewLeaf™ potatoes comprising a Cry3A Coleopteran-active gene were briefly commercialized in Northern America, but have been withdrawn from the market in 2001.

The current invention provides new genes encoding proteins of the Cry1C type of Bt proteins, which ideally are combined with genes encoding proteins of the Cry1B or Cry1D type Bt proteins.

The DNA sequences of the cry1C, cry1B or cry1D genes of the invention and of the modified transit peptide of the invention (shown in the enclosed sequence listing) are artificial genes, not found in nature, and are different from any known DNA sequence. Indeed, any one of the DNA sequences of SEQ ID Nos. 1, 3, 10, 14 or 16 shows at most 76.6% sequence identity with the closest known DNA sequences.

OBJECTS AND SUMMARY OF THE INVENTION

In the current invention, several new insect control genes derived from Bt are provided for use in plants. Specifically, such genes are useful in vegetables plant crops, particularly Brassicaceae plants such as cauliflower, cabbage, Chinese cabbage, turnip, mustard, oilseed rape, kale, broccoli, Brussels sprouts, mustard spinach, and the like. Particularly, in one embodiment of this invention the following *Brassica* species plants are protected from insects by the new genes of the current invention: *B. carinata, B. elongata, B. fruticulosa, B. juncea, B. napus, B. narinosa, B. nigra, B. oleracea, B. perviridis, B. rapa, B. rupestris, B. septiceps, B. tournefortii*, and the like, particularly plants of the species *Brassica oleraceae* or *Brassica napus*. The plants or seeds comprising at least one of the new genes of the invention can be obtained by transformation of plant cells and production of plants or seed therefrom comprising the genes of the invention. Also included herein are plants or seeds obtained by crossing with a plant transformed to contain at least one of the genes of the invention, and by application of routine breeding steps. Obviously, any plant species to be protected from insect species that are killed or controlled by the Bt proteins encoded by the novel genes of this invention can be transformed with the genes of the invention to obtain transgenic plants and seeds with increased resistance to such insects.

In one embodiment, the current invention also provides a combination of technologies to allow for the most optimal product from a resistance management point of view. Indeed, in one embodiment of this invention the plants of the invention produce at least 2 different Bt proteins and such proteins are encoded by the highly-expressed cry genes of the invention which have been stably integrated, preferably at a single locus in the plant's genome. In one embodiment of the invention, such at least 2 Bt genes include a cry1C and a cry1B gene, a cry1C and a cry1D gene, or a combination of a cry1C, a cry1B and a cry1D gene of this invention. In one embodiment of the invention a marker gene allowing rapid identification of transgenic plants, preferably a herbicide resistance gene, is located in the same plant, particularly at the same locus in the plant's genome as a cry gene of the invention. In one embodiment of this invention, the marker gene is a gene encoding a phosphinothricin acetyltransferase or a glyphosate-insensitive EPSPS.

In the invention also novel cry1B and cry1D genes, particularly cry1B or cry1D chimeric genes, are provided, which can be expressed in plants at high levels, such as the cry1B1 and cry1B2 and the cry1D1 and cry1D2 genes. Also plants cells, plants or seeds comprising any of these genes and methods of producing or using them alone or in combination are provided herein.

Also, the current invention provides novel genes encoding an insecticidal protein comprising a functional plant intron in their coding sequence. The presence of the intron also secures that the gene does not express a functional protein when the gene is in an environment where the intron cannot be spliced, such as a bacteria or another prokaryotic microorganism. The presence of this intron in the gene sequence also allows for high expression levels to be obtained in plants.

Also included herein are variants of the Cry1C protein of the invention comprising the sequence of SEQ ID No. 2 from amino acid position 29 to amino acid position 627, but wherein one, some or all of the following amino acids at the following positions compared to the positions in SEQ ID No. 2 are changed: the amino acid at position 125 is Alanine, the amino acid at position 184 is Valine, the amino acid at position 295 is Arginine, the amino acid at position 454 is Aspartic acid, or the amino acid at position 593 is Arginine. Also provided herein are variants of the Cry1B protein of the invention comprising the sequence of SEQ ID No. 11 from amino acid position 31 to 648, but wherein the amino acid at position 151 in SEQ ID No. 11 is Tyrosine or the amino acid at position 353 in SEQ ID No. 11 is Arginine, or a protein wherein the amino acid at position 151 in SEQ ID No. 11 is Tyrosine and the amino acid at position 353 in SEQ ID No. 11 is Arginine.

Also included in this invention is a novel DNA encoding a chloroplast transit peptide, particularly a DNA comprising the sequence of SEQ ID No. 16 from nucleotide position 7 to nucleotide position 371, particularly the sequence of SEQ ID No. 16, as well as such DNA encoding a variant of the protein of SEQ ID No. 17, such as a chloroplast transit peptide comprising the sequence of SEQ ID No. 17 from amino acid position 3 to amino acid position 124, wherein the Cys amino acid at position 55 is replaced by Tyr and/or wherein a Gly amino acid is added after the Gly amino acid at position 51.

Specifically, the current invention provides a chimeric gene, comprising the following operably-linked sequences: a) a coding region encoding a Cry1C protein, comprising the DNA of any one of SEQ ID Nos. 1, 3, 4 or 6 or a variant thereof, and b) a promoter region capable of directing expression in plant cells. In one embodiment, such promoter comprises the sequence of SEQ ID No. 18 or 19. In another embodiment, the chimeric gene further comprises a 3' polyadenylation and transcript termination region, particularly that of the NADP-malic enzyme gene from *Flaveria bidentis*. In another embodiment, the chimeric gene further comprises the leader sequence of the tapetum specific E1 gene of *Oryza sativa* between the promoter and the coding region.

The current invention also provides a DNA comprising any of the above chimeric genes, further comprising a second chimeric gene, said second chimeric gene comprising the following operably-linked sequences: a) a second coding region encoding a Cry1B protein comprising the DNA of SEQ ID No. 8 or 10, and b) a second promoter region capable of directing expression in plant cells; or a DNA comprising any of the above chimeric genes, further comprising a second chimeric gene, said second chimeric gene comprising the following operably-linked sequences: a) a coding region encoding a Cry1D protein comprising the DNA of SEQ ID No. 12 or 14, and b) a promoter region capable of directing expression in plant cells. In one embodiment, the above DNAs are provided, wherein said second promoter region comprises the sequence of SEQ ID No. 18 or 19 and is different from said first promoter region; or wherein said second chimeric gene further comprises a 3' polyadenylation and transcript termination region, particularly of the NADP-malic enzyme gene from *Flaveria bidentis*. In one embodiment, the second chimeric gene in these DNAs further comprises the leader sequence of the tapetum specific E1 gene of *Oryza sativa* between the promoter and the coding region.

The current invention also provides the above DNAs, further comprising a third chimeric gene, said third chimeric gene comprising the following operably-linked sequences: a) a coding region encoding a Cry1D protein comprising the DNA of SEQ ID No. 12 or 14, and b) a promoter region capable of directing expression in plants:

Also included in the current invention are a transgenic plant cell or plant, comprising any of the above genes or DNAs stably incorporated in its genome, preferably when the cell or plant is a *Brassica* species plant or plant cell, particularly of the species *Brassica oleraceae*, more particularly cabbage or cauliflower.

Also included in this invention is the use of any of the above chimeric genes or DNAs to control insect pests, to obtain plant cells, plants or seeds with increased resistance to insects; the use of any of the above chimeric genes or DNAs to delay or prevent insect resistance development in transgenic plants expressing an insecticidal protein by insects attempting to feed on such plants; or the use of any of the above chimeric genes or DNAs to obtain cabbage, oilseed rape or cauliflower protected from *Plutella xylostella*. Also included herein are methods for controlling insects, comprising the step of planting or sowing in a field, plants comprising any of the above chimeric genes or DNAs; as well as methods of controlling insects in *Brassica* species plants, comprising the step of expressing any of the above chimeric genes or DNA in plants; or methods of producing plants or seeds resistant to insects, comprising the steps of: a) obtaining a plant transformed with the gene of any one of claims 1 to 5 or the DNA of any one of claims 6 to 12, and b) selecting progeny of said plant or seeds thereof, containing said gene or DNA.

Also provided in accordance with this invention is a chimeric gene comprising the following operably-linked sequences: a) a first fragment of a coding sequence encoding an insecticidal protein, b) a plant intron sequence, c) a second fragment of said coding sequence, d) a promoter region capable of directing expression in plant cells, and wherein no insecticidal protein can be produced from such chimeric gene in a given host cell wherein the intron is not spliced; particularly such chimeric gene wherein such intron is the second intron of the ST-LS1 gene of *Solanum tuberosum*.

Further provided herein is also a microorganism comprising any of the above chimeric genes or DNAs, particularly when such microorganism is of the genus *Escherichia*, *Bacillus* or *Agrobacterium*.

DESCRIPTION

In accordance with this invention, a "nucleic acid sequence" refers to a DNA or RNA molecule in single or double stranded form, preferably a DNA molecule. An "isolated DNA", as used herein, refers to a DNA which is not naturally-occurring or no longer in the natural environment wherein it was originally present, e.g., a DNA coding sequence associated with other regulatory elements in a chimeric gene, a DNA transferred into another host cell, such as a plant cell, or an artificial, synthetically-made DNA sequence having a different nucleotide sequence compared to any naturally-occurring DNA sequence.

In accordance with this invention, nucleic acid sequences, particularly DNA sequences, encoding Bt Cry toxins or variants thereof have been constructed. The new DNA sequences are designated herein as cry1C1-4, cry1B1, cry1B2, cry1D1, and cry1D2, and their encoded proteins are designated herein as Cry1C (e.g., Cry1C1, Cry1C3, and Cry1C4), Cry1B (e.g., Cry1B1 and Cry1B2) and Cry1D (e.g., Cry1D1 and Cry1D2) proteins. Also a new DNA sequence encoding a modified chloroplast transit peptide is provided herein, e.g., a DNA comprising the sequence of SEQ ID No. 16 from nucleotide position 7 to nucleotide position 371, particularly the sequence of SEQ ID No. 16, which is designed for optimal expression in plants, particularly vegetables such as Brassicaceae plants, especially cabbage and cauliflower.

In accordance with this invention "Cry1C protein" refers to any insecticidal protein comprising the smallest fragment of the amino acid sequence of SEQ ID No. 2 which retains insecticidal activity (hereinafter referred to as "smallest toxic fragment"), particularly any protein comprising the amino acid sequence from the amino acid at position 29 to the amino acid at position 627 in SEQ ID No. 2, preferably any insecticidal protein comprising the amino acid sequence of SEQ ID No. 2 from amino acid position 3 to amino acid position 627. Also included herein is an insecticidal protein comprising the amino acid sequence of SEQ ID No. 2 (also named Cry1C1 protein herein), SEQ ID No. 5 (also named Cry1C3 protein herein) or SEQ ID No. 7 (also named Cry1C4 protein herein).

A Cry1C protein comprising the amino acid sequence from the amino acid at position 29 to the amino acid at position 627 in SEQ ID No, 2 retains all or most of the insecticidal activity of the entire protein as produced in nature, and addition of protein sequences at the N- or C-terminal part thereof do not disrupt this activity. Hence, any protein characterized by an amino acid sequence containing or including this region is useful and forms part of this invention. This includes insecticidal hybrid or chimeric proteins comprising the smallest toxic protein fragment of the protein of SEQ ID No. 2. Also included in this definition are variants of proteins comprising the amino acid sequence from the amino acid at position 29 to the amino acid at position 627 in SEQ ID No. 2, such as insecticidal proteins comprising a sequence having a sequence identity of at least 95%, particularly at least 96%, 97%, 98% or 99% at the amino acid sequence level with this region of SEQ ID No. 2, as determined using the Needleman-Wunsch global alignment algorithm in EMBOSS (Rice et al., 2000) to find optimum alignment over the entire length of the sequences, using default settings (gap opening penalty 10, gap extension penalty 0.5; for amino acid sequence comparisons, the EBLOSUM62 matrix is used), preferably proteins having some, preferably 5-10, particularly less than 5, amino acids added, replaced or deleted without significantly changing, preferably without changing, the insecticidal activity of the protein. Preferred variants of the Cry1C protein of the invention include a protein comprising the sequence of SEQ ID No. 2 from amino acid position 29 to amino acid position 627, but wherein one, some or all of the following amino acids at the following positions compared to the positions in SEQ ID No. 2 are changed: the amino acid at position 125 is Alanine, the amino acid at position 184 is Valine, the amino acid at position 295 is Arginine, the amino acid at position 454 is Aspartic acid, or the amino acid at position 593 is Arginine. Also included herein are any Cry1C-based protein variants, hybrids or mutants retaining substantially the same insecticidal activity as that of the Cry1C protein of the invention defined above.

The terminology DNA or protein "comprising" a certain sequence X, as used herein, refers to a DNA or protein including or containing at least the sequence X, so that other nucleotide or amino acid sequences can be included at the 5' (or N-terminal) and/or 3' (or C-terminal) end, e.g. (the nucleotide sequence of) a selectable marker protein as disclosed in EP 0 193 259, (the nucleotide sequence of) a transit peptide, and/or a 5' or 3' leader sequence.

For the purpose of this invention, the "sequence identity" of two related nucleotide or amino acid sequences, expressed as a percentage, refers to the number of positions in the two optimally aligned sequences which have identical residues (×100) divided by the number of positions compared. A gap, i.e., a position in an alignment where a residue is present in one sequence but not in the other, is regarded as a position with non-identical residues. The alignment of the two sequences is performed by the Needleman and Wunsch algorithm (Needleman and Wunsch 1970) in EMBOSS (Rice et al., 2000) to find optimum alignment over the entire length of the sequences, using default settings (gap opening penalty 10, gap extension penalty 0.5).

The "smallest toxic fragment" of a Cry protein of the invention, as used herein, is that smallest fragment or portion of a Cry protein retaining insecticidal activity that can be obtained by enzymatic, such as trypsin or chymotrypsin, digestion of the full length Cry protein, or that smallest fragment or portion of a Cry protein retaining insecticidal activity that can be obtained by making nucleotide deletions in the DNA encoding a Cry protein. Such smallest toxic fragment can also be obtained by treatment of a Cry protein with insect gut juice, preferably midgut juice, from an insect species susceptible to (i.e., killed or otherwise negative affected in its growth or feeding by) such Cry protein.

In accordance with this invention, "Cry1D protein" refers to any insecticidal protein comprising the smallest toxic fragment of the amino acid sequence of SEQ ID No. 15, particularly any insecticidal protein comprising the amino acid sequence from the amino acid at position 21 or 29 to the amino acid at position 604 in SEQ ID No. 15, preferably any insecticidal protein comprising the amino acid sequence of SEQ ID No. 15 from amino acid position 3 to amino acid position 604. Also included herein is an insecticidal protein comprising the amino acid sequence of SEQ ID No. 13 (also named Cry1D1 protein herein) or SEQ ID No. 15 (also named Cry1D2 protein herein). A Cry1D protein comprising the amino acid sequence from the amino acid at position 29 to the amino acid at position 604 in SEQ ID No. 15 retains all or most of the insecticidal activity of the entire protein as produced in nature, and addition of protein sequences at the N- or C-terminal part thereof do not disrupt this activity. Hence, any protein characterized by an amino acid sequence containing or including this region is useful and forms part of this invention. This includes insecticidal hybrid or chimeric proteins comprising the smallest toxic protein fragment of the protein of SEQ ID No. 15. Also included in this definition are protein variants differing in the amino acid sequence from the amino acid at position 29 to the amino acid at position 604 in SEQ ID No. 15, such as proteins with a sequence identity of at least 95%, particularly at least 97%, at least 98% or at least 99% at the amino acid sequence level in this region of SEQ ID No. 15, as determined using the Needleman-Wunsch global alignment algorithm in EMBOSS (Rice et al., 2000) to find optimum alignment over the entire length of the sequences, using default settings (gap opening penalty 10, gap extension penalty 0.5, for amino acid sequence comparisons, the EBLOSUM62 matrix is used), preferably proteins having some, preferably 5-10, particularly less than 5, amino acids added, replaced or deleted in the region from the amino acid at position 29 to the amino acid at position 604 in SEQ ID No. 15 without significantly changing, preferably without changing, the insecticidal activity of the protein.

In accordance with this invention, "Cry1B protein" refers to any insecticidal protein comprising the smallest toxic fragment of the amino acid sequence of SEQ ID No. 11, particularly any insecticidal protein comprising the amino acid sequence from the amino acid at position 31 to the amino acid at position 648, in SEQ ID No. 11, preferably any insecticidal protein comprising the amino acid sequence of SEQ ID No. 11 from amino acid position 3 to amino acid position 648. Also included herein is any insecticidal protein comprising the amino acid sequence of SEQ ID No. 11 or SEQ ID No. 9. A Cry1B protein comprising the amino acid sequence from the amino acid at position 31 to the amino acid at position 648 in SEQ ID No. 11 retains all or most of the insecticidal activity of the entire protein as produced in nature, and addition of protein sequences at the N- or C-terminal part thereof do not disrupt this activity. Hence, any protein characterized by an amino acid sequence containing or including this region is useful and forms part of this invention. This includes insecticidal hybrids or chimeric proteins comprising the smallest toxic protein fragment of SEQ ID No. 11. Also included in this definition are insecticidal proteins comprising variants of the amino acid sequence from the amino acid at position 31 to the amino acid at position 648 in SEQ ID No. 11, such as insecticidal proteins having a sequence identity of at least 80%, particularly at least 85%, 90%, 95%, 96%, 97%, 98%, or at least 99% at the amino acid sequence level in this region of SEQ ID No. 11, as determined using pairwise alignments using the Needleman-Wunsch global alignment algorithm in EMBOSS (Rice et al., 2000) to find optimum alignment over the entire length of the sequences, using default settings (gap opening penalty 10, gap extension penalty 0.5, for amino acid sequence comparisons, the EBLOSUM62 matrix is used), preferably proteins having some, preferably 5-10, particularly less than 5, amino acids added, replaced or deleted in the amino acid sequence from the amino acid at position 31 to the amino acid at position 648 in SEQ ID No. 11 without significantly changing, preferably without changing, the insecticidal activity of the protein. Preferred variants of the Cry1B protein of the invention include an insecticidal protein comprising the sequence of SEQ ID No. 11 from amino acid position 31 to 648, but wherein the amino acid at position 151 in SEQ ID No. 11 is Tyrosine or the amino acid at position 353 in SEQ ID No. 11 is Arginine, or a protein wherein the amino acid at position 151 in SEQ ID No. 11 is Tyrosine and the amino acid at position 353 in SEQ ID No. 11 is Arginine.

As used herein, the terms DNA or gene, as in "cry1C1 DNA", refers to any DNA sequence encoding the Cry1C, Cry1B or Cry1D protein, respectively, as defined above. This includes naturally occurring, artificial or synthetic DNA sequences encoding the Cry1C, Cry1B or Cry1D proteins defined above such as any one of SEQ ID Nos. 2, 5, 7, 9, 11, 13, 15. Also included herein are DNA sequences encoding insecticidal proteins which are similar enough to any one of the DNA sequences of SEQ ID No. 1, 3, 4, 6, 8, 10, 12, or 14 so that they can (i.e., have the ability to) hybridize to these DNA sequences under stringent hybridization conditions. Stringent hybridization conditions, as used herein, refers particularly to the following conditions: immobilizing the relevant DNA sequences on a filter, and prehybridizing the filters for either 1 to 2 hours in 50% formamide, 5% SSPE, 2×Denhardt's reagent and 0.1% SDS at 42° C., or 1 to 2 hours in 6×SSC, 2×Denhardt's reagent and 0.1% SDS at 68° C. The denatured dig- or radio-labeled probe is then added directly to the prehybridization fluid and incubation is carried out for 16 to 24 hours at the appropriate temperature mentioned above. After incubation, the filters are then washed for 30 minutes at room temperature in 2×SSC, 0.1% SDS, followed by 2 washes of 30 minutes each at 68° C. in 0.5×SSC and 0.1% SDS. An autoradiograph is established by exposing the filters for 24 to 48 hours to X-ray film (Kodak XAR-2 or equivalent) at −70° C. with an intensifying screen. Of course, equivalent conditions and parameters can be used in this process while still retaining the desired stringent hybridization conditions. Preferred variants of the cry1C, cry1B or cry1D DNA of this invention are a DNA encoding the insecticidal Cry1C, Cry1B or Cry1D protein variants described above.

Also included herein as a Cry1C DNA or gene as defined herein are: a) a DNA comprising the nucleotide sequence of SEQ ID No. 1 from nucleotide position 85 to nucleotide position 2073, b) a DNA comprising the nucleotide sequence of SEQ ID No. 3 from nucleotide position 85 to nucleotide position 2073, c) a DNA comprising the nucleotide sequence of SEQ ID No. 1 from nucleotide position 85 to nucleotide position 2073 fused to the DNA sequence of SEQ ID No. 16, d) a DNA comprising the nucleotide sequence of SEQ ID No. 4 from nucleotide position 7 to nucleotide position 2439, e) a DNA comprising the nucleotide sequence of SEQ ID No. 3 from nucleotide position 85 to nucleotide position 2073 fused to the DNA sequence of SEQ ID No. 16, or f) a DNA comprising the nucleotide sequence of SEQ ID No. 6 from nucleotide position 7 to nucleotide position 2439.

Also included herein as a Cry1D DNA or gene as defined herein are: a) a DNA comprising the nucleotide sequence of SEQ ID No. 14 from nucleotide position 85 to nucleotide position 1812, or b) a DNA comprising the nucleotide sequence of SEQ ID No. 12 from nucleotide position 7 to nucleotide position 2178.

Also included herein as a Cry1B DNA or gene as defined herein are: a) a DNA comprising the nucleotide sequence of SEQ ID No. 8 from nucleotide position 7 to nucleotide position 2310, or b) a DNA comprising the nucleotide sequence of SEQ ID No. 10 from nucleotide position 91 to nucleotide position 1944.

The DNA sequences of the cry1C, cry1B or cry1D genes of the invention (as shown in the sequence listing, without transit peptide sequence) show at most only 76.6% sequence identity with the closest previously known DNA sequences available in databases. Available sequence databases were checked for the sequences with closest sequence identity using the well-known BLAST algorithm, and then the Needleman-Wunsch global alignment algorithm in EMBOSS (Rice et al., 2000) was used to find the optimum alignment between the closest sequences and the sequences of the invention (considering their entire length, using default settings (gap opening penalty 10, gap extension penalty 0.5). For the Cry1D DNA, a fragment of the prior art sequence (of equal length) was selected to secure optimal alignment, but even then only 72.5% sequence identity was the closest sequence identity with any known DNA sequence listed in the available databases.

Hence, also included herein as cry1C, cry1B or cry1D genes are DNA sequences encoding an insecticidal protein with at least 80%, 90%, preferably at least 93 to 97%, particularly at least 98% or at least 99%, sequence identity to any one of the coding sequences of SEQ ID No. 1, 3, 4, 6, 8, 10, 12, or 14 or DNA sequences encoding an insecticidal protein hybridizing to any one of SEQ ID No. 1, 3, 4, 6, 8, 10, 12; or 14 under stringent hybridization conditions, preferably hybridizing stringently to that part of the DNA sequence of any one of SEQ ID No. 1, 3, 4, 6, 8, 10, 12, or 14 which is required to encode the smallest toxic protein fragment of the proteins of this invention. The DNA sequence identities referred to herein are calculated using the Needleman-Wunsch global alignment algorithm in EMBOSS (Rice et al., 2000) to find optimum alignment over the entire length of the sequences, using default settings (gap opening penalty 10, gap extension penalty 0.5; for DNA sequence comparisons, the EDNAFULL matrix is used), the stringent hybridization conditions are as defined above.

"Insecticidal activity" of a protein, as used herein, means the capacity of a protein to kill insects, inhibit their growth or cause a reduction in insect feeding when such protein is ingested by insects, preferably by expression in a recombinant host such as a plant cell. It is understood that activity to insects of one insect species, preferably the larvae thereof, is sufficient for a protein to have insecticidal activity as used herein, although often insects of different insect species are affected by the proteins of the invention. The recombinant hosts expressing at least one of the Cry1C, Cry1B or Cry1D proteins of the invention are typically developed for or targeted to a specific major insect pest species for a certain crop or region where such insect species is a pest, e.g., the diamondback moth for *Brassica* plant species, but other insects will often also be controlled by the recombinant hosts of the invention, such as by the transgenic plant cells or plants, e.g., the exemplified transgenic *Brassica* cauliflower or cabbage plant cells or plants of the invention comprising the cry1C and/or cry1B gene in accordance with the invention.

"(Insect-)controlling amounts" of or "control" by a protein, or a recombinant host expressing a protein of this invention, as used herein, refers to an amount of protein which is sufficient to limit damage to a plant by insects feeding on such plant, e.g. by killing the insects or by inhibiting the insect development, fertility or growth in such a manner that an insect species provides less damage to a plant. This does not mean that treatment of plants with chemical insecticides will no be longer necessary (e.g., to control insect species not affected by the proteins of the invention, such as (secondary) Coleopteran or Dipteran insect pests), but that treatment by chemical insecticides for the insects targeted by the proteins of the invention can be significantly reduced or avoided, while still obtaining acceptable plant performance in the field and acceptable yield.

In accordance with this invention, insects susceptible to the new Cry proteins of the invention are contacted with these proteins in insect-controlling amounts, preferably insect-killing amounts. In one embodiment of this invention, recombinant hosts of the invention, such as transgenic plant cells or plants of the invention, express a protein or a combination of proteins of the invention at high levels, such that a "high dose" level is obtained. A "high dose level", "high dose insect resistance" or "high dose" expression, as used herein when referring to a recombinant plant cell or plant, refers to a concentration of the insecticidal protein in a plant cell or plant (measured by ELISA as a percentage of the total soluble protein, which total soluble protein is measured after extraction of soluble proteins in an extraction buffer (e.g., the extraction buffer described in Jansens et al., 1997) using Bradford analysis (Bio-Rad, Richmond, Calif.; Bradford, 1976)) which kills a developmental stage of the target insect which is significantly less susceptible, preferably between 25 to 100 times less susceptible to the toxin than the first larval stage of the insect and can thus can be expected to ensure full control of the target insect. In one embodiment this refers to the obtaining of at least 97 percent, preferably at least 99 percent, most preferably 100 percent, mortality for the fourth larval instar (for insects having 5 larval instars) or the last larval instar (for insects having 4 or less larval instars) of a target insect, as measured 10 to 14 days after insect infestation of such plant cells or plant in routine insect bioassays, preferably whole plant bioassays, using suitable controls. The existence of one target insect species (i.e., an insect species, preferably the larvae thereof, which can cause significant damage to a plant species or variety, and which is typically an insect for which a transgenic Bt plant is designed and developed) for which transformed plant cells or plants according to this invention provide a "high dose" level insect resistance is sufficient for a plant to be designated as giving "high dose" expression in accordance with this invention. Preferred target insects for the proteins of this invention are economically damaging insect pests of plants.

The terms "Cry1 protein/DNA" or "Cry protein/DNA of this Invention", as used herein, refer to any one of the Cry1C, Cry1B, or Cry1D proteins or any one of the cry1C, cry1B or cry1D DNA sequences as defined herein. A Cry or Cry1 protein, as used herein, can be a protein in the full length size, also named a protoxin, or can be in a truncated form as long as the insecticidal activity is retained, or can be a combination of different proteins in a hybrid or fusion protein. A "protoxin" refers to the full length insecticidal crystal protein as it is encoded by the naturally-occurring Bt DNA sequence, a "toxin" refers to an insecticidal fragment thereof, particularly the smallest toxic fragment thereof, typically in the molecular weight range of about 50-65 kD, particularly about 60 kD, as determined by SDS-PAGE electrophoresis compared to routinely-used molecular weight standards.

A "chimeric gene", as used herein, is used to refer to a gene or DNA sequence comprising at least two different DNA fragments (such as a promoter, 5' untranslated leader, coding region, intron, 3' untranslated trailer, and a 3' end transcript formation and polyadenylation region) which are not naturally associated with each other or which originate from different sources. Typically, a plant-expressible chimeric gene, as used herein, is a gene comprising a promoter region operably-linked to a synthetic, man-made coding sequence such as any of the cry1C, cry1B or cry1D genes of the invention.

The DNA sequences encoding the Cry1 proteins of the invention can be chemically synthesized using routine techniques, and can be inserted in expression vectors to produce high amounts of Cry1 proteins. The Cry1 proteins can be used to prepare specific monoclonal or polyclonal antibodies in a conventional manner (Höfte et al., 1988) to develop immuno-assays (e.g., ELISA, Western blotting, antibody-coated dip-sticks) to detect the presence of absence of these proteins in any material, such as plant material.

The tools developed to identify transgenic plant cells, plants, or plant materials such as leaves or seeds comprising any one of the cry1 genes of the invention integrated in their genome, or DNA-containing products which comprise or are derived from plant material comprising a cry1 gene of the invention are based on the specific sequence characteristics of the novel genes of the invention, such as, a specific restriction map of the genomic region comprising the introduced (foreign) cry1 gene, molecular markers or the sequence of the foreign DNA integrated in the plant's genome.

Once the sequence of a foreign DNA such as the cry1 genes of the invention is known, primers and probes can be developed which specifically recognize these sequences in the nucleic acid (DNA or RNA) of a sample by way of a molecular biological technique. For instance a PCR method can be developed to identify the genes of the invention in biological samples (such as samples of plants, plant material or products comprising plant material). Such a PCR is based on at least two specific "primers", e.g., one recognizing a sequence within the cry1 gene and the other recognizing a sequence within the associated transit peptide sequence or within the regulatory regions such as the promoter or 3' end of the chimeric gene comprising said cry1 gene of the invention, or both recognizing specifically the cry1 gene of the invention. The primers preferably have a sequence of between 15 and 35 nucleotides which under optimized PCR conditions "specifically recognize" a sequence within the cry1 chimeric gene of the invention, so that a specific fragment ("integration fragment" or discriminating amplicon) is amplified from a nucleic acid sample comprising a cry1 gene of the invention. This means that only the targeted integration fragment, and no other sequence in the plant genome or foreign DNA, is amplified under optimized PCR conditions.

PCR primers suitable for the invention are oligonucleotides ranging in length from 17 nucleotides to about 200 nucleotides, comprising a nucleotide sequence of at least 17 consecutive nucleotides, preferably 20 consecutive nucleotides selected from the cry1C, cry1B or cry1D chimeric gene sequence as transferred to plant cells or plants of the invention.

The primers may of course be longer than the mentioned 17 consecutive nucleotides, and may, e.g., be 20, 21, 30, 35, 50, 75, 100, 150, 200 nt long or even longer. The primers may entirely consist of nucleotide sequences selected from the cry1 nucleotide sequences. However, the nucleotide sequence of the primers at their 5' end (i.e. outside of the 3'-located 17 consecutive nucleotides) is less critical. Thus, the 5' sequence of the primers may consist of a nucleotide sequence selected from the cry1 chimeric gene sequence, as appropriate, but may contain several (e.g. 1, 2, 5, 10) mismatches. The 5' sequence of the primers may even entirely consist of a nucleotide sequence unrelated to the cry1 genes of the invention, such as a nucleotide sequence representing one or more restriction enzyme recognition sites. Such unrelated sequences or flanking DNA sequences with mismatches should preferably be no longer than 100, more preferably no longer than 50 or no longer than 25 nucleotides.

Moreover, suitable primers may comprise or consist of a nucleotide sequence at their 3' end spanning the joining region between the cry1 gene of the invention and the associated transit peptide sequence or the regulatory elements in the cry1 chimeric gene integrated in the plant DNA, such as a promoter sequence, a leader sequence, a trailer sequence or a 3' transcript termination and polyadenylation sequence. It will also be immediately clear to the skilled artisan that properly selected PCR primer pairs should also not comprise sequences complementary to each other.

The term "primer" as used herein encompasses any nucleic acid that is capable of priming the synthesis of a nascent nucleic acid in a template-dependent process, such as PCR. Typically, primers are oligonucleotides from 10 to 30 nucleotides, but longer sequences can be employed. Primers may be provided in double-stranded form, though the single-stranded form is preferred. Probes can be used as primers, but are designed to bind to the target DNA or RNA and need not be used in an amplification process.

The term "recognizing" as used herein when referring to specific primers, refers to the fact that the specific primers specifically hybridize to a nucleic acid sequence in the cry1 genes of the invention under a standard PCR identification protocol, whereby the specificity is determined by the presence of positive and negative controls as is well known in the art.

Also included herein is a kit to detect the cry1 genes of the invention in biological material, as well as the use of such kit to screen biological material. A "kit" as used herein refers to a set of reagents for the purpose of performing the identification of the cry1 genes of the invention in biological samples. More particularly, a preferred embodiment of the kit of the invention comprises at least one or two specific primers, as described above. Optionally, the kit can further comprise any other reagent described herein in the PCR identification protocol. Alternatively, according to another embodiment of this invention, the kit can comprise a specific probe, as described above, which specifically hybridizes with nucleic acid of biological samples to identify the presence of the cry1 genes therein. Optionally, the kit can further comprise any other reagent (such as but not limited to hybridizing buffer, label) for identification of the cry1 genes in biological samples, using the specific probe.

Standard PCR protocols are described in the art, such as in 'PCR Applications Manual" (Roche Molecular Biochemicals, 2nd Edition, 1999). The optimal conditions for the PCR, including the sequence of the specific primers, is specified in a PCR identification protocol for each cry1 gene-containing plant species. It is however understood that a number of parameters in the PCR identification protocol may need to be adjusted to specific laboratory conditions, and may be modified slightly to obtain similar results. For instance, use of a different method for preparation of DNA may require adjustment of, for instance, the amount of primers, polymerase and annealing conditions used. Similarly, the selection of other primers may dictate other optimal conditions for the PCR identification protocol. These adjustments will however be apparent to a person skilled in the art, and are furthermore detailed in current PCR application manuals such as the one cited above.

Examples of suitable primer combinations in accordance with the invention are (sequence 5'-3') for the cry1B gene of the invention: P1B227 (TAC TTC GAA CAG AAA GM CGA GM CGA. G, SEQ ID No. 20) and P1B228 (GTC CAG CGA MG GM CTC CAA GAA, SEQ ID No. 21), and for the cry1C gene of the invention: P1C247 (AAC CTT GAG GGA CTT GGA MC, SEQ ID No. 22) and P1C252 (AAG ATG AGG GTT TCT GAT AGC AG, SEQ ID No. 23). Hence, any gene encoding an insecticidal Cry1B or Cry1C protein and specifically recognized by these primers is included herein, as well as any method to detect such genes using such or other specific primers.

Also specific markers or labeled probes can be designed to detect the DNA sequences of this invention, and any use of specific markers or probes directed to any of the cry1C, cry1B or cry1D genes of the invention is included herein. In one embodiment of this invention, the specific markers, primers or labeled probes do not detect or recognize any plant, preferably any plant of the same species as the test plant, not containing a cry1 DNA sequence of the invention, particularly any such markers, primers or labeled probes do not detect or recognize any plant expressing a Cry1C, Cry1D or Cry1B protein wherein such plant does not contain a DNA sequence of the invention (such as a cry1C, cry1D or cry1B DNA as defined herein, e.g., a DNA comprising the nucleotide sequence of any one of SEQ ID No. 1, 3, 4, 6, 8, 10, 12, or 14).

The DNA sequences of this invention can be slightly modified to allow for more convenient restriction enzyme sites, or to make small changes without changing the efficacy and without significantly changing, preferably without changing, the protein they encode. Indeed, because of the degeneracy of the genetic code, it is well known that most amino acid codons can be replaced by others without changing the amino acid sequence of the protein. Furthermore, some amino acids can be substituted by other equivalent amino acids without significantly changing, preferably without changing, the insecticidal activity of the protein. Also, changes in amino acid sequence or composition in regions of the molecule, different from those responsible for binding or pore formation are less likely to cause a difference in insecticidal activity of the protein (e.g., the C-terminal part of the Cry1 protoxin can be removed or be replaced by another amino acid sequence without affecting the insecticidal activity of the Cry1 proteins of the invention). Equivalents of the DNA sequences of the invention include DNA sequences with less than 20, preferably 5-10, nucleotide differences compared to the cry1 genes of this invention as defined herein, but which encode an insecticidal Cry1 protein of the invention, as defined herein.

Small modifications to a DNA sequence such as described above can be routinely made, i.e., by PCR-mediated mutagenesis (Ho et al., 1989, White et al., 1989). More profound modifications to a DNA sequence can be routinely done by de novo DNA synthesis of a desired coding region using available techniques.

The term "encoding", as used herein, when referring to a gene encoding a protein, refers to the capacity of such gene to produce a protein upon transcription and translation of the coding sequence contained in such gene in a target host cell. Hence, the cry1C1 chimeric gene of the invention encodes the Cry1C1 protein of the invention, even though this gene contains two coding sequences interrupted by a non-coding intron sequence.

With the term "substantially the same", when referring to the amino acid sequence of a Cry1 protein of this invention, is meant to include an amino acid sequence that differs in no more than 5%, preferably no more than 2%, to the amino acid sequence of the protein compared to; and when referring to toxicity of Cry protein, is meant to include a protein whose LC50 value obtained under the same conditions of bio-assay (preferably in the same bio-assay using insects from the same population and suitable controls) differs no more then 2 times, preferably no more than 50%, of the LC50 value obtained for the protein compared to.

"Microorganism", as used herein, refers to any living organism that can be observed only with the aid of a microscope, such as bacteria, yeast cells, plant cells, viruses, fungi. This includes all generally unicellular organisms with dimensions beneath the limits of vision which can be propagated and manipulated in a laboratory, typically prokaryotic or unicellular eukaryotic life forms, including tissue cultures and plasmids.

The cry1 DNA sequences of the invention, prepared from total DNA, can be ligated in suitable expression vectors and transformed in suitable host cells which can then be screened by conventional detection tools for presence and expression of the toxin.

A database search with the genes of this invention indicates that the DNA sequences of the invention are significantly different from any previously described genes or DNA sequences encoding toxins with activity against Lepidoptera (see, e.g., the Jan. 26, 2006 version of DNA sequences described in patent applications (Geneseq release 200602), Hofte and Whiteley, 1989; Crickmore et al., 1998; and the Aug. 2, 2005 update on the Bt nomenclature website corresponding to the Crickmore et al. (1998) publication.

The closest sequence identity at the DNA level (for the entire length of the sequences of the invention) in available DNA sequence databases (from patent or scientific literature) was 76.60% for the cry1C DNA of SEQ ID No. 1 or 3, 73% for the cry1B DNA of SEQ ID No. 10, and 72.5% for the cry1D DNA of SEQ ID No. 14, using the above defined Needleman-Wunsch default settings in EMBOSS. Hence, assuming the available DNA sequence databases are representative of all known DNA sequences, the DNA sequences of this invention differ in at least 23% of their nucleotides from any previously known DNA sequence. Assuming the closest sequences are contained in the available databases, this reflects a difference in about 485 nucleotides for the nucleotide sequence of SEQ ID No. 1 or 3, a difference in about 524 nucleotides for the nucleotide sequence of SEQ ID No. 10, and a difference in about 498 nucleotides for the nucleotide sequence of SEQ ID No. 14 with their respective closest published DNA sequence. This difference will be even more pronounced for the DNA sequences of SEQ ID No. 4, 6, 8, or 12, which encode a fusion protein with a transit peptide. Also the optimized chloroplast transit peptide DNA sequence of this invention (SEQ ID No. 16), which was adapted for expression in the target plants of the invention, was found to have about 76.1% sequence identity (for that part of equal length to the SEQ ID No. 16 sequence) to the closest DNA sequence identified in available DNA sequence databases and hence is very different.

By an "insecticidally effective part (portion or fragment)" of DNA sequences encoding a Cry1 protein, also referred to herein as "truncated gene" or "truncated DNA", is meant a DNA sequence encoding a polypeptide which has fewer amino acids than the Cry1 protein protoxin form but which is still insecticidal.

In order to express all or an insecticidally effective part of the DNA sequence encoding a Cry protein of this invention in a recombinant host such as E. coli, in other Bt strains or in plants, suitable restriction sites can be introduced, flanking the DNA sequence. This can be done by site-directed mutagenesis, using well-known procedures (Stanssens et al., 1989; White et al., 1989). In order to obtain improved expression in plants, the cry1 genes of the invention are artificial genes, wherein the sequence has been adapted for optimal expression by DNA synthesis. In such sequence, replacement of DNA sequences inhibiting optimal expression is achieved by designing DNA sequences comprising codons more preferred by plants, preferably the target plant genus or species.

For obtaining enhanced expression in plants or preventing expression of an insecticidal protein when not present in a plant host cell (such as in a bacterial host cell), in one embodiments of the invention a plant intron is inserted in the chimeric cry1 genes of the invention, preferably in the coding sequence of at least one of the cry1 genes of the invention. Any of the known plant introns (e.g., Brown, 1986, Brown and Simpson, 1998, Brown et al., 1996) can be used herein as long as it is operably-linked to the coding sequence fragments so as to assure proper splicing. Operable linkage of the intron and the resulting proper splicing is conveniently checked in the target host plant species or cells thereof by RT-PCR or Northern blot or by any other means available in the art. In one embodiment an intron of a dicot plant gene is used in genes to be expressed in dicot plant cells, and a monocot intron is used in genes to be expressed in monocot plants. In one embodiment, the intron of the invention is the second intron of the light-inducible tissue-specific ST-LS1 gene of Solanum tuberosum (potato) as described by Eckes et al. (1986), e.g., the nucleotide sequence of SEQ ID No. 1 between nucleotide position 672 and 862. In one embodiment of this invention a plant intron is introduced into any Bt insecticidal protein coding sequence, particularly the intron of SEQ ID No: 1 between nucleotide position 672 and 862, so that it is effectively spliced in plant cells. Effective splicing in plants cells can be measured using routine techniques, such as RT-PCR, Northern blotting, or the detection of a functional protein produced in plant cells. Of course, for effective splicing the intron needs to be inserted in the correct position of the coding sequence so that functional 5' and 3' splice sites are obtained in the sequence. The two cry genes of the invention, illustrated in SEQ ID Nos. 1 and 3, each containing a plant intron at a different location, were found by RT-PCR analysis to both be effectively spliced in *Brassica oleraceae* plant cells, and to produce an mRNA encoding the expected Cry protein.

In accordance with one embodiment of this invention, the proteins are targeted to intracellular organelles such as plastids, preferably chloroplasts, mitochondria, or are secreted from the cell, potentially optimizing protein stability and/or expression. For this purpose, the chimeric genes of the invention comprise a coding region encoding a signal or target peptide, linked to the Cry protein coding region of the invention. Particularly preferred peptides to be included in the proteins of this invention are the transit peptides for chloroplast or other plastid targeting, especially duplicated transit peptide regions from plant genes whose gene product is targeted to the plastids, the optimized transit peptide described by Lebrun et al. (1996), or Capellades et al. (U.S. Pat. No. 5,635,618), the transit peptide of ferredoxin-NADP+oxidoreductase from spinach (Oelmuller et al., 1993), the transit peptide described in Wong et al. (1992) and the targeting peptides in published PCT patent application WO 00/26371. In one embodiment of the invention, the chloroplast transit peptide comprises the sequence of SEQ ID No. 17 from amino acid position 3 to amino acid position 124 or variant thereof, such as a chloroplast transit peptide comprising the sequence of SEQ ID No. 17 from amino acid position 3 to amino acid position 124, wherein the Cys amino acid at position 55 is replaced by Tyr in SEQ ID No. 17 and/or wherein a Gly amino acid is added after the Gly amino acid at position 51 in SEQ ID No. 17. Also preferred are peptides signalling secretion of a protein linked to such peptide outside the cell, such as the secretion signal of the potato proteinase inhibitor II (Keil et al., 1986), the secretion signal of the alpha-amylase 3 gene of rice (Sutliff et al., 1991) and the secretion signal of tobacco PR1 protein (Cornelissen et al., 1986).

Particularly useful signal peptides in accordance with the invention include the chloroplast transit peptide (e.g., Van Den Broeck et al. (1985), or the optimized chloroplast transit peptide of U.S. Pat. Nos. 5,510,471 and 5,635,618 causing transport of the protein to the chloroplasts, a secretory signal peptide or a peptide targeting the protein to other plastids, mitochondria, the ER, or another organelle. Signal sequences for targeting to intracellular organelles or for secretion outside the plant cell or to the cell wall are found in naturally targeted or secreted proteins, preferably those described by Klösgen et al. (1989), Klösgen and Weil (1991), Neuhaus & Rogers (1998), Bih et al. (1999), Morris et al. (1999), Hesse et al. (1989), Tavladoraki et al. (1998), Terashima et al. (1999), Park et al. (1997), Shcherban et al. (1995), all of which are incorporated herein by reference, particularly the signal peptide sequences from targeted or secreted proteins of *Brassica* plant species, corn, cotton, or soybean. A preferred DNA sequence encoding a transit peptide of the invention is a DNA comprising the sequence of SEQ ID No. 16 from nucleotide position 7 to nucleotide position 371, particularly the sequence of SEQ ID No. 16.

Furthermore, for any target pest insect, the binding properties of the Cry proteins of the invention can be evaluated, using methods known in the art (e.g., Van Rie et al., 1990), to determine if the Cry1 proteins of the invention bind to sites on a target insect midgut that are not recognized (or competed for) by other Cry or non-Cry proteins. Other Bt toxins binding to different binding sites in relevant susceptible insects, or other toxins derived from Bt strains or other sources (such as VIP toxins or insect (gut) proteinase inhibitors) with a different mode of action are very valuable to also express in a plant in addition to any one of the cry1 genes herein, to prevent or delay the development of insect resistance to a plant expressing insecticidal toxins. Because of the characteristics of the new cry1 genes, they are extremely useful for transforming plants, e.g. monocots such as corn or wheat and dicots such as cotton, soybean and *Brassica* species plants, to protect these plants from insect damage.

Especially for insect resistance management purposes for a specific insect pest, it is preferred to combine a cry1C gene of this invention with another gene encoding a different insect control protein, particularly a Bt crystal protein, which does not recognize at least one binding site recognized by such Cry1C protein in a target insect. Preferred insect control proteins to combine with the Cry1C proteins of this invention, particularly for simultaneous expression in plants, preferably *Brassica* species plants, particularly cabbage and cauliflower, include the Cry1B protein of this invention or the Cry1D protein of this invention, the VIP3Aa protein or a toxic fragment thereof as described in Estruch et al., 1996 and U.S. Pat. No. 6,291,156, or insecticidal proteins from Xhenorhabdus, *Serratia* or *Photorhabdus* species strains (e.g., Waterfield et al., 2001; ffrench-Constant and Bowen, 2000). In one embodiment, such co-expression is obtained by transforming a plant already expressing an insect control protein with a cry1 gene of this invention, or by crossing plants transformed with the insect control protein and plants transformed with the cry1 gene of this invention. For *Brassica* species plants, preferably the cry1 gene is used as first gene and as second gene the Cry1B, Cry1D or VIP3Aa protein or variants or derivatives thereof are used. Methods for obtaining expression of different Bt (or similarly, for other insect control proteins) insecticidal proteins in the same plant in an effort to minimize or prevent resistance development to transgenic insect-resistant plants are described in EP patent 0 408 403. In one embodiment of the invention, the cry1C gene of the invention is located in one and the same locus as a second insect control gene, such as a Cry1B or Cry1D gene, in the transgenic plant cells or plants of the invention, so that these genes do not segregate in the progeny of such plant cells or plants.

Preferably, for selection purposes but also for increasing the weed control options, the transgenic plants of the invention are also transformed with a DNA encoding a protein inactivating a broad-spectrum herbicide or encoding a protein which is a variant of the protein target for the herbicide but which protein variant is insensitive to such herbicide, e.g., herbicides based on glufosinate or glyphosate.

The insecticidally effective cry1 gene, preferably the cry1 chimeric gene, encoding an insecticidally effective portion of the Cry protoxin, can be stably inserted in a conventional manner into the nuclear genome of a plant cell, and the so-transformed plant cell can be used in a conventional manner to produce a transformed plant that is insect-resistant. In this regard, a disarmed Ti-plasmid, containing the insecticidally effective cry1 gene part, in *Agrobacterium*, e.g., *Agrobacterium tumefaciens* can be used to transform the plant cell, and thereafter, a transformed plant can be regenerated from the transformed plant cell using the procedures described, for example, in EP 0 116 718, EP 0 270 822, PCT publication WO 84/02913 and published European Patent application ("EP") 0 242 246 and in De Block et al. (1989). Preferred Ti-plasmid vectors each contain the insecticidally effective cry gene part between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm et al., 1990; Gordon-Kamm et al., 1990) and the method for transforming monocots generally (PCT publication WO 92/09696). For cotton transformation, especially preferred is the method described in PCT patent publication WO 00/71733. For soybean transformation, reference is made to methods known in the art, e.g., Hinchee et al. (1988) and Christou et al. (1990) or the method of WO 00/42207.

Also, besides transformation of the nuclear genome, also transformation of the plastid genome, preferably chloroplast genome, is included in the invention. Kota et al. (1999) have described a method to express a Cry2A protein in tobacco chloroplasts, and Lin et al. (2003) described expression of a cry1C gene in transplastomic tobacco plants.

The resulting transformed plant can be used in a conventional plant breeding scheme to produce more transformed plants with the same characteristics or to introduce the insecticidally effective cry gene part in other varieties of the same or related plant species. Seeds, which are obtained from the transformed plants, contain the insecticidally effective cry gene part as a stable genomic insert.

The insecticidally effective cry1 gene, preferably the sequence of SEQ ID No. 1, 3, 4 or 6, is inserted in a plant cell genome so that the inserted gene is downstream (i.e., 3') of, and under the control of, a promoter which can direct expression of the gene in a plant cell (herein named a "plant-expressible promoter"). This is preferably accomplished by inserting the cry1 chimeric gene comprising a plant-expressible promoter in the plant cell genome, particularly in the nuclear or plastid (e.g., chloroplast) genome. Preferred plant-expressible promoters include: the strong constitutive 35S promoters (the "35S promoters") of the cauliflower mosaic virus (CaMV) of isolates CM 1841 (Gardner et al., 1981), CabbB-S (Franck et al., 1980) and CabbB-JI (Hull and Howell, 1987); the 35S promoter described by Odell et al. (1985), promoters from the ubiquitin family (e.g., the maize ubiquitin promoter of Christensen et al., 1992, see also Cornejo et al., 1993), the gos2 promoter (de Pater et al., 1992), the emu promoter (Last et al., 1990), *Arabidopsis* actin promoters such as the promoter described by An et al. (1996), rice actin promoters such as the promoter described by Zhang et al. (1991); promoters of the Cassava vein mosaic virus (WO 97/48819, Verdaguer et al. (1998)), the pPLEX series of promoters from Subterranean Clover Stunt Virus (WO 96/06932), particularly the duplicated promoter region derived from the subterranean clover stunt virus genome segment 4 or 7 (referred to as the "S7S7" or "S4S4" promoters herein) described by Boevink et al. (1995) or Schünmann et al. (2003), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T-DNA (Velten et al., 1984). Alternatively, a promoter can be utilized which is not constitutive but rather is specific for one or more tissues or organs of the plant (e.g., leaves and/or roots) whereby the inserted cry gene part is expressed only in cells of the specific tissue(s) or organ(s). For example, the insecticidally effective cry gene part could be selectively expressed in the leaves of a plant (e.g., corn, cotton) by placing the insecticidally effective gene part under the control of a light-inducible promoter such as the promoter of the ribulose-1, 5-bisphosphate carboxylase small subunit gene of the plant itself or of another plant such as pea as disclosed in U.S. Pat. No. 5,254,799. Another alternative is to use a promoter whose expression is inducible, preferably by wounding such as insect feeding, e.g., the MPI promoter described by Cordera et al. (1994), or the *Agrobacterium* TR2' or mannopine synthase promoter (Velten et al., 1984) or a promoter inducible by chemical factors.

The insecticidally effective cry gene part is preferably inserted in the plant genome so that the inserted gene part is upstream (i.e., 5') of suitable 3' end transcription regulation signals (i.e., transcript formation and polyadenylation signals). This is preferably accomplished by inserting the cry1 chimeric gene in the plant cell genome. Preferred polyadenylation and transcript formation signals include those of the 3' untranslated region of the NADP-malic enzyme gene from *Flaveria bidentis* (Marshall et al., 1996), nopaline synthase gene (Depicker et al., 1982), the octopine synthase gene (Gielen et al., 1984) and the T-DNA gene 7 (Velten and Schell, 1985), which act as 3'-untranslated DNA sequences in transformed plant cells.

In one embodiment of this invention, at least one of the genes of the invention, preferably at least 2, are transformed into plants selected from the group consisting of: corn, cotton, watercress, horseradish, wasabi, arugula, cress, radish, canola, soybean, vegetable plants, Cruciferae plant species, Brassicaceae plant species such as cauliflower, cabbage, Chinese cabbage, turnip, mustard, oilseed rape, kale, broccoli, Brussels sprouts, mustard spinach, and the like. Particularly, in one embodiment of this invention the following *Brassica* species plants are protected from insects by the genes of this invention: *B. carinata, B. elongate, B. fruticulosa, B. juncea, B. napus, B. narinosa, B. hirta, B. rosularis, B. nigra, B. oleracea, B. perviridis, B. rapa, B. rupestris, B. septiceps, B. tournefortii*, and the like, particularly plants of the species *Brassica oleraceae* (such as the subspecies *botrytis* and *capitata*) or *Brassica napus*, as well as plants of the following genus: *Raphanus* (such as *R. sativus*), *Armoracia* (such as *A. rusticana*), *Wasabia* (such as *W. japonica*), *Eruca* (such as *E. vesicaria*), *Nastrurtium* (such as *N. officinale*), and *Lepidium* (such as *L. sativum*).

The invention includes the above listed *Brassica* species plants transformed with at least one or two genes of the invention, such as the cry1B and cry1C genes of the invention, as well as plants obtained after crossing or breeding with related plants (including plants of a related plant species) that contain the genes of the invention. Such crossing or breeding can be done using traditional breeding techniques known in the art, but may also include known in vitro work such as embryo rescue, protoplast fusion, and the like. The invention hence also relates to Brassicaceae plants such as *B. napus*, *B. rapa*, *B. juncea* or *B. carinata*, that contain the gene or genes of the invention, such as the cry1B and cry1C genes of the invention, from crossings with a transformed *B. oleracea* plant or the progeny thereof, or to *B. oleracea* plants that contain the gene or genes of the invention, such as the cry1B and cry1C genes of the invention, from crossings with a transformed *B. napus* plant, and to uses of such plants.

Transformation of plant cells can also be used to produce the proteins of the invention in large amounts in plant cell cultures, e.g., to produce a Cry1 protein that can then be applied onto crops after proper formulation. When reference to a transgenic plant cell is made herein, this refers to a plant cell (or also a plant protoplast) as such in isolation or in tissue culture, or to a plant cell (or protoplast) contained in a plant or in a differentiated organ or tissue, and both possibilities are specifically included herein. Hence, a reference to a plant cell in the description or claims is not meant to refer only to isolated cells in culture, but refers to any plant cell, wherever it may be located or in whatever type of plant tissue or organ it may be present.

All or part of the cry1 genes of the invention, encoding an anti-lepidopteran protein, can also be used to transform bacteria, such as a *B. thuringiensis* which has insecticidal activity against Lepidoptera or Coleoptera. Thereby, a transformed Bt strain can be produced which is useful for combating a wide spectrum of lepidopteran and coleopteran insect pests or for combating additional lepidopteran insect pests. Transformation of bacteria, such as bacteria of the genus *Pseudomonas*, *Agrobacterium*, *Bacillus* or *Escherichia*, with the cry1 genes of this invention, incorporated in a suitable cloning vehicle, can be carried out in a conventional manner, preferably using conventional electroporation techniques as described in Mahillon et al. (1989) and in PCT Patent publication WO 90/06999.

Transformed *Bacillus* species strains containing the cry gene of this invention can be fermented by conventional methods (Dulmage, 1981; Bernhard and Utz, 1993) to provide high yields of cells. Under appropriate conditions which are well understood (Dulmage, 1981), these strains each sporulate to produce crystal proteins containing the Cry protoxin in high yields.

An insecticidal, particularly anti-lepidopteran, composition of this invention can be formulated in a conventional manner using the microorganisms transformed with the cry gene, or preferably their respective Cry proteins or the Cry protoxin, toxin or insecticidally effective protoxin portion as an active ingredient, together with suitable carriers, diluents, emulsifiers and/or dispersants (e.g., as described by Bernhard and Utz, 1993). This Insecticide composition can be formulated as a wettable powder, pellets, granules or dust or as a liquid formulation with aqueous or non-aqueous solvents as a foam, gel, suspension, concentrate, etc.

A method for controlling insects, particularly Lepidoptera, in accordance with this invention can comprise applying (e.g., spraying), to a locus (area) to be protected, an insecticidal amount of the Cry proteins or host cells transformed with the cry gene of this invention. The locus to be protected can include, for example, the habitat of the insect pests or growing vegetation or an area where vegetation is to be grown.

In one embodiment of this invention, insects against which the cry1 genes or Cry1 proteins of the invention can be used include insects selected from the group consisting of: *Plutella xylostella*, *Spodoptera exigua*, *Spodoptera littoralis*, *Spodoptera frugiperda*, *Trichoplusia ni*, *Heliothis virescens*, *Mamestra brassicae*, *Pieris brassicae*, *Manduca sexta*, *Choristoneura fumiferana*, *Choristoneura occidentalis*, *Choristoneura rosaceana*, *Pandemis pyrusana*, *Platynota stultana*, *Lymantria dispar*, *Orgyia leucostigma*, *Malacosoma disstria*, *Lambina fiscellaria*, *Chilo suppressalis*, *Chilo partellus*, *Scirpophaga incertulas*, *Argyrotaenia citrana*, *Artogeia rape*, *Chrysomela scripta*, *Ostrinia nubilalis*, *Pseudoplusia includens*, and *Thaumetopoea pityocampa*. In one embodiment, *Plutella xylostella* (diamondback moth) is a preferred target insect pest. This is a cosmopolitan species that causes major losses in several Cruciferous plants, particularly Brassicacaea plants. The Cry1C, Cry1B and Cry1D proteins encoded by the genes of this invention are particularly useful to control this insect, e.g., by expression of the genes of the invention in cells of a plant.

Such insects can be controlled by planting or growing plants comprising any one of the cry1C genes of the invention in a field, or by securing the presence of a Cry1C protein as defined herein in or on plants infested by such insects (e.g., by sowing or planting a *Brassica* species plant such as a cabbage or cauliflower plant transformed with the cry1C1 or cry1C2 gene of this invention, or spraying a composition containing a Cry1C protein of this invention). The invention also relates to the use of the cry1 genes of this invention, at least the cry1C1 or cry1C2 genes, in plants to protect them against Lepidopteran insect pests, preferably in combination with a cry1B or cry1D gene of this invention.

In the current invention, also a modified coding sequence encoding a chloroplast transit peptide is provided. Such coding sequence has a codon usage adapted for high expression in plants, particularly Brassicaceae plants such as *Brassica oleracea* or *Brassica napus*, especially cabbage, cauliflower or oilseed rape (canola). In one embodiment of the invention, the modified transit peptide comprises the nucleotide sequence of SEQ ID No. 16 from nucleotide position 7 to nucleotide position 371, particularly the sequence of SEQ ID No. 16. Also plant cells, plants or seeds comprising the modified transit peptide coding sequence of the invention, as well as the use of this transit peptide coding sequence for targeting any protein to the chloroplast, particularly to the chloroplast of vegetable plants, particularly *Brassica* species plants, are included in this invention.

These and/or other embodiments of this invention are reflected in the wordings of the claims, that form part of the description of the invention.

The following Examples illustrate the invention, and are not provided to limit the invention or the protection sought. Unless otherwise stated, all recombinant DNA techniques are carried out according to standard protocols as described in Sambrook et al. (1989) Molecular Cloning: A Laboratory Manual, Second Edition, Cold Spring Harbour Laboratory Press, NY and in Volumes 1 and 2 of Ausubel et al. (1994) Current Protocols in Molecular Biology, Current Protocols, USA. Standard materials and methods for plant molecular work are described in Plant Molecular Biology Labfax (1993) by R. D. D. Croy published by BIOS Scientific Publications Ltd (UK) and Blackwell Scientific Publications, UK.

The enclosed sequence listing referred to in the Examples, the Claims and the Description is as follows:

SEQUENCE LISTING

SEQ ID No. 1: optimized cry1C1 coding sequence comprising an intron at position 672

SEQ ID No. 2: amino acid sequence of the Cry1C1 protein encoded by SEQ ID No. 1
SEQ ID No. 3: optimized cry1C2 coding sequence, comprising an intron at position 489
SEQ ID No. 4: optimized cry1C3 coding sequence, comprising the sequences of SEQ ID No. 1 and SEQ ID No. 16, encoding a fusion protein with a transit peptide
SEQ ID No. 5: Cry1C3 protein encoded by SEQ ID No. 4
SEQ ID No. 6: optimized cry1C4 coding sequence, comprising the sequences of SEQ ID No. 3 and SEQ ID No. 16, encoding a fusion protein with a transit peptide
SEQ ID No. 7: Cry1C4 protein encoded by SEQ ID No. 8
SEQ ID No. 8: optimized cry1B1 coding sequence, including a transit peptide coding sequence
SEQ ID No. 9: Cry1B1 protein encoded by the sequence of SEQ ID No. 8
SEQ ID No. 10: optimized cry1B2 coding sequence
SEQ ID No. 11. Cry1B2 protein encoded by the sequence of SEQ ID No. 10
SEQ ID No. 12: optimized cry1D1 coding sequence, including a transit peptide coding sequence
SEQ ID No. 13: Cry1D1 protein encoded by the sequence of SEQ ID No. 12
SEQ ID No. 14: optimized cry1D2 coding sequence
SEQ ID No. 15: Cry1D2 protein encoded by the sequence of SEQ ID No. 14
SEQ ID No. 16: coding sequence encoding an optimized chloroplast transit peptide
SEQ ID No. 17: chloroplast transit peptide encoded by the sequence of SEQ ID No. 16
SEQ ID No. 18: duplicated S7 subterranean clover stunt virus promoter sequence (S7S7)
SEQ ID No. 19: duplicated S4 subterranean clover stunt virus promoter sequence (S4S4)
SEQ ID No. 20: cry1B gene primer P1B227
SEQ ID No. 21: cry1B gene primer P1B228
SEQ ID No. 22: cry1C gene primer P1C247
SEQ ID No. 23: cry1C gene primer P1C252

EXAMPLES

1. Construction of Chimeric Genes and Transformation Vectors.

Several cry1 genes were designed and assembled using a combination of technologies to achieve genes with optimal performance in plant cells.

The cry1C1 DNA which was designed for optimal expression in plant cells is represented in SEQ ID No. 1. This DNA encodes the insecticidal Cry1C1 protein of the invention (SEQ ID No. 2). For transformation of plants, a first chimeric gene (the cry1C1 chimeric gene) is constructed comprising the following operably-linked elements (5' to 3'): a promoter comprising the duplicated promoter region derived from the subterranean clover stunt virus genome segment 7 (S7S7 promoter, Boevink et al., 1995, SEQ ID No. 18), the leader sequence of the tapetum-specific E1 gene (GE1) of Oryza sativa (Michiels et al., 1992), the cry1C1 DNA comprising the second intron of the light-inducible tissue-specific ST-LS1 gene of Solanum tuberosum (Eckes et al., 1986) at position 672 (SEQ ID No. 1), and the sequence including the 3' untranslated region of the NADP-malic enzyme gene from Flaveria bidentis (3' Me1, Marshall et al., 1996).

A similar cry1C chimeric gene was made, wherein the ST-LS1 intron 2 is at position 489 of the cry1C DNA (i.e., the cry1C2 DNA), this is the cry1C2 chimeric gene, otherwise constructed exactly like the cry1C1 chimeric gene.

To secure targeting of the Cry1C protein to the plant cell chloroplast, variants of the cry1C1 and cry1C2 chimeric genes are constructed which comprise a modified sequence encoding an optimized transit peptide (SEQ ID No. 16) as described by Lebrun et al. (1996) operably-linked to the cry1C coding region so that a transit peptide fusion protein is expressed in plant cells. These are the cry1C3 and cry1C4 chimeric genes, comprising the cry1C3 and cry1C4 coding sequences, respectively, which each contain the sequence of the modified chloroplast transit peptide of SEQ ID No. 16. The cry1C3 DNA sequence is shown in SEQ ID No. 4, it is a fusion of the cry1C1 sequence of SEQ ID No. 1 with the transit peptide coding sequence of SEQ ID No. 16. The cry1C4 DNA sequence is shown in SEQ ID No. 6, it is a fusion of the cry1C2 sequence of SEQ ID No. 3 with the transit peptide coding sequence of SEQ ID No. 16.

The cry1B1 DNA which was designed for optimal expression in plant cells is represented in SEQ ID No. 8. This DNA encodes the insecticidal Cry1B1 protein of the invention (SEQ ID No. 9). For transformation of plants, a chimeric gene (the cry1B1 chimeric gene) is constructed comprising the following operably-linked elements (5' to 3'): a promoter comprising the duplicated promoter region derived from the subterranean clover stunt virus genome segment 4 (S4S4 promoter, Boevink et al., 1995, SEQ ID No. 19), the leader sequence of the E1 gene (GE1) of Oryza sativa (Michiels et al., 1992), the cry1B1 DNA comprising the sequence of the modified chloroplast transit peptide of SEQ ID No. 16, and the sequence including the 3' untranslated region of the NADP-malic enzyme gene from Flaveria bidentis (3' Me1, Marshall et al., 1996).

A second form of the cry1B chimeric gene was also made, using the cry1B2 DNA (SEQ ID No. 10), wherein no sequence encoding an optimized transit peptide is contained, so that cytoplasmic accumulation of the Cry1B protein occurs in plant cells. This is the Cry1B2 chimeric gene.

The cry1D1 DNA which was designed for optimal expression in plant cells is represented in SEQ ID No. 12. This DNA encodes the insecticidal Cry1D1 protein of the invention (SEQ ID No. 13). For transformation of plants, a chimeric gene (the cry1D1 chimeric gene) is constructed comprising the following operably-linked elements (5' to 3'): an S4S4 promoter (SEQ ID No. 19), the leader sequence of the E1 gene (GE1) of Oryza sativa (Michiels et al., 1992), the cry1D1 DNA comprising the sequence of the modified chloroplast transit peptide of SEQ ID No. 16, and the sequence including the 3' untranslated region of the NADP-malic enzyme gene from Flaveria bidentis (3' Me1, Marshall et al., 1996).

A second form of the cry1D chimeric gene was also made, using the cry1D2 DNA, wherein no sequence encoding an optimized transit peptide is contained, so that cytoplasmic accumulation of the Cry1D protein occurs in plant cells. This is the Cry1D2 chimeric gene.

A DNA transformation vector (pT1C4B1) is made comprising between the T-DNA borders the cry1C4 chimeric gene and the cry1B1 chimeric gene in a head-to-tail orientation (3'Me1-cry1C4-GE1 leader-S7S7 S4S4-GE1 leader-cry1B1-3'Me1), as well as a transfer vector (pT1C2B2) comprising between the T-DNA borders the cry1C2 chimeric gene and the cry1B2 chimeric gene in a head-to-tail orientation (3'Me1-cry1 GE1 leader-S7S7-S4S4-GE1 leader-cry1B2-3'Me1). In such manner, with both T-DNA vectors, the cry1C and cry1B genes of the invention will be co-transferred to the plant cell and will be located at one locus after successful transformation.

Similar T-DNA vectors are constructed which contain the above cry1C chimeric genes but which contain as second chimeric gene the cry1D1 or cry1D2 chimeric genes instead of the above cry1B chimeric genes. Also a triple cry gene transformation vector is constructed, comprising both the cry1C, cry1D and cry1B genes (all either with or without modified transit peptide).

The transformation vectors containing the genes of the invention were derived from pGSC1700 (Cornelissen and Vandewiele, 1989). The vector backbone contains the following genetic elements:
a) the plasmid core comprising the origin of replication from the plasmid pBR322 (Bolivar et al., 1977) for replication in *Escherichia coli* and a restriction fragment comprising the origin of replication from the *Pseudomonas* plasmid pVS1 (Itoh et al., 1984) for replication in *Agrobacterium tumefaciens*.

b) a selectable marker gene conferring resistance to streptomycin and spectinomycin (aadA) for propagation and selection of the plasmid in *Escherichia coli* and *Agrobacterium tumefaciens*.

c) a DNA region consisting of a fragment of the neomycin phosphotransferase coding sequence of the npt1 gene from transposon Tn903 (Oka et al., 1981).

The T-DNA region of each transformation vector also contains a chimeric bar gene that serves as selectable marker gene. Expression of the bar gene enables the production of an enzyme, phosphinothricin-acetyl transferase, that metabolizes the herbicide glufosinate-ammonium, thus rendering it non-herbicidal in the plant. The chimeric bar gene comprises the 35S3 promoter region from the Cauliflower Mosaic Virus 35S transcript (Odell et al., 1985), the bar coding sequence of the phosphinothricin acetyltransferase gene of *Streptomyces hygroscopicus* as described by Thompson et al. (1987), and a 3' transcript termination and polyadenylation sequence from the 3' untranslated region of the nopaline synthase gene from the T-DNA of pTiT37 (Depicker et al., 1982).

Similar transformation vectors as those described are also constructed, wherein the cry1C1 or cry1C3 chimeric genes are used (similar as the above cry1C genes but having the ST-LS1 intron at a position 489). Also these vectors contain the cry1B1 or cry1B2 chimeric genes, or the cry1D1 or cry1C2 chimeric genes described above.

All constructed plasmids are confirmed to be accurate by restriction enzyme digest analysis and by DNA sequencing, before they are used for plant transformation.

2. Plant Transformation and Regeneration.

The above transformation vectors pT1C4B1 and pT1C2B2 containing the cry1C and cry1B genes of the invention are transferred into *Agrobacterium tumefaciens* strains for transformation in plants using routine methods.

Cauliflower and cabbage plants are transformed using *Agrobacterium* transformation. Seeds of *Brassica oleracea* var. *capitata* (cabbage) or *Brassica oleracea* var. *botrytis* (cauliflower) are sterilized by dipping in 70% ethanol followed by submersion in 6% bleach. The seeds are then rinsed with sterile water and transferred to small Petri-plates containing MS based medium. The Petri-plates are placed in glass containers and incubated for 5-8 days at 24° C. Hypocotyl explants of 0.5-0.7 cm are cut and placed in liquid medium with appropriate hormones. *Agrobacterium tumefaciens* carrying the genes of interest are added to the medium to make a final concentration of $1\times10^7$ bacteria/ml. After the co-cultivation period, the explants are washed in liquid medium with appropriate antibiotics and hormones and blotted dry on filter paper.

The explants are cultured for one week on callus induction medium with 5 mg/l silver nitrate and 250 mg/l of both Triacillin and Carbenicillin and 10 mg/l phosphinothricin for selection of transformation events.

Every two weeks explants are transferred to fresh medium. Every week explants are checked for callus formation. Calli are excised from the explants and transferred to shoot induction medium. Shoots are transferred to plastic containers with rooting medium.

Shoots are kept on this medium until they are normalized or rooted. If they are 3-10 cm in size and have a nicely developed root system, they are transferred to the greenhouse.

Oilseed rape plants are also transformed with the cry1C and cry1B genes using *Agrobacterium tumefaciens*. Hypocotyl explants of *Brassica napus* are used in routine transformation and regeneration methods, e.g., the method described by De Block et al. (1989).

3. Analysis of Transformants.

Once the transformed plants are regenerated, PCR and Southern analysis are used to confirm integration of the transgenes. Immunological analyses such as Cry1C- and Cry1B-specific ELISA assays or Western blots are used to select those transformed plants showing optimal expression levels of the Cry1C and Cry1B proteins.

RT-PCR experiments on RNA collected from cauliflower plants shown to be transformed with the cry1C genes of SEQ ID No. 1 or 3, comprising a plant intron at a different position, confirmed that splicing occurs correctly and that a functional Cry1C protein is produced in these plants. This is also confirmed by Northern blot analysis of these plants.

Also, insect assays using *Plutella xylostella* larvae under standard insect bio-assay conditions using proper controls with selected transformed cabbage, cauliflower and oilseed rape plants containing the Cry1C and Cry1B genes confirm the high insecticidal activity and the high dose of these protein expressed, in those transformed plants selected for optimal expression. Also, *Plutella xylostella* insects that have been selected for resistance to the Cry1C or Cry1B protein, are still effectively killed by the plants of the invention.

Progeny plants and seeds are also obtained from the transformed, selected plants of the invention, and the genes of the invention are shown to segregate in such progeny in the expected Mendelian fashion. Selection of the transgenic plants in the greenhouse and in the field at multiple locations will result in the identification of plant lines which have optimal stability and expression of the cry1 chimeric genes combined with optimal agronomical performance. Crossing of the selected best performing transgenic plants with several different commercial lines, and repeated backcrossing therewith, result in the presence of the (linked) cry1B and cry1C genes of the invention in different cabbage, cauliflower or oilseed rape genetic backgrounds, optimally adapted to different areas or climatic conditions.

Cited References

An et al. (1996) Plant J. 10, 107

Bernhard and Utz (1993) "Production of *Bacillus thuringiensis* insecticides for experimental and commercial uses", In *Bacillus thuringiensis*, An Environmental Biopesticide: Theory and Practice, pp. 255-267, eds.

Entwistle, P. F., Cory, J. S., Bailey, M. J. and Higgs, S., John Wiley and Sons, New York (1993).

Bih et al. (1999) J. Biol. Chem. 274, 22884-22894.

Boevink et al. (1995) Virology, 207, 354-361.

Bolivar et al. (1977) Gene, 2: 95-113.
Bradford et al. (1976) Anal. Biochem. 72, 248-254.
Brown (1986) Nucleic Acids Res. 1986 14, 9549-9559.
Brown and Simpson (1998) Ann. Rev. Plant Physiol. Plant Mol. Biol. 49, 77-95.
Brown et al. (1996) Plant Mol Biol. 32, 531-535.
Christensen et al. (1992) Plant Mol. Biol. 18, 675-689.
Christou et al. (1990). Trends Biotechnology 8, 145.
Cordera et al. (1994) The Plant Journal 6, 141.
Cornejo et al. (1993) Plant Mol. Biol. 23, 567-581.
Cornelissen & Vandewiele (1989) Nucleic Acids Research, 17: 19-25.
Cornelissen et al. (1986) EMBO J. 5, 37-40.
Crickmore et al. (1998) Microbiol. Mol. Biol Rev. 62(3), 807-13.
Datta et al. (1990) Bio/Technology 8, 736-740.
De Block et al. (1989) Plant Physiol., 91: 694.
De Pater et al., 1992, Plant J. 2, 834-844.
Depicker et al. (1982) Journal of Molecular and Applied Genetics, 1: 561-573.
Dulmage (1981), "Production of Bacteria for Biological Control of Insects" in
Biological Control in Crop Production, Ed. Paparizas, D. C., Osmun Publishers, Totowa, N.J., USA, pp. 129-141 (1981).
Eckes et al. (1986) Molecular and General Genetics, 205: 14-22.
Estruch et al., (1996), Proc Natl Acad Sci USA 93, 5389-94.
Ffrench-Constant and Bowen (2000) Cell Mol Life Sci 57, 828-33.
Franck et al. (1980) Cell 21, 285-294.
Fromm et al. (1990) Bio/Technology 8, 833-839.
Gardner et al. (1981) Nucleic Acids Research 9, 2871-2887.
Gielen et al. (1984) EMBO J 3, 835-845.
Gordon-Kamm et al. (1990) The Plant Cell 2, 603-618.
Hesse et al. (1989), EMBO J. 8 2453-2461,
Hinchee et al. (1988) Bio/Technology 6, 915.
Ho et al. (1989). Gene 77, 51-59.
Höfte et al. (1988) Appl. and Environm. Microbiol. 54, 2010-2017.
Höfte and Whiteley (1989) Microbiological Review 53, 242-255.
Hull and Howell (1987) Virology 86, 482-493.
Itoh et al. (1984) Plasmid, 11, 206-220.
Jansens et al. (1997) Crop Science 37, 1616-1624.
Keil et al. (1986), Nucl. Acids Res. 14, 5641-5650.
Klösgen et al. (1989), Mol. Gen. Genet. 217, 155-161.
Klösgen and Weil (1991), Mol. Gen. Genet. 225, 297-304.
Kota et al. (1999) Proc. Natl. Acad. Sci. USA 96, 1840-1845.
Last et al. (1990) Theor. Appl. Genet. 81, 581-588.
Lebrun et al. (1996) U.S. Pat. No. 5,510,471.
Lin et al. (2003) Bot. Bull. Acad. Sin. 44: 199-210.
Mahillon et al, FEMS Microbiol. Letters 60, 205-210 (1989).
Marshall et al. (1996) Plant Physiology, 111: 1251-1261
Michiels et al. (1992) published PCT application WO92/13956.
Morris et al. (1999), Biochem. Biophys. Res. Commun. 255, 328-333.
Needleman and Wunsch (1970) J. Mol. Biol., 48: 443-53.
Neuhaus & Rogers (1998), Plant Mol. Biol. 38, 127-144.
Odell et al. (1985) Nature, 313: 810-812.
Oelmuller et al., Mol. Gen. Genet. 237, 261-272 (1993).
Oka et al. (1981) Journal of Molecular Biology, 147: 217-226.
Park et al. (1997), J. Biol. Chem. 272, 6876-6881,
Rice et al. (2000) Trends in Genetics, 16: 276-277.
Schünmann et al. (2003) Functional Plant Biology 30, 453-460.
Shcherban et al. (1995) Proc. Natl. Acad. Sci USA 92, 9245-9249.
Shimamoto at al. (1989) Nature 338, 274-276.
Stanssens et al. (1989), Nucleic Acids Research 12, 4441-4454.
Sutliff et al. (1991) Plant Molec. Biol. 16, 579-591.
Tavladoraki et al. (1998), FEBS Lett. 426, 62-66.
Terashima et al. (1999), Appl. Microbiol. Biotechnol. 52, 516-523.
Thompson et al. (1987) The EMBO Journal, 6: 2519-2523.
Van Den Broeck et al., 1985, Nature 313, 358.
Van Rie et al. (1990) Science 247, 72.
Velten et al. (1984) J., EMBO J 3, 2723-2730.
Velten and Schell (1985) Nucleic Acids Research 13, 6981-6998.
Verdaguer at al. (1998) Plant Mol. Biol, 37, 1055-1067.
Waterfield et al. (2001) Trends Microbiol 9, 185-91.
White et al. (1989) Trends in Genet. 5, 185-189.
Wong et al. (1992) Plant Molec. Biol. 20, 81-93.
Zambryski (1988) Annual Review of Genetics, 22: 1-30.
Zhang et al. (1991) The Plant Cell 3, 1155-1165.
Zhao et al. (2003) Nature Biotechnology, 21: 1493-1497.

All cited references are hereby incorporated by reference into the description. The citation of any of these references is not to be construed as an acknowledgement of the accuracy of every statement contained in such reference, nor as an acknowledgment that such reference is relevant prior art or part of the common general knowledge in any territory.

The invention claimed is:

1. A chimeric gene comprising the following operably-linked sequences:
   (a) a coding region encoding a Cry1C protein comprising a DNA sequence with at least 98% sequence identity to the DNA of any one of SEQ ID Nos. 1, 3, 4 or 6, wherein said Cry1C protein is a protein comprising the amino acid sequence from the amino acid at position 29 to the amino acid at position 627 in SEQ ID No. 2, and
   (b) a promoter region capable of directing expression in plant cells.

2. The chimeric gene of claim 1, wherein said promoter comprises the sequence of SEQ ID No. 18 or 19.

3. The chimeric gene of claim 1, further comprising a 3' polyadenylation and transcript termination region.

4. A DNA comprising the chimeric gene of claim 1, further comprising a second chimeric gene comprising the following operably-linked sequences:
   (a) a second coding region encoding a Cry1B protein comprising a DNA sequence with at least 98% sequence identity to the DNA of SEQ ID No. 8 or 10, wherein said Cry1B protein is a protein comprising the amino acid sequence from the amino acid at position 31 to the amino acid at position 648 in SEQ ID No. 11, and
   (b) a second promoter region capable of directing expression in plant cells.

5. A DNA comprising the chimeric gene of claim 1, further comprising a second chimeric gene comprising the following operably-linked sequences:

(a) a coding region encoding a Cry1D protein comprising a DNA sequence with at least 98% sequence identity to the DNA of SEQ ID No. 12 or 14,
   wherein said Cry1D protein is a protein comprising the amino acid sequence from the amino acid at position 21 to the amino acid at position 604 in SEQ ID No. 15, and
(b) a promoter region capable of directing expression in plant cells.

6. The DNA of claim 4, wherein said second promoter region comprises the sequence of SEQ ID No. 18 or 19 and is different from said first promoter region.

7. A transgenic plant or seed, comprising the gene of claim 1 stably incorporated in its genome.

8. The plant or seed of claim 7, which is a *Brassica* species plant or plant cell.

9. The plant or seed of claim 8, wherein said plant is of the species *Brassica oleraceae, Brassica napus, Brassica raga, Brassica juncea* or *Brassica carinata*.

10. A method for controlling insects, comprising: planting or sowing in a field, plants comprising the chimeric gene of claim 1.

11. A transgenic plant or seed comprising the DNA of claim 4 stably incorporated in its genome.

12. The plant or seed of claim 11, wherein said plant is of the species *Brassica oleraceae, Brassica napus, Brassica rape, Brassica juncea,* or *Brassica carinata*.

* * * * *

SEQUENCE LISTING

```
<160> NUMBER OF SEQ ID NOS: 23

<210> SEQ ID NO 1
<211> LENGTH: 2076
<212> TYPE: DNA
<213> ORGANISM: Artificial Sequence
<220> FEATURE:
<223> OTHER INFORMATION: Optimized cry1C1 coding sequence
<220> FEATURE:
<221> NAME/KEY: CDS
<222> LOCATION: (1)..(672)
<220> FEATURE:
<221> NAME/KEY: Intron
<222> LOCATION: (673)..(861)
<220> FEATURE:
<221> NAME/KEY: CDS
```

<222> LOCATION: (862)..(2073)

<400> SEQUENCE: 1

| | | | | | | | | | | | | | | | | |
|---|---|---|---|---|---|---|---|---|---|---|---|---|---|---|---|---|
| atg | gct | gag | gag | aac | aac | cag | aac | cag | tgt | atc | cct | tac | aac | tgt | ctt | 48 |
| Met | Ala | Glu | Glu | Asn | Asn | Gln | Asn | Gln | Cys | Ile | Pro | Tyr | Asn | Cys | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| tcg | aac | cct | gag | gag | gtt | ctt | ctt | gat | gga | gag | aga | atc | tct | act | gga | 96 |
| Ser | Asn | Pro | Glu | Glu | Val | Leu | Leu | Asp | Gly | Glu | Arg | Ile | Ser | Thr | Gly | |
| | | 20 | | | | | 25 | | | | | 30 | | | | |

| | | | | | | | | | | | | | | | | |
|---|---|---|---|---|---|---|---|---|---|---|---|---|---|---|---|---|
| aac | tct | tct | atc | gat | att | tct | ctt | tct | ctt | gtt | cag | ttc | ctt | gtt | tct | 144 |
| Asn | Ser | Ser | Ile | Asp | Ile | Ser | Leu | Ser | Leu | Val | Gln | Phe | Leu | Val | Ser | |
| | | 35 | | | | | 40 | | | | | 45 | | | | |

| | | | | | | | | | | | | | | | | |
|---|---|---|---|---|---|---|---|---|---|---|---|---|---|---|---|---|
| aac | ttc | gtt | cct | gga | gga | gga | ttc | ctt | gtt | gga | ctt | atc | gat | ttc | gtt | 192 |
| Asn | Phe | Val | Pro | Gly | Gly | Gly | Phe | Leu | Val | Gly | Leu | Ile | Asp | Phe | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| tgg | gga | atc | gtt | gga | cct | tct | cag | tgg | gat | gct | ttc | ctt | gtt | cag | atc | 240 |
| Trp | Gly | Ile | Val | Gly | Pro | Ser | Gln | Trp | Asp | Ala | Phe | Leu | Val | Gln | Ile | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gag | cag | ctt | atc | aac | gag | aga | atc | gct | gag | ttc | gct | aga | aac | gct | gct | 288 |
| Glu | Gln | Leu | Ile | Asn | Glu | Arg | Ile | Ala | Glu | Phe | Ala | Arg | Asn | Ala | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| atc | gct | aac | ctt | gag | gga | ctt | gga | aac | aac | ttc | aac | atc | tac | gtt | gag | 336 |
| Ile | Ala | Asn | Leu | Glu | Gly | Leu | Gly | Asn | Asn | Phe | Asn | Ile | Tyr | Val | Glu | |
| | | | 100 | | | | | 105 | | | | | 110 | | | |

| | | | | | | | | | | | | | | | | |
|---|---|---|---|---|---|---|---|---|---|---|---|---|---|---|---|---|
| gct | ttc | aag | gag | tgg | gag | gag | gat | cct | aac | aac | cct | gag | act | aga | act | 384 |
| Ala | Phe | Lys | Glu | Trp | Glu | Glu | Asp | Pro | Asn | Asn | Pro | Glu | Thr | Arg | Thr | |
| | | | 115 | | | | | 120 | | | | | 125 | | | |

| | | | | | | | | | | | | | | | | |
|---|---|---|---|---|---|---|---|---|---|---|---|---|---|---|---|---|
| aga | gtt | atc | gat | aga | ttc | aga | atc | ctt | gat | gga | ctt | ctt | gag | aga | gat | 432 |
| Arg | Val | Ile | Asp | Arg | Phe | Arg | Ile | Leu | Asp | Gly | Leu | Leu | Glu | Arg | Asp | |
| | 130 | | | | | 135 | | | | | 140 | | | | | |

| | | | | | | | | | | | | | | | | |
|---|---|---|---|---|---|---|---|---|---|---|---|---|---|---|---|---|
| att | cct | tct | ttc | aga | atc | tct | gga | ttc | gag | gtt | cct | ctt | ctt | tct | gtt | 480 |
| Ile | Pro | Ser | Phe | Arg | Ile | Ser | Gly | Phe | Glu | Val | Pro | Leu | Leu | Ser | Val | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| tac | gct | cag | gct | gct | aac | ctt | cat | ctt | gct | atc | ctt | aga | gat | tct | gtt | 528 |
| Tyr | Ala | Gln | Ala | Ala | Asn | Leu | His | Leu | Ala | Ile | Leu | Arg | Asp | Ser | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| atc | ttc | gga | gag | aga | tgg | gga | ctt | act | act | atc | aac | gtt | aac | gag | aac | 576 |
| Ile | Phe | Gly | Glu | Arg | Trp | Gly | Leu | Thr | Thr | Ile | Asn | Val | Asn | Glu | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| tac | aac | aga | ctt | atc | aga | cat | atc | gat | gag | tac | gct | gat | cat | tgt | gct | 624 |
| Tyr | Asn | Arg | Leu | Ile | Arg | His | Ile | Asp | Glu | Tyr | Ala | Asp | His | Cys | Ala | |
| | | | 195 | | | | | 200 | | | | | 205 | | | |

| | | | | | | | | | | | | | | | | |
|---|---|---|---|---|---|---|---|---|---|---|---|---|---|---|---|---|
| aac | act | tac | aac | aga | gga | ctt | aac | aac | ctt | cct | aag | tct | act | tac | cag | 672 |
| Asn | Thr | Tyr | Asn | Arg | Gly | Leu | Asn | Asn | Leu | Pro | Lys | Ser | Thr | Tyr | Gln | |
| | 210 | | | | | 215 | | | | | 220 | | | | | |

| | | |
|---|---|---|
| gtaagtttct gcttctacct tgatatata tataataatt atcattaatt agtagtaata | 732 |
| taatatttca aatattttt tcaaaataaa agaatgtagt atatagcaat tgcttttctg | 792 |
| tagtttataa gtgtgtatat tttaatttat aactttctca atatatgacc aaaatttgtt | 852 |

| | | | | | | | | | | | | |
|---|---|---|---|---|---|---|---|---|---|---|---|---|
| gatgtgcag gac tgg atc act tac aac aga ctt aga aga gat ctt act ctt | | | | | | | | | | | | 903 |
| | Asp | Trp | Ile | Thr | Tyr | Asn | Arg | Leu | Arg | Arg | Asp | Leu | Thr | Leu |
| | | 225 | | | | | 230 | | | | | 235 | |

| | | | | | | | | | | | | | | | | |
|---|---|---|---|---|---|---|---|---|---|---|---|---|---|---|---|---|
| act | gtt | ctt | gat | att | gct | gct | ttc | ttc | cct | aac | tac | gat | aac | aga | aga | 951 |
| Thr | Val | Leu | Asp | Ile | Ala | Ala | Phe | Phe | Pro | Asn | Tyr | Asp | Asn | Arg | Arg | |
| | 240 | | | | | 245 | | | | | 250 | | | | | |

| | | | | | | | | | | | | | | | | |
|---|---|---|---|---|---|---|---|---|---|---|---|---|---|---|---|---|
| tac | cct | atc | cag | cct | gtt | gga | cag | ctt | act | aga | gag | gtt | tac | act | gat | 999 |
| Tyr | Pro | Ile | Gln | Pro | Val | Gly | Gln | Leu | Thr | Arg | Glu | Val | Tyr | Thr | Asp | |
| 255 | | | | | 260 | | | | | 265 | | | | | 270 | |

| | | | | | | | | | | | | | | | | |
|---|---|---|---|---|---|---|---|---|---|---|---|---|---|---|---|---|
| cct | ctt | atc | aac | ttc | aac | cct | cag | ctt | cag | tct | gtt | gct | cag | ctt | cct | 1047 |

-continued

```
                Pro Leu Ile Asn Phe Asn Pro Gln Leu Gln Ser Val Ala Gln Leu Pro
                                275                 280                 285 act ttc aac gtt atg gag tct tct gct atc aga aac cct cat ctt ttc          1095
Thr Phe Asn Val Met Glu Ser Ser Ala Ile Arg Asn Pro His Leu Phe
                290                 295                 300 gat att ctt aac aac ctt act atc ttc act gac tgg ttc tct gtt gga          1143
Asp Ile Leu Asn Asn Leu Thr Ile Phe Thr Asp Trp Phe Ser Val Gly
                305                 310                 315 aga aac ttc tac tgg gga gga cat aga gtt atc tct tct ctt atc gga          1191
Arg Asn Phe Tyr Trp Gly Gly His Arg Val Ile Ser Ser Leu Ile Gly
            320                 325                 330 gga gga aac atc act tct cct atc tac gga aga gag gct aac cag gag          1239
Gly Gly Asn Ile Thr Ser Pro Ile Tyr Gly Arg Glu Ala Asn Gln Glu
335                 340                 345                 350 cct cct aga tct ttc act ttc aac gga cct gtt ttc aga act ctt tct          1287
Pro Pro Arg Ser Phe Thr Phe Asn Gly Pro Val Phe Arg Thr Leu Ser
                355                 360                 365 aac cct act ctt aga ctt ctt cag cag cct tgg cct gct cct cct ttc          1335
Asn Pro Thr Leu Arg Leu Leu Gln Gln Pro Trp Pro Ala Pro Pro Phe
            370                 375                 380 aac ctt aga gga gtt gag gga gtt gag ttc tct act cct act aac tct          1383
Asn Leu Arg Gly Val Glu Gly Val Glu Phe Ser Thr Pro Thr Asn Ser
                385                 390                 395 ttc act tac aga gga aga gga act gtt gat tct ctt act gag ctt cct          1431
Phe Thr Tyr Arg Gly Arg Gly Thr Val Asp Ser Leu Thr Glu Leu Pro
            400                 405                 410 cct gag gat aac tct gtt cct cct aga gag gga tac tct cat aga ctt          1479
Pro Glu Asp Asn Ser Val Pro Pro Arg Glu Gly Tyr Ser His Arg Leu
415                 420                 425                 430 tgt cat gct act ttc gtt cag aga tct gga act cct ttc ctt act act          1527
Cys His Ala Thr Phe Val Gln Arg Ser Gly Thr Pro Phe Leu Thr Thr
                435                 440                 445 gga gtt gtt ttc tct tgg act cat aga tct gct act ctt act aac act          1575
Gly Val Val Phe Ser Trp Thr His Arg Ser Ala Thr Leu Thr Asn Thr
            450                 455                 460 atc gat cct gag agg atc aac cag atc cct ctt gtt aag gga ttc aga          1623
Ile Asp Pro Glu Arg Ile Asn Gln Ile Pro Leu Val Lys Gly Phe Arg
                465                 470                 475 gtt tgg gga gga act tct gtt atc act gga cct gga ttc act gga gga          1671
Val Trp Gly Gly Thr Ser Val Ile Thr Gly Pro Gly Phe Thr Gly Gly
            480                 485                 490 gat att ctt aga aga aac act ttc gga gat ttc gtt tct ctt cag gtt          1719
Asp Ile Leu Arg Arg Asn Thr Phe Gly Asp Phe Val Ser Leu Gln Val
495                 500                 505                 510 aac atc aac tct cct atc act cag aga tac aga ctt aga ttc aga tac          1767
Asn Ile Asn Ser Pro Ile Thr Gln Arg Tyr Arg Leu Arg Phe Arg Tyr
                515                 520                 525 gct tct tct aga gat gct aga gtt atc gtt ctt act gga gct gct tct          1815
Ala Ser Ser Arg Asp Ala Arg Val Ile Val Leu Thr Gly Ala Ala Ser
            530                 535                 540 act gga gtt gga gga cag gtt tct gtt aac atg cct ctt cag aag act          1863
Thr Gly Val Gly Gly Gln Val Ser Val Asn Met Pro Leu Gln Lys Thr
                545                 550                 555 atg gag atc gga gag aac ctt act tct aga act ttc aga tac act gat          1911
Met Glu Ile Gly Glu Asn Leu Thr Ser Arg Thr Phe Arg Tyr Thr Asp
            560                 565                 570 ttc tct aac cct ttc tct ttc aga gct aac cct gat att atc gga atc          1959
Phe Ser Asn Pro Phe Ser Phe Arg Ala Asn Pro Asp Ile Ile Gly Ile
575                 580                 585                 590
```

```
tct gag cag cct ctt ttc gga gct gga tct atc tct tct gga gag ctt    2007
Ser Glu Gln Pro Leu Phe Gly Ala Gly Ser Ile Ser Ser Gly Glu Leu
            595                 600                 605 tac atc gat aaa atc gag atc atc ctt gct gat gct act ttc gag gct    2055
Tyr Ile Asp Lys Ile Glu Ile Ile Leu Ala Asp Ala Thr Phe Glu Ala
            610                 615                 620 gag tct gat tta gag aga tga                                        2076
Glu Ser Asp Leu Glu Arg
            625
```

<210> SEQ ID NO 2
<211> LENGTH: 628
<212> TYPE: PRT
<213> ORGANISM: Artificial Sequence
<220> FEATURE:
<223> OTHER INFORMATION: CryC1 protein

<400> SEQUENCE: 2

```
Met Ala Glu Glu Asn Asn Gln Asn Gln Cys Ile Pro Tyr Asn Cys Leu
1               5                   10                  15

Ser Asn Pro Glu Glu Val Leu Leu Asp Gly Glu Arg Ile Ser Thr Gly
                20                  25                  30

Asn Ser Ser Ile Asp Ile Ser Leu Ser Leu Val Gln Phe Leu Val Ser
            35                  40                  45

Asn Phe Val Pro Gly Gly Gly Phe Leu Val Gly Leu Ile Asp Phe Val
        50                  55                  60

Trp Gly Ile Val Gly Pro Ser Gln Trp Asp Ala Phe Leu Val Gln Ile
65                  70                  75                  80

Glu Gln Leu Ile Asn Glu Arg Ile Ala Glu Phe Ala Arg Asn Ala Ala
                85                  90                  95

Ile Ala Asn Leu Glu Gly Leu Gly Asn Asn Phe Asn Ile Tyr Val Glu
            100                 105                 110

Ala Phe Lys Glu Trp Glu Glu Asp Pro Asn Asn Pro Glu Thr Arg Thr
        115                 120                 125

Arg Val Ile Asp Arg Phe Arg Ile Leu Asp Gly Leu Leu Glu Arg Asp
130                 135                 140

Ile Pro Ser Phe Arg Ile Ser Gly Phe Glu Val Pro Leu Leu Ser Val
145                 150                 155                 160

Tyr Ala Gln Ala Ala Asn Leu His Leu Ala Ile Leu Arg Asp Ser Val
                165                 170                 175

Ile Phe Gly Glu Arg Trp Gly Leu Thr Thr Ile Asn Val Asn Glu Asn
            180                 185                 190

Tyr Asn Arg Leu Ile Arg His Ile Asp Glu Tyr Ala Asp His Cys Ala
        195                 200                 205

Asn Thr Tyr Asn Arg Gly Leu Asn Asn Leu Pro Lys Ser Thr Tyr Gln
    210                 215                 220

Asp Trp Ile Thr Tyr Asn Arg Leu Arg Arg Asp Leu Thr Leu Thr Val
225                 230                 235                 240

Leu Asp Ile Ala Ala Phe Phe Pro Asn Tyr Asp Asn Arg Arg Tyr Pro
                245                 250                 255

Ile Gln Pro Val Gly Gln Leu Thr Arg Glu Val Tyr Thr Asp Pro Leu
            260                 265                 270

Ile Asn Phe Asn Pro Gln Leu Gln Ser Val Ala Gln Leu Pro Thr Phe
        275                 280                 285

Asn Val Met Glu Ser Ser Ala Ile Arg Asn Pro His Leu Phe Asp Ile
    290                 295                 300
```

```
Leu Asn Asn Leu Thr Ile Phe Thr Asp Trp Phe Ser Val Gly Arg Asn
305                 310                 315                 320

Phe Tyr Trp Gly Gly His Arg Val Ile Ser Ser Leu Ile Gly Gly Gly
            325                 330                 335

Asn Ile Thr Ser Pro Ile Tyr Gly Arg Glu Ala Asn Gln Glu Pro Pro
        340                 345                 350

Arg Ser Phe Thr Phe Asn Gly Pro Val Phe Arg Thr Leu Ser Asn Pro
    355                 360                 365

Thr Leu Arg Leu Leu Gln Gln Pro Trp Pro Ala Pro Pro Phe Asn Leu
370                 375                 380

Arg Gly Val Glu Gly Val Glu Phe Ser Thr Pro Thr Asn Ser Phe Thr
385                 390                 395                 400

Tyr Arg Gly Arg Gly Thr Val Asp Ser Leu Thr Glu Leu Pro Pro Glu
            405                 410                 415

Asp Asn Ser Val Pro Pro Arg Glu Gly Tyr Ser His Arg Leu Cys His
        420                 425                 430

Ala Thr Phe Val Gln Arg Ser Gly Thr Pro Phe Leu Thr Thr Gly Val
    435                 440                 445

Val Phe Ser Trp Thr His Arg Ser Ala Thr Leu Thr Asn Thr Ile Asp
450                 455                 460

Pro Glu Arg Ile Asn Gln Ile Pro Leu Val Lys Gly Phe Arg Val Trp
465                 470                 475                 480

Gly Gly Thr Ser Val Ile Thr Gly Pro Gly Phe Thr Gly Gly Asp Ile
            485                 490                 495

Leu Arg Arg Asn Thr Phe Gly Asp Phe Val Ser Leu Gln Val Asn Ile
        500                 505                 510

Asn Ser Pro Ile Thr Gln Arg Tyr Arg Leu Arg Phe Arg Tyr Ala Ser
    515                 520                 525

Ser Arg Asp Ala Arg Val Ile Val Leu Thr Gly Ala Ala Ser Thr Gly
530                 535                 540

Val Gly Gly Gln Val Ser Val Asn Met Pro Leu Gln Lys Thr Met Glu
545                 550                 555                 560

Ile Gly Glu Asn Leu Thr Ser Arg Thr Phe Arg Tyr Thr Asp Phe Ser
            565                 570                 575

Asn Pro Phe Ser Phe Arg Ala Asn Pro Asp Ile Ile Gly Ile Ser Glu
        580                 585                 590

Gln Pro Leu Phe Gly Ala Gly Ser Ile Ser Ser Gly Glu Leu Tyr Ile
    595                 600                 605

Asp Lys Ile Glu Ile Ile Leu Ala Asp Ala Thr Phe Glu Ala Glu Ser
610                 615                 620

Asp Leu Glu Arg
625

<210> SEQ ID NO 3
<211> LENGTH: 2076
<212> TYPE: DNA
<213> ORGANISM: Artificial Sequence
<220> FEATURE:
<223> OTHER INFORMATION: Optimized cry1C2 coding sequence
<220> FEATURE:
<221> NAME/KEY: exon
<222> LOCATION: (1)..(489)
<220> FEATURE:
<221> NAME/KEY: Intron
<222> LOCATION: (490)..(678)
<220> FEATURE:
<221> NAME/KEY: exon
<222> LOCATION: (679)..(2073)
```

-continued

<400> SEQUENCE: 3

```
atg gct gag gag aac aac cag aac cag tgt atc cct tac aac tgt ctt        48
Met Ala Glu Glu Asn Asn Gln Asn Gln Cys Ile Pro Tyr Asn Cys Leu
1               5                   10                  15 tcg aac cct gag gag gtt ctt ctt gat gga gag aga atc tct act gga        96
Ser Asn Pro Glu Glu Val Leu Leu Asp Gly Glu Arg Ile Ser Thr Gly
            20                  25                  30 aac tct tct atc gat att tct ctt tct ctt gtt cag ttc ctt gtt tct       144
Asn Ser Ser Ile Asp Ile Ser Leu Ser Leu Val Gln Phe Leu Val Ser
        35                  40                  45 aac ttc gtt cct gga gga gga ttc ctt gtt gga ctt atc gat ttc gtt       192
Asn Phe Val Pro Gly Gly Gly Phe Leu Val Gly Leu Ile Asp Phe Val
    50                  55                  60 tgg gga atc gtt gga cct tct cag tgg gat gct ttc ctt gtt cag atc       240
Trp Gly Ile Val Gly Pro Ser Gln Trp Asp Ala Phe Leu Val Gln Ile
65                  70                  75                  80 gag cag ctt atc aac gag aga atc gct gag ttc gct aga aac gct gct       288
Glu Gln Leu Ile Asn Glu Arg Ile Ala Glu Phe Ala Arg Asn Ala Ala
                85                  90                  95 atc gct aac ctt gag gga ctt gga aac aac ttc aac atc tac gtt gag       336
Ile Ala Asn Leu Glu Gly Leu Gly Asn Asn Phe Asn Ile Tyr Val Glu
            100                 105                 110 gct ttc aag gag tgg gag gag gat cct aac aac cct gag act aga act       384
Ala Phe Lys Glu Trp Glu Glu Asp Pro Asn Asn Pro Glu Thr Arg Thr
        115                 120                 125 aga gtt atc gat aga ttc aga atc ctt gat gga ctt ctt gag aga gat       432
Arg Val Ile Asp Arg Phe Arg Ile Leu Asp Gly Leu Leu Glu Arg Asp
    130                 135                 140 att cct tct ttc aga atc tct gga ttc gaa gtt cct ctt ctt tct gtt       480
Ile Pro Ser Phe Arg Ile Ser Gly Phe Glu Val Pro Leu Leu Ser Val
145                 150                 155                 160 tac gct cag gtaagtttct gcttctacct ttgatatata tataataatt               529
Tyr Ala Gln atcattaatt agtagtaata taatatttca aatatttttt tcaaaataaa agaatgtagt     589
atatagcaat tgcttttctg tagtttataa gtgtgtatat tttaatttat aacttttcta     649
atatatgacc aaaacatggt gatgtgcag gct gct aac ctt cat ctt gct atc       702
                                Ala Ala Asn Leu His Leu Ala Ile
                                165                 170 ctt aga gat tct gtt atc ttc gga gag aga tgg gga ctt act act atc       750
Leu Arg Asp Ser Val Ile Phe Gly Glu Arg Trp Gly Leu Thr Thr Ile
            175                 180                 185 aac gtt aac gag aac tac aac aga ctt atc aga cat atc gat gag tac       798
Asn Val Asn Glu Asn Tyr Asn Arg Leu Ile Arg His Ile Asp Glu Tyr
        190                 195                 200 gct gat cat tgt gct aac act tac aac aga gga ctt aac aac ctt cct       846
Ala Asp His Cys Ala Asn Thr Tyr Asn Arg Gly Leu Asn Asn Leu Pro
    205                 210                 215 aag tct act tac cag gac tgg atc act tac aac aga ctt aga aga gat       894
Lys Ser Thr Tyr Gln Asp Trp Ile Thr Tyr Asn Arg Leu Arg Arg Asp
220                 225                 230                 235 ctt act ctt act gtt ctt gat att gct gct ttc ttc cct aac tac gat       942
Leu Thr Leu Thr Val Leu Asp Ile Ala Ala Phe Phe Pro Asn Tyr Asp
            240                 245                 250 aac aga aga tac cct atc cag cct gtt gga cag ctt act aga gag gtt       990
Asn Arg Arg Tyr Pro Ile Gln Pro Val Gly Gln Leu Thr Arg Glu Val
        255                 260                 265 tac act gat cct ctt atc aac ttc aac cct cag ctt cag tct gtt gct      1038
Tyr Thr Asp Pro Leu Ile Asn Phe Asn Pro Gln Leu Gln Ser Val Ala
```

```
                Tyr Thr Asp Pro Leu Ile Asn Phe Asn Pro Gln Leu Gln Ser Val Ala
                            270                 275                 280 cag ctt cct act ttc aac gtt atg gag tct tct gct atc aga aac cct         1086
Gln Leu Pro Thr Phe Asn Val Met Glu Ser Ser Ala Ile Arg Asn Pro
285                 290                 295 cat ctt ttc gat att ctt aac aac ctt act atc ttc act gac tgg ttc         1134
His Leu Phe Asp Ile Leu Asn Asn Leu Thr Ile Phe Thr Asp Trp Phe
300                 305                 310                 315 tct gtt gga aga aac ttc tac tgg gga gga cat aga gtt atc tct tct         1182
Ser Val Gly Arg Asn Phe Tyr Trp Gly Gly His Arg Val Ile Ser Ser
                    320                 325                 330 ctt atc gga gga gga aac atc act tct cct atc tac gga aga gag gct         1230
Leu Ile Gly Gly Gly Asn Ile Thr Ser Pro Ile Tyr Gly Arg Glu Ala
                335                 340                 345 aac cag gag cct cct aga tct ttc act ttc aac gga cct gtt ttc aga         1278
Asn Gln Glu Pro Pro Arg Ser Phe Thr Phe Asn Gly Pro Val Phe Arg
            350                 355                 360 act ctt tct aac cct act ctt aga ctt ctt cag cag cct tgg cct gct         1326
Thr Leu Ser Asn Pro Thr Leu Arg Leu Leu Gln Gln Pro Trp Pro Ala
365                 370                 375 cct cct ttc aac ctt aga gga gtt gag gga gtt gag ttc tct act cct         1374
Pro Pro Phe Asn Leu Arg Gly Val Glu Gly Val Glu Phe Ser Thr Pro
380                 385                 390                 395 act aac tct ttc act tac aga gga aga gga act gtt gat tct ctt act         1422
Thr Asn Ser Phe Thr Tyr Arg Gly Arg Gly Thr Val Asp Ser Leu Thr
                    400                 405                 410 gag ctt cct cct gag gat aac tct gtt cct cct aga gag gga tac tct         1470
Glu Leu Pro Pro Glu Asp Asn Ser Val Pro Pro Arg Glu Gly Tyr Ser
                415                 420                 425 cat aga ctt tgt cat gct act ttc gtt cag aga tct gga act cct ttc         1518
His Arg Leu Cys His Ala Thr Phe Val Gln Arg Ser Gly Thr Pro Phe
            430                 435                 440 ctt act act gga gtt gtt ttc tct tgg act cat aga tct gct act ctt         1566
Leu Thr Thr Gly Val Val Phe Ser Trp Thr His Arg Ser Ala Thr Leu
445                 450                 455 act aac act atc gat cct gag agg atc aac cag atc cct ctt gtt aag         1614
Thr Asn Thr Ile Asp Pro Glu Arg Ile Asn Gln Ile Pro Leu Val Lys
460                 465                 470                 475 gga ttc aga gtt tgg gga gga act tct gtt atc act gga cct gga ttc         1662
Gly Phe Arg Val Trp Gly Gly Thr Ser Val Ile Thr Gly Pro Gly Phe
                    480                 485                 490 act gga gga gat att ctt aga aga aac act ttc gga gat ttc gtt tct         1710
Thr Gly Gly Asp Ile Leu Arg Arg Asn Thr Phe Gly Asp Phe Val Ser
                495                 500                 505 ctt cag gtt aac atc aac tct cct atc act cag aga tac aga ctt aga         1758
Leu Gln Val Asn Ile Asn Ser Pro Ile Thr Gln Arg Tyr Arg Leu Arg
            510                 515                 520 ttc aga tac gct tct tct aga gat gct aga gtt atc gtt ctt act gga         1806
Phe Arg Tyr Ala Ser Ser Arg Asp Ala Arg Val Ile Val Leu Thr Gly
525                 530                 535 gct gct tct act gga gtt gga gga cag gtt tct gtt aac atg cct ctt         1854
Ala Ala Ser Thr Gly Val Gly Gly Gln Val Ser Val Asn Met Pro Leu
540                 545                 550                 555 cag aag act atg gag atc gga gag aac ctt act tct aga act ttc aga         1902
Gln Lys Thr Met Glu Ile Gly Glu Asn Leu Thr Ser Arg Thr Phe Arg
                    560                 565                 570 tac act gat ttc tct aac cct ttc tct ttc aga gct aac cct gat att         1950
Tyr Thr Asp Phe Ser Asn Pro Phe Ser Phe Arg Ala Asn Pro Asp Ile
                575                 580                 585
```

-continued

```
atc gga atc tct gag cag cct ctt ttc gga gct gga tct atc tct tct    1998
Ile Gly Ile Ser Glu Gln Pro Leu Phe Gly Ala Gly Ser Ile Ser Ser
            590                 595                 600 gga gag ctt tac atc gat aaa atc gag atc atc ctt gct gat gct act    2046
Gly Glu Leu Tyr Ile Asp Lys Ile Glu Ile Ile Leu Ala Asp Ala Thr
605                 610                 615 ttc gag gct gag tct gat tta gag aga tga                            2076
Phe Glu Ala Glu Ser Asp Leu Glu Arg
620                 625
```

<210> SEQ ID NO 4
<211> LENGTH: 2442
<212> TYPE: DNA
<213> ORGANISM: Artificial Sequence
<220> FEATURE:
<223> OTHER INFORMATION: Optimized cry1C3 coding sequence
<220> FEATURE:
<221> NAME/KEY: CDS
<222> LOCATION: (1)..(1038)
<220> FEATURE:
<221> NAME/KEY: Intron
<222> LOCATION: (1039)..(1227)
<220> FEATURE:
<221> NAME/KEY: CDS
<222> LOCATION: (1228)..(2439)

<400> SEQUENCE: 4

```
atg gct tct atc tct tct tct gtt gct act gtt tct aga act gct cct    48
Met Ala Ser Ile Ser Ser Ser Val Ala Thr Val Ser Arg Thr Ala Pro
1               5                   10                  15 gct cag gct aac atg gtt gct cct ttc act gga ctt aag tct aac gct    96
Ala Gln Ala Asn Met Val Ala Pro Phe Thr Gly Leu Lys Ser Asn Ala
            20                  25                  30 gct ttc cct act act aag aag gct aac gat ttc tct act ctt cct tct   144
Ala Phe Pro Thr Thr Lys Lys Ala Asn Asp Phe Ser Thr Leu Pro Ser
        35                  40                  45 aac gga gga aga gtt cag tgt atg cag gtt tgg cct gct tac gga aac   192
Asn Gly Gly Arg Val Gln Cys Met Gln Val Trp Pro Ala Tyr Gly Asn
    50                  55                  60 aag aag ttc gag act ctt tct tac ctt cct cct ctt tct atg gct cct   240
Lys Lys Phe Glu Thr Leu Ser Tyr Leu Pro Pro Leu Ser Met Ala Pro
65                  70                  75                  80 act gtt atg atg gct tct tct gct act gct gtt gct cct ttc cag gga   288
Thr Val Met Met Ala Ser Ser Ala Thr Ala Val Ala Pro Phe Gln Gly
                85                  90                  95 ctt aag tct act gct tct ctt cct gtt gct aga aga tct tct aga tct   336
Leu Lys Ser Thr Ala Ser Leu Pro Val Ala Arg Arg Ser Ser Arg Ser
            100                 105                 110 ctt gga aac gtt tct aac gga gga aga atc aga tgt gag gag aac aac   384
Leu Gly Asn Val Ser Asn Gly Gly Arg Ile Arg Cys Glu Glu Asn Asn
        115                 120                 125 cag aac cag tgt atc cct tac aac tgt ctt tcg aac cct gag gag gtt   432
Gln Asn Gln Cys Ile Pro Tyr Asn Cys Leu Ser Asn Pro Glu Glu Val
    130                 135                 140 ctt ctt gat gga gag aga atc tct act gga aac tct tct atc gat att   480
Leu Leu Asp Gly Glu Arg Ile Ser Thr Gly Asn Ser Ser Ile Asp Ile
145                 150                 155                 160 tct ctt tct ctt gtt cag ttc ctt gtt tct aac ttc gtt cct gga gga   528
Ser Leu Ser Leu Val Gln Phe Leu Val Ser Asn Phe Val Pro Gly Gly
                165                 170                 175 gga ttc ctt gtt gga ctt atc gat ttc gtt tgg gga atc gtt gga cct   576
Gly Phe Leu Val Gly Leu Ile Asp Phe Val Trp Gly Ile Val Gly Pro
            180                 185                 190
```

| | |
|---|---:|
| tct cag tgg gat gct ttc ctt gtt cag atc gag cag ctt atc aac gag<br>Ser Gln Trp Asp Ala Phe Leu Val Gln Ile Glu Gln Leu Ile Asn Glu<br>195                    200                    205 | 624 |
| aga atc gct gag ttc gct aga aac gct gct atc gct aac ctt gag gga<br>Arg Ile Ala Glu Phe Ala Arg Asn Ala Ala Ile Ala Asn Leu Glu Gly<br>210                    215                    220 | 672 |
| ctt gga aac aac ttc aac atc tac gtt gag gct ttc aag gag tgg gag<br>Leu Gly Asn Asn Phe Asn Ile Tyr Val Glu Ala Phe Lys Glu Trp Glu<br>225                    230                    235                    240 | 720 |
| gag gat cct aac aac cct gag act aga act aga gtt atc gat aga ttc<br>Glu Asp Pro Asn Asn Pro Glu Thr Arg Thr Arg Val Ile Asp Arg Phe<br>                  245                    250                    255 | 768 |
| aga atc ctt gat gga ctt ctt gag aga gat att cct tct ttc aga atc<br>Arg Ile Leu Asp Gly Leu Leu Glu Arg Asp Ile Pro Ser Phe Arg Ile<br>260                    265                    270 | 816 |
| tct gga ttc gag gtt cct ctt ctt tct gtt tac gct cag gct gct aac<br>Ser Gly Phe Glu Val Pro Leu Leu Ser Val Tyr Ala Gln Ala Ala Asn<br>                  275                    280                    285 | 864 |
| ctt cat ctt gct atc ctt aga gat tct gtt atc ttc gga gag aga tgg<br>Leu His Leu Ala Ile Leu Arg Asp Ser Val Ile Phe Gly Glu Arg Trp<br>290                    295                    300 | 912 |
| gga ctt act act atc aac gtt aac gag aac tac aac aga ctt atc aga<br>Gly Leu Thr Thr Ile Asn Val Asn Glu Asn Tyr Asn Arg Leu Ile Arg<br>305                    310                    315                    320 | 960 |
| cat atc gat gag tac gct gat cat tgt gct aac act tac aac aga gga<br>His Ile Asp Glu Tyr Ala Asp His Cys Ala Asn Thr Tyr Asn Arg Gly<br>                  325                    330                    335 | 1008 |
| ctt aac aac ctt cct aag tct act tac cag gtaagtttct gcttctacct<br>Leu Asn Asn Leu Pro Lys Ser Thr Tyr Gln<br>340                    345 | 1058 |
| ttgatatata tataataatt atcattaatt agtagtaata taatatttca aatatttttt | 1118 |
| tcaaaataaa agaatgtagt atatagcaat tgcttttctg tagtttataa gtgtgtatat | 1178 |
| tttaatttat aactttttcta atatatgacc aaaattgtt gatgtgcag gac tgg atc<br>                                                              Asp Trp Ile | 1236 |
| act tac aac aga ctt aga aga gat ctt act ctt act gtt ctt gat att<br>Thr Tyr Asn Arg Leu Arg Arg Asp Leu Thr Leu Thr Val Leu Asp Ile<br>350                    355                    360                    365 | 1284 |
| gct gct ttc ttc cct aac tac gat aac aga aga tac cct atc cag cct<br>Ala Ala Phe Phe Pro Asn Tyr Asp Asn Arg Arg Tyr Pro Ile Gln Pro<br>                  370                    375                    380 | 1332 |
| gtt gga cag ctt act aga gag gtt tac act gat cct ctt atc aac ttc<br>Val Gly Gln Leu Thr Arg Glu Val Tyr Thr Asp Pro Leu Ile Asn Phe<br>                  385                    390                    395 | 1380 |
| aac cct cag ctt cag tct gtt gct cag ctt cct act ttc aac gtt atg<br>Asn Pro Gln Leu Gln Ser Val Ala Gln Leu Pro Thr Phe Asn Val Met<br>            400                    405                    410 | 1428 |
| gag tct tct gct atc aga aac cct cat ctt ttc gat att ctt aac aac<br>Glu Ser Ser Ala Ile Arg Asn Pro His Leu Phe Asp Ile Leu Asn Asn<br>415                    420                    425 | 1476 |
| ctt act atc ttc act gac tgg ttc tct gtt gga aga aac ttc tac tgg<br>Leu Thr Ile Phe Thr Asp Trp Phe Ser Val Gly Arg Asn Phe Tyr Trp<br>430                    435                    440                    445 | 1524 |
| gga gga cat aga gtt atc tct tct ctt atc gga gga aac atc act<br>Gly Gly His Arg Val Ile Ser Ser Leu Ile Gly Gly Asn Ile Thr<br>                  450                    455                    460 | 1572 |
| tct cct atc tac gga aga gag gct aac cag gag cct cct aga tct ttc<br>Ser Pro Ile Tyr Gly Arg Glu Ala Asn Gln Glu Pro Pro Arg Ser Phe<br>465                    470                    475 | 1620 |

```
act ttc aac gga cct gtt ttc aga act ctt tct aac cct act ctt aga    1668
Thr Phe Asn Gly Pro Val Phe Arg Thr Leu Ser Asn Pro Thr Leu Arg
            480                 485                 490 ctt ctt cag cag cct tgg cct gct cct cct ttc aac ctt aga gga gtt    1716
Leu Leu Gln Gln Pro Trp Pro Ala Pro Pro Phe Asn Leu Arg Gly Val
    495                 500                 505 gag gga gtt gag ttc tct act cct act aac tct ttc act tac aga gga    1764
Glu Gly Val Glu Phe Ser Thr Pro Thr Asn Ser Phe Thr Tyr Arg Gly
510                 515                 520                 525 aga gga act gtt gat tct ctt act gag ctt cct cct gag gat aac tct    1812
Arg Gly Thr Val Asp Ser Leu Thr Glu Leu Pro Pro Glu Asp Asn Ser
                530                 535                 540 gtt cct cct aga gag gga tac tct cat aga ctt tgt cat gct act ttc    1860
Val Pro Pro Arg Glu Gly Tyr Ser His Arg Leu Cys His Ala Thr Phe
            545                 550                 555 gtt cag aga tct gga act cct ttc ctt act act gga gtt gtt ttc tct    1908
Val Gln Arg Ser Gly Thr Pro Phe Leu Thr Thr Gly Val Val Phe Ser
    560                 565                 570 tgg act cat aga tct gct act ctt act aac act atc gat cct gag agg    1956
Trp Thr His Arg Ser Ala Thr Leu Thr Asn Thr Ile Asp Pro Glu Arg
575                 580                 585 atc aac cag atc cct ctt gtt aag gga ttc aga gtt tgg gga gga act    2004
Ile Asn Gln Ile Pro Leu Val Lys Gly Phe Arg Val Trp Gly Gly Thr
590                 595                 600                 605 tct gtt atc act gga cct gga ttc act gga gga gat att ctt aga aga    2052
Ser Val Ile Thr Gly Pro Gly Phe Thr Gly Gly Asp Ile Leu Arg Arg
            610                 615                 620 aac act ttc gga gat ttc gtt tct ctt cag gtt aac atc aac tct cct    2100
Asn Thr Phe Gly Asp Phe Val Ser Leu Gln Val Asn Ile Asn Ser Pro
    625                 630                 635 atc act cag aga tac aga ctt aga ttc aga tac gct tct tct aga gat    2148
Ile Thr Gln Arg Tyr Arg Leu Arg Phe Arg Tyr Ala Ser Ser Arg Asp
                640                 645                 650 gct aga gtt atc gtt ctt act gga gct gct tct act gga gtt gga gga    2196
Ala Arg Val Ile Val Leu Thr Gly Ala Ala Ser Thr Gly Val Gly Gly
            655                 660                 665 cag gtt tct gtt aac atg cct ctt cag aag act atg gag atc gga gag    2244
Gln Val Ser Val Asn Met Pro Leu Gln Lys Thr Met Glu Ile Gly Glu
670                 675                 680                 685 aac ctt act tct aga act ttc aga tac act gat ttc tct aac cct ttc    2292
Asn Leu Thr Ser Arg Thr Phe Arg Tyr Thr Asp Phe Ser Asn Pro Phe
            690                 695                 700 tct ttc aga gct aac cct gat att atc gga atc tct gag cag cct ctt    2340
Ser Phe Arg Ala Asn Pro Asp Ile Ile Gly Ile Ser Glu Gln Pro Leu
    705                 710                 715 ttc gga gct gga tct atc tct tct gga gag ctt tac atc gat aaa atc    2388
Phe Gly Ala Gly Ser Ile Ser Ser Gly Glu Leu Tyr Ile Asp Lys Ile
720                 725                 730 gag atc atc ctt gct gat gct act ttc gag gct gag tct gat tta gag    2436
Glu Ile Ile Leu Ala Asp Ala Thr Phe Glu Ala Glu Ser Asp Leu Glu
            735                 740                 745 aga tga                                                             2442
Arg
750

<210> SEQ ID NO 5
<211> LENGTH: 750
<212> TYPE: PRT
<213> ORGANISM: Artificial Sequence
<220> FEATURE:
<223> OTHER INFORMATION: Cry1C3 protein
```

-continued

<400> SEQUENCE: 5

```
Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
                100                 105                 110

Leu Gly Asn Val Ser Asn Gly Gly Arg Ile Arg Cys Glu Glu Asn Asn
                115                 120                 125

Gln Asn Gln Cys Ile Pro Tyr Asn Cys Leu Ser Asn Pro Glu Glu Val
    130                 135                 140

Leu Leu Asp Gly Glu Arg Ile Ser Thr Gly Asn Ser Ser Ile Asp Ile
145                 150                 155                 160

Ser Leu Ser Leu Val Gln Phe Leu Val Ser Asn Phe Val Pro Gly Gly
                165                 170                 175

Gly Phe Leu Val Gly Leu Ile Asp Phe Val Trp Gly Ile Val Gly Pro
                180                 185                 190

Ser Gln Trp Asp Ala Phe Leu Val Gln Ile Glu Gln Leu Ile Asn Glu
                195                 200                 205

Arg Ile Ala Glu Phe Ala Arg Asn Ala Ala Ile Ala Asn Leu Glu Gly
                210                 215                 220

Leu Gly Asn Asn Phe Asn Ile Tyr Val Glu Ala Phe Lys Glu Trp Glu
225                 230                 235                 240

Glu Asp Pro Asn Asn Pro Glu Thr Arg Thr Arg Val Ile Asp Arg Phe
                245                 250                 255

Arg Ile Leu Asp Gly Leu Leu Glu Arg Asp Ile Pro Ser Phe Arg Ile
                260                 265                 270

Ser Gly Phe Glu Val Pro Leu Leu Ser Val Tyr Ala Gln Ala Ala Asn
                275                 280                 285

Leu His Leu Ala Ile Leu Arg Asp Ser Val Ile Phe Gly Glu Arg Trp
                290                 295                 300

Gly Leu Thr Thr Ile Asn Val Asn Glu Asn Tyr Asn Arg Leu Ile Arg
305                 310                 315                 320

His Ile Asp Glu Tyr Ala Asp His Cys Ala Asn Thr Tyr Asn Arg Gly
                325                 330                 335

Leu Asn Asn Leu Pro Lys Ser Thr Tyr Gln Asp Trp Ile Thr Tyr Asn
                340                 345                 350

Arg Leu Arg Arg Asp Leu Thr Leu Thr Val Leu Asp Ile Ala Ala Phe
                355                 360                 365

Phe Pro Asn Tyr Asp Asn Arg Arg Tyr Pro Ile Gln Pro Val Gly Gln
                370                 375                 380

Leu Thr Arg Glu Val Tyr Thr Asp Pro Leu Ile Asn Phe Asn Pro Gln
385                 390                 395                 400

Leu Gln Ser Val Ala Gln Leu Pro Thr Phe Asn Val Met Glu Ser Ser
```

```
                    405                 410                 415
Ala Ile Arg Asn Pro His Leu Phe Asp Ile Leu Asn Asn Leu Thr Ile
            420                 425                 430

Phe Thr Asp Trp Phe Ser Val Gly Arg Asn Phe Tyr Trp Gly Gly His
        435                 440                 445

Arg Val Ile Ser Ser Leu Ile Gly Gly Asn Ile Thr Ser Pro Ile
    450                 455                 460

Tyr Gly Arg Glu Ala Asn Gln Glu Pro Pro Arg Ser Phe Thr Phe Asn
465                 470                 475                 480

Gly Pro Val Phe Arg Thr Leu Ser Asn Pro Thr Leu Arg Leu Leu Gln
                485                 490                 495

Gln Pro Trp Pro Ala Pro Pro Phe Asn Leu Arg Gly Val Glu Gly Val
            500                 505                 510

Glu Phe Ser Thr Pro Thr Asn Ser Phe Thr Tyr Arg Gly Arg Gly Thr
        515                 520                 525

Val Asp Ser Leu Thr Glu Leu Pro Pro Glu Asp Asn Ser Val Pro Pro
    530                 535                 540

Arg Glu Gly Tyr Ser His Arg Leu Cys His Ala Thr Phe Val Gln Arg
545                 550                 555                 560

Ser Gly Thr Pro Phe Leu Thr Thr Gly Val Val Phe Ser Trp Thr His
                565                 570                 575

Arg Ser Ala Thr Leu Thr Asn Thr Ile Asp Pro Glu Arg Ile Asn Gln
            580                 585                 590

Ile Pro Leu Val Lys Gly Phe Arg Val Trp Gly Gly Thr Ser Val Ile
        595                 600                 605

Thr Gly Pro Gly Phe Thr Gly Gly Asp Ile Leu Arg Arg Asn Thr Phe
    610                 615                 620

Gly Asp Phe Val Ser Leu Gln Val Asn Ile Asn Ser Pro Ile Thr Gln
625                 630                 635                 640

Arg Tyr Arg Leu Arg Phe Arg Tyr Ala Ser Ser Arg Asp Ala Arg Val
                645                 650                 655

Ile Val Leu Thr Gly Ala Ala Ser Thr Gly Val Gly Gly Gln Val Ser
            660                 665                 670

Val Asn Met Pro Leu Gln Lys Thr Met Glu Ile Gly Glu Asn Leu Thr
        675                 680                 685

Ser Arg Thr Phe Arg Tyr Thr Asp Phe Ser Asn Pro Phe Ser Phe Arg
    690                 695                 700

Ala Asn Pro Asp Ile Ile Gly Ile Ser Glu Gln Pro Leu Phe Gly Ala
705                 710                 715                 720

Gly Ser Ile Ser Ser Gly Glu Leu Tyr Ile Asp Lys Ile Glu Ile Ile
                725                 730                 735

Leu Ala Asp Ala Thr Phe Glu Ala Glu Ser Asp Leu Glu Arg
            740                 745                 750

<210> SEQ ID NO 6
<211> LENGTH: 2442
<212> TYPE: DNA
<213> ORGANISM: Artificial Sequence
<220> FEATURE:
<223> OTHER INFORMATION: Optimized cry1C4 coding sequence
<220> FEATURE:
<221> NAME/KEY: CDS
<222> LOCATION: (1)..(855)
<220> FEATURE:
<221> NAME/KEY: Intron
<222> LOCATION: (856)..(1044)
<220> FEATURE:
```

<220> NAME/KEY: CDS
<222> LOCATION: (1045)..(2439)

<400> SEQUENCE: 6

```
atg gct tct atc tct tct tct gtt gct act gtt tct aga act gct cct      48
Met Ala Ser Ile Ser Ser Ser Val Ala Thr Val Ser Arg Thr Ala Pro
1               5                   10                  15 gct cag gct aac atg gtt gct cct ttc act gga ctt aag tct aac gct      96
Ala Gln Ala Asn Met Val Ala Pro Phe Thr Gly Leu Lys Ser Asn Ala
            20                  25                  30 gct ttc cct act act aag aag gct aac gat ttc tct act ctt cct tct     144
Ala Phe Pro Thr Thr Lys Lys Ala Asn Asp Phe Ser Thr Leu Pro Ser
        35                  40                  45 aac gga gga aga gtt cag tgt atg cag gtt tgg cct gct tac gga aac     192
Asn Gly Gly Arg Val Gln Cys Met Gln Val Trp Pro Ala Tyr Gly Asn
    50                  55                  60 aag aag ttc gag act ctt tct tac ctt cct cct ctt tct atg gct cct     240
Lys Lys Phe Glu Thr Leu Ser Tyr Leu Pro Pro Leu Ser Met Ala Pro
65                  70                  75                  80 act gtt atg atg gct tct tct gct act gct gtt gct cct ttc cag gga     288
Thr Val Met Met Ala Ser Ser Ala Thr Ala Val Ala Pro Phe Gln Gly
                85                  90                  95 ctt aag tct act gct tct ctt cct gtt gct aga aga tct tct aga tct     336
Leu Lys Ser Thr Ala Ser Leu Pro Val Ala Arg Arg Ser Ser Arg Ser
            100                 105                 110 ctt gga aac gtt tct aac gga gga aga atc aga tgt gag gag aac aac     384
Leu Gly Asn Val Ser Asn Gly Gly Arg Ile Arg Cys Glu Glu Asn Asn
        115                 120                 125 cag aac cag tgt atc cct tac aac tgt ctt tcg aac cct gag gag gtt     432
Gln Asn Gln Cys Ile Pro Tyr Asn Cys Leu Ser Asn Pro Glu Glu Val
    130                 135                 140 ctt ctt gat gga gag aga atc tct act gga aac tct tct atc gat att     480
Leu Leu Asp Gly Glu Arg Ile Ser Thr Gly Asn Ser Ser Ile Asp Ile
145                 150                 155                 160 tct ctt tct ctt gtt cag ttc ctt gtt tct aac ttc gtt cct gga gga     528
Ser Leu Ser Leu Val Gln Phe Leu Val Ser Asn Phe Val Pro Gly Gly
                165                 170                 175 gga ttc ctt gtt gga ctt atc gat ttc gtt tgg gga atc gtt gga cct     576
Gly Phe Leu Val Gly Leu Ile Asp Phe Val Trp Gly Ile Val Gly Pro
            180                 185                 190 tct cag tgg gat gct ttc ctt gtt cag atc gag cag ctt atc aac gag     624
Ser Gln Trp Asp Ala Phe Leu Val Gln Ile Glu Gln Leu Ile Asn Glu
        195                 200                 205 aga atc gct gag ttc gct aga aac gct gct atc gct aac ctt gag gga     672
Arg Ile Ala Glu Phe Ala Arg Asn Ala Ala Ile Ala Asn Leu Glu Gly
    210                 215                 220 ctt gga aac aac ttc aac atc tac gtt gag gct ttc aag gag tgg gag     720
Leu Gly Asn Asn Phe Asn Ile Tyr Val Glu Ala Phe Lys Glu Trp Glu
225                 230                 235                 240 gag gat cct aac aac cct gag act aga act aga gtt atc gat aga ttc     768
Glu Asp Pro Asn Asn Pro Glu Thr Arg Thr Arg Val Ile Asp Arg Phe
                245                 250                 255 aga atc ctt gat gga ctt ctt gag aga gat att cct tct ttc aga atc     816
Arg Ile Leu Asp Gly Leu Leu Glu Arg Asp Ile Pro Ser Phe Arg Ile
            260                 265                 270 tct gga ttc gaa gtt cct ctt ctt tct gtt tac gct cag gtaagtttct      865
Ser Gly Phe Glu Val Pro Leu Leu Ser Val Tyr Ala Gln
        275                 280                 285 gcttctacct ttgatatata tataataatt atcattaatt agtagtaata taatatttca   925
```

-continued

```
aatatttttt tcaaaataaa agaatgtagt atatagcaat tgcttttctg tagtttataa    985
gtgtgtatat tttaatttat aacttttcta atatatgacc aaaacatggt gatgtgcag   1044
```

| | | | | | | | | | | | | | | | | |
|---|---|---|---|---|---|---|---|---|---|---|---|---|---|---|---|---|
| gct | gct | aac | ctt | cat | ctt | gct | atc | ctt | aga | gat | tct | gtt | atc | ttc | gga | 1092 |
| Ala | Ala | Asn | Leu | His | Leu | Ala | Ile | Leu | Arg | Asp | Ser | Val | Ile | Phe | Gly | |
| | | | 290 | | | | 295 | | | | | 300 | | | | |
| gag | aga | tgg | gga | ctt | act | act | atc | aac | gtt | aac | gag | aac | tac | aac | aga | 1140 |
| Glu | Arg | Trp | Gly | Leu | Thr | Thr | Ile | Asn | Val | Asn | Glu | Asn | Tyr | Asn | Arg | |
| | | | 305 | | | | | 310 | | | | | 315 | | | |
| ctt | atc | aga | cat | atc | gat | gag | tac | gct | gat | cat | tgt | gct | aac | act | tac | 1188 |
| Leu | Ile | Arg | His | Ile | Asp | Glu | Tyr | Ala | Asp | His | Cys | Ala | Asn | Thr | Tyr | |
| | | 320 | | | | | 325 | | | | | 330 | | | | |
| aac | aga | gga | ctt | aac | aac | ctt | cct | aag | tct | act | tac | cag | gac | tgg | atc | 1236 |
| Asn | Arg | Gly | Leu | Asn | Asn | Leu | Pro | Lys | Ser | Thr | Tyr | Gln | Asp | Trp | Ile | |
| | | 335 | | | | | 340 | | | | | 345 | | | | |
| act | tac | aac | aga | ctt | aga | aga | gat | ctt | act | ctt | act | gtt | ctt | gat | att | 1284 |
| Thr | Tyr | Asn | Arg | Leu | Arg | Arg | Asp | Leu | Thr | Leu | Thr | Val | Leu | Asp | Ile | |
| 350 | | | | | 355 | | | | | 360 | | | | | 365 | |
| gct | gct | ttc | ttc | cct | aac | tac | gat | aac | aga | aga | tac | cct | atc | cag | cct | 1332 |
| Ala | Ala | Phe | Phe | Pro | Asn | Tyr | Asp | Asn | Arg | Arg | Tyr | Pro | Ile | Gln | Pro | |
| | | | | 370 | | | | | 375 | | | | | 380 | | |
| gtt | gga | cag | ctt | act | aga | gag | gtt | tac | act | gat | cct | ctt | atc | aac | ttc | 1380 |
| Val | Gly | Gln | Leu | Thr | Arg | Glu | Val | Tyr | Thr | Asp | Pro | Leu | Ile | Asn | Phe | |
| | | | 385 | | | | | 390 | | | | | 395 | | | |
| aac | cct | cag | ctt | cag | tct | gtt | gct | cag | ctt | cct | act | ttc | aac | gtt | atg | 1428 |
| Asn | Pro | Gln | Leu | Gln | Ser | Val | Ala | Gln | Leu | Pro | Thr | Phe | Asn | Val | Met | |
| | | 400 | | | | | 405 | | | | | 410 | | | | |
| gag | tct | tct | gct | atc | aga | aac | cct | cat | ctt | ttc | gat | att | ctt | aac | aac | 1476 |
| Glu | Ser | Ser | Ala | Ile | Arg | Asn | Pro | His | Leu | Phe | Asp | Ile | Leu | Asn | Asn | |
| | 415 | | | | | 420 | | | | | 425 | | | | | |
| ctt | act | atc | ttc | act | gac | tgg | ttc | tct | gtt | gga | aga | aac | ttc | tac | tgg | 1524 |
| Leu | Thr | Ile | Phe | Thr | Asp | Trp | Phe | Ser | Val | Gly | Arg | Asn | Phe | Tyr | Trp | |
| 430 | | | | | 435 | | | | | 440 | | | | | 445 | |
| gga | gga | cat | aga | gtt | atc | tct | tct | ctt | atc | gga | gga | gga | aac | atc | act | 1572 |
| Gly | Gly | His | Arg | Val | Ile | Ser | Ser | Leu | Ile | Gly | Gly | Gly | Asn | Ile | Thr | |
| | | | 450 | | | | | 455 | | | | | 460 | | | |
| tct | cct | atc | tac | gga | aga | gag | gct | aac | cag | gag | cct | cct | aga | tct | ttc | 1620 |
| Ser | Pro | Ile | Tyr | Gly | Arg | Glu | Ala | Asn | Gln | Glu | Pro | Pro | Arg | Ser | Phe | |
| | | | 465 | | | | | 470 | | | | | 475 | | | |
| act | ttc | aac | gga | cct | gtt | ttc | aga | act | ctt | tct | aac | cct | act | ctt | aga | 1668 |
| Thr | Phe | Asn | Gly | Pro | Val | Phe | Arg | Thr | Leu | Ser | Asn | Pro | Thr | Leu | Arg | |
| | | 480 | | | | | 485 | | | | | 490 | | | | |
| ctt | ctt | cag | cag | cct | tgg | cct | gct | cct | cct | ttc | aac | ctt | aga | gga | gtt | 1716 |
| Leu | Leu | Gln | Gln | Pro | Trp | Pro | Ala | Pro | Pro | Phe | Asn | Leu | Arg | Gly | Val | |
| | | 495 | | | | | 500 | | | | | 505 | | | | |
| gag | gga | gtt | gag | ttc | tct | act | cct | act | aac | tct | ttc | act | tac | aga | gga | 1764 |
| Glu | Gly | Val | Glu | Phe | Ser | Thr | Pro | Thr | Asn | Ser | Phe | Thr | Tyr | Arg | Gly | |
| 510 | | | | | 515 | | | | | 520 | | | | | 525 | |
| aga | gga | act | gtt | gat | tct | ctt | act | gag | ctt | cct | cct | gag | gat | aac | tct | 1812 |
| Arg | Gly | Thr | Val | Asp | Ser | Leu | Thr | Glu | Leu | Pro | Pro | Glu | Asp | Asn | Ser | |
| | | | | 530 | | | | | 535 | | | | | 540 | | |
| gtt | cct | cct | aga | gag | gga | tac | tct | cat | aga | ctt | tgt | cat | gct | act | ttc | 1860 |
| Val | Pro | Pro | Arg | Glu | Gly | Tyr | Ser | His | Arg | Leu | Cys | His | Ala | Thr | Phe | |
| | | | 545 | | | | | 550 | | | | | 555 | | | |
| gtt | cag | aga | tct | gga | act | cct | ttc | ctt | act | act | gga | gtt | gtt | ttc | tct | 1908 |
| Val | Gln | Arg | Ser | Gly | Thr | Pro | Phe | Leu | Thr | Thr | Gly | Val | Val | Phe | Ser | |
| | | 560 | | | | | 565 | | | | | 570 | | | | |
| tgg | act | cat | aga | tct | gct | act | ctt | act | aac | act | atc | gat | cct | gag | agg | 1956 |
| Trp | Thr | His | Arg | Ser | Ala | Thr | Leu | Thr | Asn | Thr | Ile | Asp | Pro | Glu | Arg | |
| | | | 575 | | | | | 580 | | | | | 585 | | | |

```
atc aac cag atc cct ctt gtt aag gga ttc aga gtt tgg gga gga act      2004
Ile Asn Gln Ile Pro Leu Val Lys Gly Phe Arg Val Trp Gly Gly Thr
590                 595                 600                 605 tct gtt atc act gga cct gga ttc act gga gga gat att ctt aga aga      2052
Ser Val Ile Thr Gly Pro Gly Phe Thr Gly Gly Asp Ile Leu Arg Arg
            610                 615                 620 aac act ttc gga gat ttc gtt tct ctt cag gtt aac atc aac tct cct      2100
Asn Thr Phe Gly Asp Phe Val Ser Leu Gln Val Asn Ile Asn Ser Pro
        625                 630                 635 atc act cag aga tac aga ctt aga ttc aga tac gct tct tct aga gat      2148
Ile Thr Gln Arg Tyr Arg Leu Arg Phe Arg Tyr Ala Ser Ser Arg Asp
    640                 645                 650 gct aga gtt atc gtt ctt act gga gct gct tct act gga gtt gga gga      2196
Ala Arg Val Ile Val Leu Thr Gly Ala Ala Ser Thr Gly Val Gly Gly
655                 660                 665 cag gtt tct gtt aac atg cct ctt cag aag act atg gag atc gga gag      2244
Gln Val Ser Val Asn Met Pro Leu Gln Lys Thr Met Glu Ile Gly Glu
670                 675                 680                 685 aac ctt act tct aga act ttc aga tac act gat ttc tct aac cct ttc      2292
Asn Leu Thr Ser Arg Thr Phe Arg Tyr Thr Asp Phe Ser Asn Pro Phe
            690                 695                 700 tct ttc aga gct aac cct gat att atc gga atc tct gag cag cct ctt      2340
Ser Phe Arg Ala Asn Pro Asp Ile Ile Gly Ile Ser Glu Gln Pro Leu
        705                 710                 715 ttc gga gct gga tct atc tct tct gga gag ctt tac atc gat aaa atc      2388
Phe Gly Ala Gly Ser Ile Ser Ser Gly Glu Leu Tyr Ile Asp Lys Ile
    720                 725                 730 gag atc atc ctt gct gat gct act ttc gag gct gag tct gat tta gag      2436
Glu Ile Ile Leu Ala Asp Ala Thr Phe Glu Ala Glu Ser Asp Leu Glu
735                 740                 745 aga tga                                                              2442
Arg
750

<210> SEQ ID NO 7
<211> LENGTH: 750
<212> TYPE: PRT
<213> ORGANISM: Artificial Sequence
<220> FEATURE:
<223> OTHER INFORMATION: Cry1C4 protein

<400> SEQUENCE: 7

Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
                20                  25                  30

Ala Phe Pro Thr Thr Lys Lys Ala Asn Asp Phe Ser Thr Leu Pro Ser
            35                  40                  45

Asn Gly Gly Arg Val Gln Cys Met Gln Val Trp Pro Ala Tyr Gly Asn
        50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys Glu Glu Asn Asn
        115                 120                 125
```

```
Gln Asn Gln Cys Ile Pro Tyr Asn Cys Leu Ser Asn Pro Glu Glu Val
130                 135                 140

Leu Leu Asp Gly Glu Arg Ile Ser Thr Gly Asn Ser Ser Ile Asp Ile
145                 150                 155                 160

Ser Leu Ser Leu Val Gln Phe Leu Val Ser Asn Phe Val Pro Gly Gly
                165                 170                 175

Gly Phe Leu Val Gly Leu Ile Asp Phe Val Trp Gly Ile Val Gly Pro
                180                 185                 190

Ser Gln Trp Asp Ala Phe Leu Val Gln Ile Glu Gln Leu Ile Asn Glu
            195                 200                 205

Arg Ile Ala Glu Phe Ala Arg Asn Ala Ala Ile Ala Asn Leu Glu Gly
210                 215                 220

Leu Gly Asn Asn Phe Asn Ile Tyr Val Glu Ala Phe Lys Glu Trp Glu
225                 230                 235                 240

Glu Asp Pro Asn Asn Pro Glu Thr Arg Thr Arg Val Ile Asp Arg Phe
                245                 250                 255

Arg Ile Leu Asp Gly Leu Leu Glu Arg Asp Ile Pro Ser Phe Arg Ile
                260                 265                 270

Ser Gly Phe Glu Val Pro Leu Leu Ser Val Tyr Ala Gln Ala Ala Asn
            275                 280                 285

Leu His Leu Ala Ile Leu Arg Asp Ser Val Ile Phe Gly Glu Arg Trp
290                 295                 300

Gly Leu Thr Thr Ile Asn Val Asn Glu Asn Tyr Asn Arg Leu Ile Arg
305                 310                 315                 320

His Ile Asp Glu Tyr Ala Asp His Cys Ala Asn Thr Tyr Asn Arg Gly
                325                 330                 335

Leu Asn Asn Leu Pro Lys Ser Thr Tyr Gln Asp Trp Ile Thr Tyr Asn
                340                 345                 350

Arg Leu Arg Arg Asp Leu Thr Leu Thr Val Leu Asp Ile Ala Ala Phe
            355                 360                 365

Phe Pro Asn Tyr Asp Asn Arg Arg Tyr Pro Ile Gln Pro Val Gly Gln
370                 375                 380

Leu Thr Arg Glu Val Tyr Thr Asp Pro Leu Ile Asn Phe Asn Pro Gln
385                 390                 395                 400

Leu Gln Ser Val Ala Gln Leu Pro Thr Phe Asn Val Met Glu Ser Ser
                405                 410                 415

Ala Ile Arg Asn Pro His Leu Phe Asp Ile Leu Asn Asn Leu Thr Ile
                420                 425                 430

Phe Thr Asp Trp Phe Ser Val Gly Arg Asn Phe Tyr Trp Gly Gly His
            435                 440                 445

Arg Val Ile Ser Ser Leu Ile Gly Gly Gly Asn Ile Thr Ser Pro Ile
450                 455                 460

Tyr Gly Arg Glu Ala Asn Gln Glu Pro Pro Arg Ser Phe Thr Phe Asn
465                 470                 475                 480

Gly Pro Val Phe Arg Thr Leu Ser Asn Pro Thr Leu Arg Leu Leu Gln
                485                 490                 495

Gln Pro Trp Pro Ala Pro Pro Phe Asn Leu Arg Gly Val Glu Gly Val
            500                 505                 510

Glu Phe Ser Thr Pro Thr Asn Ser Phe Thr Tyr Arg Gly Arg Gly Thr
            515                 520                 525

Val Asp Ser Leu Thr Glu Leu Pro Pro Glu Asp Asn Ser Val Pro Pro
530                 535                 540

Arg Glu Gly Tyr Ser His Arg Leu Cys His Ala Thr Phe Val Gln Arg
```

-continued

```
         545                 550                 555                 560
    Ser Gly Thr Pro Phe Leu Thr Thr Gly Val Val Phe Ser Trp Thr His
                        565                 570                 575

Arg Ser Ala Thr Leu Thr Asn Thr Ile Asp Pro Glu Arg Ile Asn Gln
                    580                 585                 590

Ile Pro Leu Val Lys Gly Phe Arg Val Trp Gly Thr Ser Val Ile
                595                 600                 605

Thr Gly Pro Gly Phe Thr Gly Gly Asp Ile Leu Arg Arg Asn Thr Phe
                610                 615                 620

Gly Asp Phe Val Ser Leu Gln Val Asn Ile Asn Ser Pro Ile Thr Gln
    625                 630                 635                 640

Arg Tyr Arg Leu Arg Phe Arg Tyr Ala Ser Ser Arg Asp Ala Arg Val
                    645                 650                 655

Ile Val Leu Thr Gly Ala Ala Ser Thr Gly Val Gly Gly Gln Val Ser
                660                 665                 670

Val Asn Met Pro Leu Gln Lys Thr Met Glu Ile Gly Glu Asn Leu Thr
                675                 680                 685

Ser Arg Thr Phe Arg Tyr Thr Asp Phe Ser Asn Pro Phe Ser Phe Arg
                690                 695                 700

Ala Asn Pro Asp Ile Ile Gly Ile Ser Glu Gln Pro Leu Phe Gly Ala
    705                 710                 715                 720

Gly Ser Ile Ser Ser Gly Glu Leu Tyr Ile Asp Lys Ile Glu Ile Ile
                        725                 730                 735

Leu Ala Asp Ala Thr Phe Glu Ala Glu Ser Asp Leu Glu Arg
                740                 745                 750
```

<210> SEQ ID NO 8
<211> LENGTH: 2313
<212> TYPE: DNA
<213> ORGANISM: Artificial Sequence
<220> FEATURE:
<223> OTHER INFORMATION: Optimized cry1B1 coding sequence
<220> FEATURE:
<221> NAME/KEY: CDS
<222> LOCATION: (1)..(2310)

<400> SEQUENCE: 8

```
atg gct tct atc tct tct tct gtt gct act gtt tct aga act gct cct        48
Met Ala Ser Ile Ser Ser Ser Val Ala Thr Val Ser Arg Thr Ala Pro
1               5                   10                  15 gct cag gct aac atg gtt gct cct ttc act gga ctt aag tct aac gct        96
Ala Gln Ala Asn Met Val Ala Pro Phe Thr Gly Leu Lys Ser Asn Ala
            20                  25                  30 gct ttc cct act act aag aag gct aac gat ttc tct act ctt cct tct       144
Ala Phe Pro Thr Thr Lys Lys Ala Asn Asp Phe Ser Thr Leu Pro Ser
        35                  40                  45 aac gga gga aga gtt cag tgt atg cag gtt tgg cct gct tac gga aac       192
Asn Gly Gly Arg Val Gln Cys Met Gln Val Trp Pro Ala Tyr Gly Asn
    50                  55                  60 aag aag ttc gag act ctt tct tac ctt cct cct ctt tct atg gct cct       240
Lys Lys Phe Glu Thr Leu Ser Tyr Leu Pro Pro Leu Ser Met Ala Pro
65                  70                  75                  80 act gtt atg atg gct tct tct gct act gct gtt gct cct ttc cag gga       288
Thr Val Met Met Ala Ser Ser Ala Thr Ala Val Ala Pro Phe Gln Gly
                85                  90                  95 ctt aag tct act gct tct ctt cct gtt gct aga aga tct tct aga tct       336
Leu Lys Ser Thr Ala Ser Leu Pro Val Ala Arg Arg Ser Ser Arg Ser
            100                 105                 110
```

-continued

| | | |
|---|---|---|
| ctt gga aac gtt tct aac gga gga aga atc aga tgt act tcg aac aga<br>Leu Gly Asn Val Ser Asn Gly Gly Arg Ile Arg Cys Thr Ser Asn Arg<br>115                        120                      125 | 384 |
| aag aac gag aac gag atc atc aac gct gtt tct aac cat tct gct cag<br>Lys Asn Glu Asn Glu Ile Ile Asn Ala Val Ser Asn His Ser Ala Gln<br>130                        135                      140 | 432 |
| atg gat ctt ctt cct gat gct aga atc gag gat tct ctt tgt atc gct<br>Met Asp Leu Leu Pro Asp Ala Arg Ile Glu Asp Ser Leu Cys Ile Ala<br>145                        150                      155                      160 | 480 |
| gag gga aac aac atc gat cct ttc gtt tct gct tct act gtt cag act<br>Glu Gly Asn Asn Ile Asp Pro Phe Val Ser Ala Ser Thr Val Gln Thr<br>                      165                      170                      175 | 528 |
| ggt atc aac atc gct gga aga att ctt gga gtt ctt gga gtt cct ttc<br>Gly Ile Asn Ile Ala Gly Arg Ile Leu Gly Val Leu Gly Val Pro Phe<br>                      180                      185                      190 | 576 |
| gct gga cag ctt gct tct ttc tac tct ttc ctt gtt gga gag ctt tgg<br>Ala Gly Gln Leu Ala Ser Phe Tyr Ser Phe Leu Val Gly Glu Leu Trp<br>                195                      200                      205 | 624 |
| cct aga gga aga gat cag tgg gag atc ttc ctt gag cat gtt gag cag<br>Pro Arg Gly Arg Asp Gln Trp Glu Ile Phe Leu Glu His Val Glu Gln<br>210                        215                      220 | 672 |
| ctt atc aac cag cag atc act gag aac gct aga aac act gct ctt gct<br>Leu Ile Asn Gln Gln Ile Thr Glu Asn Ala Arg Asn Thr Ala Leu Ala<br>225                        230                      235                      240 | 720 |
| aga ctt cag gga ctt gga gat tct ttc aga gct tac cag cag tct ctt<br>Arg Leu Gln Gly Leu Gly Asp Ser Phe Arg Ala Tyr Gln Gln Ser Leu<br>                      245                      250                      255 | 768 |
| gag gac tgg ctt gag aac aga gat gat gct aga act aga tct gtt ctt<br>Glu Asp Trp Leu Glu Asn Arg Asp Asp Ala Arg Thr Arg Ser Val Leu<br>                      260                      265                      270 | 816 |
| cat act cag tac atc gct ctt gag ctt gat ttc ctt aac gct atg cct<br>His Thr Gln Tyr Ile Ala Leu Glu Leu Asp Phe Leu Asn Ala Met Pro<br>                275                      280                      285 | 864 |
| ctt ttc gct atc aga aac cag gag gtt cct ctt ctt atg gtt tac gct<br>Leu Phe Ala Ile Arg Asn Gln Glu Val Pro Leu Leu Met Val Tyr Ala<br>          290                      295                      300 | 912 |
| cag gct gct aac ctt cat ctt ctt ctt ctt aga gat gct tct ctt ttc<br>Gln Ala Ala Asn Leu His Leu Leu Leu Leu Arg Asp Ala Ser Leu Phe<br>305                        310                      315                      320 | 960 |
| gga tct gag ttc gga ctt act tct cag gag atc cag aga tat tac gag<br>Gly Ser Glu Phe Gly Leu Thr Ser Gln Glu Ile Gln Arg Tyr Tyr Glu<br>                      325                      330                      335 | 1008 |
| aga cag gtt gag aga act aga gat tac tct gat tac tgt gtt gag tgg<br>Arg Gln Val Glu Arg Thr Arg Asp Tyr Ser Asp Tyr Cys Val Glu Trp<br>          340                      345                      350 | 1056 |
| tac aac act gga ctt aac tct ctt aga gga act aac gct gct tct tgg<br>Tyr Asn Thr Gly Leu Asn Ser Leu Arg Gly Thr Asn Ala Ala Ser Trp<br>355                        360                      365 | 1104 |
| gtt aga tac aac cag ttc aga aga gat ctt act ctt gga gtt ctt gat<br>Val Arg Tyr Asn Gln Phe Arg Arg Asp Leu Thr Leu Gly Val Leu Asp<br>370                        375                      380 | 1152 |
| ctt gtt gct ctt ttc cct tct tac gac act aga act tac cct atc aac<br>Leu Val Ala Leu Phe Pro Ser Tyr Asp Thr Arg Thr Tyr Pro Ile Asn<br>385                        390                      395                      400 | 1200 |
| act tct gct cag ctt act aga gag gtt tac act gat gct atc gga gct<br>Thr Ser Ala Gln Leu Thr Arg Glu Val Tyr Thr Asp Ala Ile Gly Ala<br>                          405                      410                      415 | 1248 |
| act gga gtt aac atg gct tct atg aac tgg tac aac aac aac gct cct<br>Thr Gly Val Asn Met Ala Ser Met Asn Trp Tyr Asn Asn Asn Ala Pro<br>          420                      425                      430 | 1296 |

```
tct ttc tct gct atc gag gct gct gct atc aga tct cct cat ctt ctt    1344
Ser Phe Ser Ala Ile Glu Ala Ala Ala Ile Arg Ser Pro His Leu Leu
            435                 440                 445 gat ttc ctt gag cag ctt act atc ttc tct gct tct tct aga tgg tct    1392
Asp Phe Leu Glu Gln Leu Thr Ile Phe Ser Ala Ser Ser Arg Trp Ser
    450                 455                 460 aac act aga cac atg act tac tgg aga gga cat acc atc cag tct aga    1440
Asn Thr Arg His Met Thr Tyr Trp Arg Gly His Thr Ile Gln Ser Arg
465                 470                 475                 480 cct atc gga gga gga ctt aac act tct act cat gga gct act aac act    1488
Pro Ile Gly Gly Gly Leu Asn Thr Ser Thr His Gly Ala Thr Asn Thr
                485                 490                 495 tct atc aac cct gtt act ctt aga ttc gct tct aga gat gtt tac aga    1536
Ser Ile Asn Pro Val Thr Leu Arg Phe Ala Ser Arg Asp Val Tyr Arg
            500                 505                 510 act gag tct tac gct gga gtt ctt ctt tgg gga atc tac ctt gag cct    1584
Thr Glu Ser Tyr Ala Gly Val Leu Leu Trp Gly Ile Tyr Leu Glu Pro
        515                 520                 525 atc cac gga gtt cct act gtt aga ttc aac ttc act aac cct cag aac    1632
Ile His Gly Val Pro Thr Val Arg Phe Asn Phe Thr Asn Pro Gln Asn
    530                 535                 540 atc tct gat aga gga act gct aac tac tct cag cct tac gag tct cct    1680
Ile Ser Asp Arg Gly Thr Ala Asn Tyr Ser Gln Pro Tyr Glu Ser Pro
545                 550                 555                 560 gga ctt cag ctt aag gat tct gag act gag ctt cct cct gag act act    1728
Gly Leu Gln Leu Lys Asp Ser Glu Thr Glu Leu Pro Pro Glu Thr Thr
                565                 570                 575 gag aga cct aac tac gag tct tac tct cat aga ctt tct cat atc gga    1776
Glu Arg Pro Asn Tyr Glu Ser Tyr Ser His Arg Leu Ser His Ile Gly
            580                 585                 590 atc atc ctt cag tct aga gtt aac gtt cct gtt tac tct tgg act cat    1824
Ile Ile Leu Gln Ser Arg Val Asn Val Pro Val Tyr Ser Trp Thr His
        595                 600                 605 aga tct gct gat aga act aac act atc gga cct aac aga atc act cag    1872
Arg Ser Ala Asp Arg Thr Asn Thr Ile Gly Pro Asn Arg Ile Thr Gln
    610                 615                 620 atc cct atg gtt aag gct tct gag ctt cct cag gga act act gtt gtt    1920
Ile Pro Met Val Lys Ala Ser Glu Leu Pro Gln Gly Thr Thr Val Val
625                 630                 635                 640 aga gga cct gga ttc act gga gga gat atc ctt aga aga act aac act    1968
Arg Gly Pro Gly Phe Thr Gly Gly Asp Ile Leu Arg Arg Thr Asn Thr
                645                 650                 655 gga gga ttc gga cct atc aga gtt act gtt aac gga cct ctt act cag    2016
Gly Gly Phe Gly Pro Ile Arg Val Thr Val Asn Gly Pro Leu Thr Gln
            660                 665                 670 aga tac aga atc gga ttc aga tac gct tct act gtt gat ttc gat ttc    2064
Arg Tyr Arg Ile Gly Phe Arg Tyr Ala Ser Thr Val Asp Phe Asp Phe
        675                 680                 685 ttc gtt tct aga gga gga act act gtt aac aac ttc aga ttc ctt aga    2112
Phe Val Ser Arg Gly Gly Thr Thr Val Asn Asn Phe Arg Phe Leu Arg
    690                 695                 700 act atg aac tct gga gat gag ctt aag tac gga aac ttc gtt aga aga    2160
Thr Met Asn Ser Gly Asp Glu Leu Lys Tyr Gly Asn Phe Val Arg Arg
705                 710                 715                 720 gct ttc act act cct ttc act ttc act cag atc cag gat atc atc aga    2208
Ala Phe Thr Thr Pro Phe Thr Phe Thr Gln Ile Gln Asp Ile Ile Arg
                725                 730                 735 act tct atc cag gga ctt tct gga aac gga gag gtt tac atc gat aaa    2256
Thr Ser Ile Gln Gly Leu Ser Gly Asn Gly Glu Val Tyr Ile Asp Lys
```

```
                              740                 745                 750
atc gag atc atc cct gtt act gct act ttc gag gct gag tac gat tta       2304
Ile Glu Ile Ile Pro Val Thr Ala Thr Phe Glu Ala Glu Tyr Asp Leu
            755                 760                 765 gag aga tga                                                           2313
Glu Arg
    770
```

<210> SEQ ID NO 9
<211> LENGTH: 770
<212> TYPE: PRT
<213> ORGANISM: Artificial Sequence
<220> FEATURE:
<223> OTHER INFORMATION: Cry1B1 protein

<400> SEQUENCE: 9

```
Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Pro Leu Ser Met Ala Pro
65              70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys Thr Ser Asn Arg
        115                 120                 125

Lys Asn Glu Asn Glu Ile Ile Asn Ala Val Ser Asn His Ser Ala Gln
    130                 135                 140

Met Asp Leu Leu Pro Asp Ala Arg Ile Glu Asp Ser Leu Cys Ile Ala
145             150                 155                 160

Glu Gly Asn Asn Ile Asp Pro Phe Val Ser Ala Ser Thr Val Gln Thr
                165                 170                 175

Gly Ile Asn Ile Ala Gly Arg Ile Leu Gly Val Leu Gly Val Pro Phe
            180                 185                 190

Ala Gly Gln Leu Ala Ser Phe Tyr Ser Phe Leu Val Gly Glu Leu Trp
        195                 200                 205

Pro Arg Gly Arg Asp Gln Trp Glu Ile Phe Leu Glu His Val Glu Gln
    210                 215                 220

Leu Ile Asn Gln Gln Ile Thr Glu Asn Ala Arg Asn Thr Ala Leu Ala
225             230                 235                 240

Arg Leu Gln Gly Leu Gly Asp Ser Phe Arg Ala Tyr Gln Gln Ser Leu
                245                 250                 255

Glu Asp Trp Leu Glu Asn Arg Asp Asp Ala Arg Thr Arg Ser Val Leu
            260                 265                 270

His Thr Gln Tyr Ile Ala Leu Glu Leu Asp Phe Leu Asn Ala Met Pro
        275                 280                 285

Leu Phe Ala Ile Arg Asn Gln Glu Val Pro Leu Leu Met Val Tyr Ala
    290                 295                 300

Gln Ala Ala Asn Leu His Leu Leu Leu Leu Arg Asp Ala Ser Leu Phe
305             310                 315                 320
```

-continued

Gly Ser Glu Phe Gly Leu Thr Ser Gln Glu Ile Gln Arg Tyr Tyr Glu
                325                 330                 335

Arg Gln Val Glu Arg Thr Arg Asp Tyr Ser Asp Tyr Cys Val Glu Trp
            340                 345                 350

Tyr Asn Thr Gly Leu Asn Ser Leu Arg Gly Thr Asn Ala Ala Ser Trp
        355                 360                 365

Val Arg Tyr Asn Gln Phe Arg Arg Asp Leu Thr Leu Gly Val Leu Asp
    370                 375                 380

Leu Val Ala Leu Phe Pro Ser Tyr Asp Thr Arg Thr Tyr Pro Ile Asn
385                 390                 395                 400

Thr Ser Ala Gln Leu Thr Arg Glu Val Tyr Thr Asp Ala Ile Gly Ala
                405                 410                 415

Thr Gly Val Asn Met Ala Ser Met Asn Trp Tyr Asn Asn Ala Pro
            420                 425                 430

Ser Phe Ser Ala Ile Glu Ala Ala Ile Arg Ser Pro His Leu Leu
        435                 440                 445

Asp Phe Leu Glu Gln Leu Thr Ile Phe Ser Ala Ser Ser Arg Trp Ser
    450                 455                 460

Asn Thr Arg His Met Thr Tyr Trp Arg Gly His Thr Ile Gln Ser Arg
465                 470                 475                 480

Pro Ile Gly Gly Gly Leu Asn Thr Ser Thr His Gly Ala Thr Asn Thr
                485                 490                 495

Ser Ile Asn Pro Val Thr Leu Arg Phe Ala Ser Arg Asp Val Tyr Arg
            500                 505                 510

Thr Glu Ser Tyr Ala Gly Val Leu Leu Trp Gly Ile Tyr Leu Glu Pro
        515                 520                 525

Ile His Gly Val Pro Thr Val Arg Phe Asn Phe Thr Asn Pro Gln Asn
    530                 535                 540

Ile Ser Asp Arg Gly Thr Ala Asn Tyr Ser Gln Pro Tyr Glu Ser Pro
545                 550                 555                 560

Gly Leu Gln Leu Lys Asp Ser Glu Thr Glu Leu Pro Pro Glu Thr Thr
                565                 570                 575

Glu Arg Pro Asn Tyr Glu Ser Tyr Ser His Arg Leu Ser His Ile Gly
            580                 585                 590

Ile Ile Leu Gln Ser Arg Val Asn Val Pro Val Tyr Ser Trp Thr His
        595                 600                 605

Arg Ser Ala Asp Arg Thr Asn Thr Ile Gly Pro Asn Arg Ile Thr Gln
    610                 615                 620

Ile Pro Met Val Lys Ala Ser Glu Leu Pro Gln Gly Thr Thr Val Val
625                 630                 635                 640

Arg Gly Pro Gly Phe Thr Gly Gly Asp Ile Leu Arg Arg Thr Asn Thr
                645                 650                 655

Gly Gly Phe Gly Pro Ile Arg Val Thr Val Asn Gly Pro Leu Thr Gln
            660                 665                 670

Arg Tyr Arg Ile Gly Phe Arg Tyr Ala Ser Thr Val Asp Phe Asp Phe
        675                 680                 685

Phe Val Ser Arg Gly Gly Thr Thr Val Asn Asn Phe Arg Phe Leu Arg
    690                 695                 700

Thr Met Asn Ser Gly Asp Glu Leu Lys Tyr Gly Asn Phe Val Arg Arg
705                 710                 715                 720

Ala Phe Thr Thr Pro Phe Thr Phe Thr Gln Ile Gln Asp Ile Ile Arg
                725                 730                 735

```
Thr Ser Ile Gln Gly Leu Ser Gly Asn Gly Glu Val Tyr Ile Asp Lys
            740                 745                 750

Ile Glu Ile Ile Pro Val Thr Ala Thr Phe Glu Ala Glu Tyr Asp Leu
            755                 760                 765

Glu Arg
    770

<210> SEQ ID NO 10
<211> LENGTH: 1947
<212> TYPE: DNA
<213> ORGANISM: Artificial Sequence
<220> FEATURE:
<223> OTHER INFORMATION: Optimized cry1B2 coding sequence
<220> FEATURE:
<221> NAME/KEY: CDS
<222> LOCATION: (1)..(1944)

<400> SEQUENCE: 10 atg gct act tcg aac aga aag aac gag aac gag atc atc aac gct gtt      48
Met Ala Thr Ser Asn Arg Lys Asn Glu Asn Glu Ile Ile Asn Ala Val
1               5                   10                  15 tct aac cat tct gct cag atg gat ctt ctt cct gat gct aga atc gag     96
Ser Asn His Ser Ala Gln Met Asp Leu Leu Pro Asp Ala Arg

```
Asp Tyr Cys Val Glu Trp Tyr Asn Thr Gly Leu Asn Ser Leu Arg Gly
225                 230                 235                 240 act aac gct gct tct tgg gtt aga tac aac cag ttc aga aga gat ctt    768
Thr Asn Ala Ala Ser Trp Val Arg Tyr Asn Gln Phe Arg Arg Asp Leu
                245                 250                 255 act ctt gga gtt ctt gat ctt gtt gct ctt ttc cct tct tac gac act    816
Thr Leu Gly Val Leu Asp Leu Val Ala Leu Phe Pro Ser Tyr Asp Thr
            260                 265                 270 aga act tac cct atc aac act tct gct cag ctt act aga gag gtt tac    864
Arg Thr Tyr Pro Ile Asn Thr Ser Ala Gln Leu Thr Arg Glu Val Tyr
        275                 280                 285 act gat gct atc gga gct act gga gtt aac atg gct tct atg aac tgg    912
Thr Asp Ala Ile Gly Ala Thr Gly Val Asn Met Ala Ser Met Asn Trp
    290                 295                 300 tac aac aac aac gct cct tct ttc tct gct atc gag gct gct gct atc    960
Tyr Asn Asn Asn Ala Pro Ser Phe Ser Ala Ile Glu Ala Ala Ala Ile
305                 310                 315                 320 aga tct cct cat ctt ctt gat ttc ctt gag cag ctt act atc ttc tct   1008
Arg Ser Pro His Leu Leu Asp Phe Leu Glu Gln Leu Thr Ile Phe Ser
                325                 330                 335 gct tct tct aga tgg tct aac act aga cac atg act tac tgg aga gga   1056
Ala Ser Ser Arg Trp Ser Asn Thr Arg His Met Thr Tyr Trp Arg Gly
            340                 345                 350 cat acc atc cag tct aga cct atc gga gga gga ctt aac act tct act   1104
His Thr Ile Gln Ser Arg Pro Ile Gly Gly Gly Leu Asn Thr Ser Thr
        355                 360                 365 cat gga gct act aac act tct atc aac cct gtt act ctt aga ttc gct   1152
His Gly Ala Thr Asn Thr Ser Ile Asn Pro Val Thr Leu Arg Phe Ala
    370                 375                 380 tct aga gat gtt tac aga act gag tct tac gct gga gtt ctt ctt tgg   1200
Ser Arg Asp Val Tyr Arg Thr Glu Ser Tyr Ala Gly Val Leu Leu Trp
385                 390                 395                 400 gga atc tac ctt gag cct atc cac gga gtt cct act gtt aga ttc aac   1248
Gly Ile Tyr Leu Glu Pro Ile His Gly Val Pro Thr Val Arg Phe Asn
                405                 410                 415 ttc act aac cct cag aac atc tct gat aga gga act gct aac tac tct   1296
Phe Thr Asn Pro Gln Asn Ile Ser Asp Arg Gly Thr Ala Asn Tyr Ser
            420                 425                 430 cag cct tac gag tct cct gga ctt cag ctt aag gat tct gag act gag   1344
Gln Pro Tyr Glu Ser Pro Gly Leu Gln Leu Lys Asp Ser Glu Thr Glu
        435                 440                 445 ctt cct cct gag act act gag aga cct aac tac gag tct tac tct cat   1392
Leu Pro Pro Glu Thr Thr Glu Arg Pro Asn Tyr Glu Ser Tyr Ser His
    450                 455                 460 aga ctt tct cat atc gga atc atc ctt cag tct aga gtt aac gtt cct   1440
Arg Leu Ser His Ile Gly Ile Ile Leu Gln Ser Arg Val Asn Val Pro
465                 470                 475                 480 gtt tac tct tgg act cat aga tct gct gat aga act aac act atc gga   1488
Val Tyr Ser Trp Thr His Arg Ser Ala Asp Arg Thr Asn Thr Ile Gly
                485                 490                 495 cct aac aga atc act cag atc cct atg gtt aag gct tct gag ctt cct   1536
Pro Asn Arg Ile Thr Gln Ile Pro Met Val Lys Ala Ser Glu Leu Pro
            500                 505                 510 cag gga act act gtt gtt aga gga cct gga ttc act gga gga gat atc   1584
Gln Gly Thr Thr Val Val Arg Gly Pro Gly Phe Thr Gly Gly Asp Ile
        515                 520                 525 ctt aga aga act aac act gga gga ttc gga cct atc aga gtt act gtt   1632
Leu Arg Arg Thr Asn Thr Gly Gly Phe Gly Pro Ile Arg Val Thr Val
    530                 535                 540
```

```
aac gga cct ctt act cag aga tac aga atc gga ttc aga tac gct tct     1680
Asn Gly Pro Leu Thr Gln Arg Tyr Arg Ile Gly Phe Arg Tyr Ala Ser
545                 550                 555                 560 act gtt gat ttc gat ttc ttc gtt tct aga gga gga act act gtt aac     1728
Thr Val Asp Phe Asp Phe Phe Val Ser Arg Gly Gly Thr Thr Val Asn
                565                 570                 575 aac ttc aga ttc ctt aga act atg aac tct gga gat gag ctt aag tac     1776
Asn Phe Arg Phe Leu Arg Thr Met Asn Ser Gly Asp Glu Leu Lys Tyr
            580                 585                 590 gga aac ttc gtt aga aga gct ttc act act cct ttc act ttc act cag     1824
Gly Asn Phe Val Arg Arg Ala Phe Thr Thr Pro Phe Thr Phe Thr Gln
        595                 600                 605 atc cag gat atc atc aga act tct atc cag gga ctt tct gga aac gga     1872
Ile Gln Asp Ile Ile Arg Thr Ser Ile Gln Gly Leu Ser Gly Asn Gly
    610                 615                 620 gag gtt tac atc gat aaa atc gag atc atc cct gtt act gct act ttc     1920
Glu Val Tyr Ile Asp Lys Ile Glu Ile Ile Pro Val Thr Ala Thr Phe
625                 630                 635                 640 gag gct gag tac gat tta gag aga tga                                 1947
Glu Ala Glu Tyr Asp Leu Glu Arg
                645

<210> SEQ ID NO 11
<211> LENGTH: 648
<212> TYPE: PRT
<213> ORGANISM: Artificial Sequence
<220> FEATURE:
<223> OTHER INFORMATION: Cry1B2 protein

<400> SEQUENCE: 11

Met Ala Thr Ser Asn Arg Lys Asn Glu Asn Glu Ile Ile Asn Ala Val
1               5                   10                  15

Ser Asn His Ser Ala Gln Met Asp Leu Leu Pro Asp Ala Arg Ile Glu
            20                  25                  30

Asp Ser Leu Cys Ile Ala Glu Gly Asn Asn Ile Asp Pro Phe Val Ser
        35                  40                  45

Ala Ser Thr Val Gln Thr Gly Ile Asn Ile Ala Gly Arg Ile Leu Gly
    50                  55                  60

Val Leu Gly Val Pro Phe Ala Gly Gln Leu Ala Ser Phe Tyr Ser Phe
65                  70                  75                  80

Leu Val Gly Glu Leu Trp Pro Arg Gly Arg Asp Gln Trp Glu Ile Phe
                85                  90                  95

Leu Glu His Val Glu Gln Leu Ile Asn Gln Gln Ile Thr Glu Asn Ala
            100                 105                 110

Arg Asn Thr Ala Leu Ala Arg Leu Gln Gly Leu Gly Asp Ser Phe Arg
        115                 120                 125

Ala Tyr Gln Gln Ser Leu Glu Asp Trp Leu Glu Asn Arg Asp Asp Ala
    130                 135                 140

Arg Thr Arg Ser Val Leu His Thr Gln Tyr Ile Ala Leu Glu Leu Asp
145                 150                 155                 160

Phe Leu Asn Ala Met Pro Leu Phe Ala Ile Arg Asn Gln Glu Val Pro
                165                 170                 175

Leu Leu Met Val Tyr Ala Gln Ala Ala Asn Leu His Leu Leu Leu Leu
            180                 185                 190

Arg Asp Ala Ser Leu Phe Gly Ser Glu Phe Gly Leu Thr Ser Gln Glu
        195                 200                 205

Ile Gln Arg Tyr Tyr Glu Arg Gln Val Glu Arg Thr Arg Asp Tyr Ser
    210                 215                 220
```

-continued

```
Asp Tyr Cys Val Glu Trp Tyr Asn Thr Gly Leu Asn Ser Leu Arg Gly
225                 230                 235                 240

Thr Asn Ala Ala Ser Trp Val Arg Tyr Asn Gln Phe Arg Arg Asp Leu
            245                 250                 255

Thr Leu Gly Val Leu Asp Leu Val Ala Leu Phe Pro Ser Tyr Asp Thr
        260                 265                 270

Arg Thr Tyr Pro Ile Asn Thr Ser Ala Gln Leu Thr Arg Glu Val Tyr
    275                 280                 285

Thr Asp Ala Ile Gly Ala Thr Gly Val Asn Met Ala Ser Met Asn Trp
290                 295                 300

Tyr Asn Asn Ala Pro Ser Phe Ser Ala Ile Glu Ala Ala Ala Ala Ile
305                 310                 315                 320

Arg Ser Pro His Leu Leu Asp Phe Leu Glu Gln Leu Thr Ile Phe Ser
            325                 330                 335

Ala Ser Ser Arg Trp Ser Asn Thr Arg His Met Thr Tyr Trp Arg Gly
        340                 345                 350

His Thr Ile Gln Ser Arg Pro Ile Gly Gly Leu Asn Thr Ser Thr
    355                 360                 365

His Gly Ala Thr Asn Thr Ser Ile Asn Pro Val Thr Leu Arg Phe Ala
370                 375                 380

Ser Arg Asp Val Tyr Arg Thr Glu Ser Tyr Ala Gly Val Leu Leu Trp
385                 390                 395                 400

Gly Ile Tyr Leu Glu Pro Ile His Gly Val Pro Thr Val Arg Phe Asn
            405                 410                 415

Phe Thr Asn Pro Gln Asn Ile Ser Asp Arg Gly Thr Ala Asn Tyr Ser
        420                 425                 430

Gln Pro Tyr Glu Ser Pro Gly Leu Gln Leu Lys Asp Ser Glu Thr Glu
    435                 440                 445

Leu Pro Pro Glu Thr Thr Glu Arg Pro Asn Tyr Glu Ser Tyr Ser His
450                 455                 460

Arg Leu Ser His Ile Gly Ile Ile Leu Gln Ser Arg Val Asn Val Pro
465                 470                 475                 480

Val Tyr Ser Trp Thr His Arg Ser Ala Asp Arg Thr Asn Thr Ile Gly
            485                 490                 495

Pro Asn Arg Ile Thr Gln Ile Pro Met Val Lys Ala Ser Glu Leu Pro
        500                 505                 510

Gln Gly Thr Thr Val Val Arg Gly Pro Gly Phe Thr Gly Gly Asp Ile
    515                 520                 525

Leu Arg Arg Thr Asn Thr Gly Gly Phe Gly Pro Ile Arg Val Thr Val
530                 535                 540

Asn Gly Pro Leu Thr Gln Arg Tyr Arg Ile Gly Phe Arg Tyr Ala Ser
545                 550                 555                 560

Thr Val Asp Phe Asp Phe Phe Val Ser Arg Gly Gly Thr Thr Val Asn
            565                 570                 575

Asn Phe Arg Phe Leu Arg Thr Met Asn Ser Gly Asp Glu Leu Lys Tyr
        580                 585                 590

Gly Asn Phe Val Arg Arg Ala Phe Thr Thr Pro Phe Thr Phe Thr Gln
    595                 600                 605

Ile Gln Asp Ile Ile Arg Thr Ser Ile Gln Gly Leu Ser Gly Asn Gly
610                 615                 620

Glu Val Tyr Ile Asp Lys Ile Glu Ile Ile Pro Val Thr Ala Thr Phe
625                 630                 635                 640
```

Glu Ala Glu Tyr Asp Leu Glu Arg
                645

<210> SEQ ID NO 12
<211> LENGTH: 2181
<212> TYPE: DNA
<213> ORGANISM: Artificial Sequence
<220> FEATURE:
<223> OTHER INFORMATION: Optimized cry1D1 coding sequence
<220> FEATURE:
<221> NAME/KEY: CDS
<222> LOCATION: (1)..(2178)

<400> SEQUENCE: 12

| atg gct tct atc tct tct gtt gct act gtt tct aga act gct cct | 48 |
|---|---|
| Met Ala Ser Ile Ser Ser Val Ala Thr Val Ser Arg Thr Ala Pro | |
| 1               5                   10                  15 | |

| gct cag gct aac atg gtt gct cct ttc act gga ctt aag tct aac gct | 96 |
|---|---|
| Ala Gln Ala Asn Met Val Ala Pro Phe Thr Gly Leu Lys Ser Asn Ala | |
|             20                  25                  30 | |

| gct ttc cct act act aag aag gct aac gat ttc tct act ctt cct tct | 144 |
|---|---|
| Ala Phe Pro Thr Thr Lys Lys Ala Asn Asp Phe Ser Thr Leu Pro Ser | |
|         35                  40                  45 | |

| aac gga gga aga gtt cag tgt atg cag gtt tgg cct gct tac gga aac | 192 |
|---|---|
| Asn Gly Gly Arg Val Gln Cys Met Gln Val Trp Pro Ala Tyr Gly Asn | |
| 50                  55                  60 | |

| aag aag ttc gag act ctt tct tac ctt cct cct ctt tct atg gct cct | 240 |
|---|---|
| Lys Lys Phe Glu Thr Leu Ser Tyr Leu Pro Pro Leu Ser Met Ala Pro | |
| 65                  70                  75                  80 | |

| act gtt atg atg gct tct tct gct act gct gtt gct cct ttc cag gga | 288 |
|---|---|
| Thr Val Met Met Ala Ser Ser Ala Thr Ala Val Ala Pro Phe Gln Gly | |
|                 85                  90                  95 | |

| ctt aag tct act gct tct ctt cct gtt gct aga aga tct tct aga tct | 336 |
|---|---|
| Leu Lys Ser Thr Ala Ser Leu Pro Val Ala Arg Arg Ser Ser Arg Ser | |
|             100                 105                 110 | |

| ctt gga aac gtt tct aac gga gga aga atc aga tgt gag atc aac aac | 384 |
|---|---|
| Leu Gly Asn Val Ser Asn Gly Gly Arg Ile Arg Cys Glu Ile Asn Asn | |
|         115                 120                 125 | |

| cag aac cag tgt gtt cct tac aac tgt ctt tct aac cct aag gag atc | 432 |
|---|---|
| Gln Asn Gln Cys Val Pro Tyr Asn Cys Leu Ser Asn Pro Lys Glu Ile | |
| 130                 135                 140 | |

| atc ctt gga gag gag aga ctt gag act gga aac act gtt gct gat atc | 480 |
|---|---|
| Ile Leu Gly Glu Glu Arg Leu Glu Thr Gly Asn Thr Val Ala Asp Ile | |
| 145                 150                 155                 160 | |

| tct ctt gga ctt atc aac ttc ctt tac tct aac ttc gtt cct gga ggt | 528 |
|---|---|
| Ser Leu Gly Leu Ile Asn Phe Leu Tyr Ser Asn Phe Val Pro Gly Gly | |
|                 165                 170                 175 | |

| gga ttc atc gtt gga ctt ctt gag ctt atc tgg gga ttc atc gga cct | 576 |
|---|---|
| Gly Phe Ile Val Gly Leu Leu Glu Leu Ile Trp Gly Phe Ile Gly Pro | |
|             180                 185                 190 | |

| tct cag tgg gat atc ttc ctt gct cag atc gag cag ctt atc tct cag | 624 |
|---|---|
| Ser Gln Trp Asp Ile Phe Leu Ala Gln Ile Glu Gln Leu Ile Ser Gln | |
|         195                 200                 205 | |

| aga atc gag gag ttc gct aga aac cag gct atc tct aga ctt gag gga | 672 |
|---|---|
| Arg Ile Glu Glu Phe Ala Arg Asn Gln Ala Ile Ser Arg Leu Glu Gly | |
| 210                 215                 220 | |

| ctt tct aat ctt tac aaa gtt tac gtt aga gct ttc tct gac tgg gag | 720 |
|---|---|
| Leu Ser Asn Leu Tyr Lys Val Tyr Val Arg Ala Phe Ser Asp Trp Glu | |
| 225                 230                 235                 240 | |

| aag gat cct act aac cct gct ctt aga gag gag atg aga atc cag ttc | 768 |
|---|---|
| Lys Asp Pro Thr Asn Pro Ala Leu Arg Glu Glu Met Arg Ile Gln Phe | |
|                 245                 250                 255 | |

```
aac gat atg aac tct gct ctt atc act gct atc cct ctt ttc aga gtt    816
Asn Asp Met Asn Ser Ala Leu Ile Thr Ala Ile Pro Leu Phe Arg Val
            260                 265                 270 cag aac tac gag gtt gct ctt ctt tct gtt tac gtt cag gct gct aac    864
Gln Asn Tyr Glu Val Ala Leu Leu Ser Val Tyr Val Gln Ala Ala Asn
            275                 280                 285 ctt cat ctt tct atc ctt aga gat gtt tct gtt ttc gga gag aga tgg    912
Leu His Leu Ser Ile Leu Arg Asp Val Ser Val Phe Gly Glu Arg Trp
        290                 295                 300 gga tac gat act gct act atc aac aac aga tac tct gat ctt act tct    960
Gly Tyr Asp Thr Ala Thr Ile Asn Asn Arg Tyr Ser Asp Leu Thr Ser
305                 310                 315                 320 ctt atc cat gtt tac act aac cat tgt gtt gat act tac aac cag gga   1008
Leu Ile His Val Tyr Thr Asn His Cys Val Asp Thr Tyr Asn Gln Gly
            325                 330                 335 ctt aga aga ctt gag gga aga ttc ctt tct gac tgg atc gtt tac aac   1056
Leu Arg Arg Leu Glu Gly Arg Phe Leu Ser Asp Trp Ile Val Tyr Asn
            340                 345                 350 aga ttc aga aga cag ctt act atc tct gtt ctt gat atc gtt gct ttc   1104
Arg Phe Arg Arg Gln Leu Thr Ile Ser Val Leu Asp Ile Val Ala Phe
            355                 360                 365 ttc cct aac tac gat atc aga act tac cct atc cag act gct act cag   1152
Phe Pro Asn Tyr Asp Ile Arg Thr Tyr Pro Ile Gln Thr Ala Thr Gln
        370                 375                 380 ctt act aga gag gtt tac ctt gat ctt cct ttc atc aac gag aac ctt   1200
Leu Thr Arg Glu Val Tyr Leu Asp Leu Pro Phe Ile Asn Glu Asn Leu
385                 390                 395                 400 tct cct gct gct tct tac cct act ttc tct gct gag tct gct atc       1248
Ser Pro Ala Ala Ser Tyr Pro Thr Phe Ser Ala Ala Glu Ser Ala Ile
            405                 410                 415 atc aga tct cct cat ctt gtt gat ttc ctt aac tct ttc act atc tac   1296
Ile Arg Ser Pro His Leu Val Asp Phe Leu Asn Ser Phe Thr Ile Tyr
            420                 425                 430 act gat tct ctt gct aga tac gct tac tgg gga gga cat ctt gtt aac   1344
Thr Asp Ser Leu Ala Arg Tyr Ala Tyr Trp Gly Gly His Leu Val Asn
        435                 440                 445 tct ttc aga act gga act aca act aac ctt atc aga tct cct ctt tac   1392
Ser Phe Arg Thr Gly Thr Thr Thr Asn Leu Ile Arg Ser Pro Leu Tyr
450                 455                 460 gga aga gag gga aac act gag aga cct gtt act atc act gct tct cct   1440
Gly Arg Glu Gly Asn Thr Glu Arg Pro Val Thr Ile Thr Ala Ser Pro
465                 470                 475                 480 tct gtt cct atc ttc aga act ctt tct tac atc act gga ctt gat aac   1488
Ser Val Pro Ile Phe Arg Thr Leu Ser Tyr Ile Thr Gly Leu Asp Asn
            485                 490                 495 tct aac cct gtt gct gga atc gag gga gtt gag ttc cag aac act atc   1536
Ser Asn Pro Val Ala Gly Ile Glu Gly Val Glu Phe Gln Asn Thr Ile
        500                 505                 510 tct aga tct atc tac aga aag tct gga cct atc gat tct ttc tct gag   1584
Ser Arg Ser Ile Tyr Arg Lys Ser Gly Pro Ile Asp Ser Phe Ser Glu
        515                 520                 525 ctt cct cct cag gat gct tct gtt tct cct gct atc gga tac tct cat   1632
Leu Pro Pro Gln Asp Ala Ser Val Ser Pro Ala Ile Gly Tyr Ser His
        530                 535                 540 aga ctt tgt cat gct act ttc ctt gag aga atc tct gga cct aga atc   1680
Arg Leu Cys His Ala Thr Phe Leu Glu Arg Ile Ser Gly Pro Arg Ile
545                 550                 555                 560 gct gga act gtt ttc tct tgg act cat aga tct gct tct cct act aac   1728
Ala Gly Thr Val Phe Ser Trp Thr His Arg Ser Ala Ser Pro Thr Asn
```

```
gag gtt tct cct tct aga atc act cag atc cct tgg gtt aag gct cat      1776
Glu Val Ser Pro Ser Arg Ile Thr Gln Ile Pro Trp Val Lys Ala His
            580                 585                 590 act ctt gct tct gga gct tct gtt atc aag gga cct gga ttc act gga      1824
Thr Leu Ala Ser Gly Ala Ser Val Ile Lys Gly Pro Gly Phe Thr Gly
                595                 600                 605 gga gat atc ctt act aga aac tct atg gga gag ctt gga act ctt aga      1872
Gly Asp Ile Leu Thr Arg Asn Ser Met Gly Glu Leu Gly Thr Leu Arg
        610                 615                 620 gtt act ttc act gga aga ctt cct cag tct tac tac atc aga ttc aga      1920
Val Thr Phe Thr Gly Arg Leu Pro Gln Ser Tyr Tyr Ile Arg Phe Arg
625                 630                 635                 640 tac gct tct gtt gct aac aga tct gga act ttc aga tac tct cag cct      1968
Tyr Ala Ser Val Ala Asn Arg Ser Gly Thr Phe Arg Tyr Ser Gln Pro
                645                 650                 655 cct tct tac gga atc tct ttc cct aag act atg gat gct gga gag cct      2016
Pro Ser Tyr Gly Ile Ser Phe Pro Lys Thr Met Asp Ala Gly Glu Pro
            660                 665                 670 ctt act tct aga tct ttc gct cat aca act ctt ttc act cct atc act      2064
Leu Thr Ser Arg Ser Phe Ala His Thr Thr Leu Phe Thr Pro Ile Thr
        675                 680                 685 ttc tct aga gct cag gag gag ttc gat cta tac atc cag tct gga gtt      2112
Phe Ser Arg Ala Gln Glu Glu Phe Asp Leu Tyr Ile Gln Ser Gly Val
690                 695                 700 tac atc gat aga atc gag ttc atc cct gtt act gct act ttc gag gct      2160
Tyr Ile Asp Arg Ile Glu Phe Ile Pro Val Thr Ala Thr Phe Glu Ala
705                 710                 715                 720 gag tac gat tta gag aga tga                                          2181
Glu Tyr Asp Leu Glu Arg
                725
```

<210> SEQ ID NO 13
<211> LENGTH: 726
<212> TYPE: PRT
<213> ORGANISM: Artificial Sequence
<220> FEATURE:
<223> OTHER INFORMATION: Cry1D1 protein

<400> SEQUENCE: 13

```
Met Ala Ser Ile Ser Ser Val Ala Thr Val Ser Arg Thr Ala Pro
1               5                   10                  15

Ala Gln Ala Asn Met Val Ala Pro Phe Thr Gly Leu Lys Ser Asn Ala
            20                  25                  30

Ala Phe Pro Thr Thr Lys Lys Ala Asn Asp Phe Ser Thr Leu Pro Ser
        35                  40                  45

Asn Gly Gly Arg Val Gln Cys Met Gln Val Trp Pro Ala Tyr Gly Asn
    50                  55                  60

Lys Lys Phe Glu Thr Leu Ser Tyr Leu Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
            100                 105                 110

Leu Gly Asn Val Ser Asn Gly Gly Arg Ile Arg Cys Glu Ile Asn Asn
        115                 120                 125

Gln Asn Gln Cys Val Pro Tyr Asn Cys Leu Ser Asn Pro Lys Glu Ile
    130                 135                 140
```

-continued

Ile Leu Gly Glu Glu Arg Leu Glu Thr Gly Asn Thr Val Ala Asp Ile
145                 150                 155                 160

Ser Leu Gly Leu Ile Asn Phe Leu Tyr Ser Asn Phe Val Pro Gly Gly
            165                 170                 175

Gly Phe Ile Val Gly Leu Leu Glu Leu Ile Trp Gly Phe Ile Gly Pro
        180                 185                 190

Ser Gln Trp Asp Ile Phe Leu Ala Gln Ile Glu Gln Leu Ile Ser Gln
    195                 200                 205

Arg Ile Glu Glu Phe Ala Arg Asn Gln Ala Ile Ser Arg Leu Glu Gly
210                 215                 220

Leu Ser Asn Leu Tyr Lys Val Tyr Val Arg Ala Phe Ser Asp Trp Glu
225                 230                 235                 240

Lys Asp Pro Thr Asn Pro Ala Leu Arg Glu Glu Met Arg Ile Gln Phe
                245                 250                 255

Asn Asp Met Asn Ser Ala Leu Ile Thr Ala Ile Pro Leu Phe Arg Val
            260                 265                 270

Gln Asn Tyr Glu Val Ala Leu Leu Ser Val Tyr Val Gln Ala Ala Asn
        275                 280                 285

Leu His Leu Ser Ile Leu Arg Asp Val Ser Val Phe Gly Glu Arg Trp
    290                 295                 300

Gly Tyr Asp Thr Ala Thr Ile Asn Asn Arg Tyr Ser Asp Leu Thr Ser
305                 310                 315                 320

Leu Ile His Val Tyr Thr Asn His Cys Val Asp Thr Tyr Asn Gln Gly
                325                 330                 335

Leu Arg Arg Leu Glu Gly Arg Phe Leu Ser Asp Trp Ile Val Tyr Asn
            340                 345                 350

Arg Phe Arg Arg Gln Leu Thr Ile Ser Val Leu Asp Ile Val Ala Phe
        355                 360                 365

Phe Pro Asn Tyr Asp Ile Arg Thr Tyr Pro Ile Gln Thr Ala Thr Gln
    370                 375                 380

Leu Thr Arg Glu Val Tyr Leu Asp Leu Pro Phe Ile Asn Glu Asn Leu
385                 390                 395                 400

Ser Pro Ala Ala Ser Tyr Pro Thr Phe Ser Ala Ala Glu Ser Ala Ile
                405                 410                 415

Ile Arg Ser Pro His Leu Val Asp Phe Leu Asn Ser Phe Thr Ile Tyr
            420                 425                 430

Thr Asp Ser Leu Ala Arg Tyr Ala Tyr Trp Gly Gly His Leu Val Asn
        435                 440                 445

Ser Phe Arg Thr Gly Thr Thr Thr Asn Leu Ile Arg Ser Pro Leu Tyr
    450                 455                 460

Gly Arg Glu Gly Asn Thr Glu Arg Pro Val Thr Ile Thr Ala Ser Pro
465                 470                 475                 480

Ser Val Pro Ile Phe Arg Thr Leu Ser Tyr Ile Thr Gly Leu Asp Asn
                485                 490                 495

Ser Asn Pro Val Ala Gly Ile Glu Gly Val Glu Phe Gln Asn Thr Ile
            500                 505                 510

Ser Arg Ser Ile Tyr Arg Lys Ser Gly Pro Ile Asp Ser Phe Ser Glu
        515                 520                 525

Leu Pro Pro Gln Asp Ala Ser Val Ser Pro Ala Ile Gly Tyr Ser His
    530                 535                 540

Arg Leu Cys His Ala Thr Phe Leu Glu Arg Ile Ser Gly Pro Arg Ile
545                 550                 555                 560

Ala Gly Thr Val Phe Ser Trp Thr His Arg Ser Ala Ser Pro Thr Asn

```
                    565                 570                 575
Glu Val Ser Pro Ser Arg Ile Thr Gln Ile Pro Trp Val Lys Ala His
                580                 585                 590

Thr Leu Ala Ser Gly Ala Ser Val Ile Lys Gly Pro Gly Phe Thr Gly
            595                 600                 605

Gly Asp Ile Leu Thr Arg Asn Ser Met Gly Glu Leu Gly Thr Leu Arg
    610                 615                 620

Val Thr Phe Thr Gly Arg Leu Pro Gln Ser Tyr Tyr Ile Arg Phe Arg
625                 630                 635                 640

Tyr Ala Ser Val Ala Asn Arg Ser Gly Thr Phe Arg Tyr Ser Gln Pro
                645                 650                 655

Pro Ser Tyr Gly Ile Ser Phe Pro Lys Thr Met Asp Ala Gly Glu Pro
            660                 665                 670

Leu Thr Ser Arg Ser Phe Ala His Thr Thr Leu Phe Thr Pro Ile Thr
        675                 680                 685

Phe Ser Arg Ala Gln Glu Glu Phe Asp Leu Tyr Ile Gln Ser Gly Val
    690                 695                 700

Tyr Ile Asp Arg Ile Glu Phe Ile Pro Val Thr Ala Thr Phe Glu Ala
705                 710                 715                 720

Glu Tyr Asp Leu Glu Arg
                725

<210> SEQ ID NO 14
<211> LENGTH: 1815
<212> TYPE: DNA
<213> ORGANISM: Artificial Sequence
<220> FEATURE:
<223> OTHER INFORMATION: Optimized cry1D2 coding sequence
<220> FEATURE:
<221> NAME/KEY: CDS
<222> LOCATION: (1)..(1812)

<400> SEQUENCE: 14 atg gct gag atc aac aac cag aac cag tgt gtt cct tac aac tgt ctt      48
Met Ala Glu Ile Asn Asn Gln Asn Gln Cys Val Pro Tyr Asn Cys Leu
1               5                  10                  15 tct aac cct aag gag atc atc ctt gga gag gag aga ctt gag act gga      96
Ser Asn Pro Lys Glu Ile Ile Leu Gly Glu Glu Arg Leu Glu Thr Gly
                20                  25                  30 aac act gtt gct gat atc tct ctt gga ctt atc aac ttc ctt tac tct     144
Asn Thr Val Ala Asp Ile Ser Leu Gly Leu Ile Asn Phe Leu Tyr Ser
            35                  40                  45 aac ttc gtt cct gga ggt gga ttc atc gtt gga ctt ctt gag ctt atc     192
Asn Phe Val Pro Gly Gly Gly Phe Ile Val Gly Leu Leu Glu Leu Ile
        50                  55                  60 tgg gga ttc atc gga cct tct cag tgg gat atc ttc ctt gct cag atc     240
Trp Gly Phe Ile Gly Pro Ser Gln Trp Asp Ile Phe Leu Ala Gln Ile
65                  70                  75                  80 gag cag ctt atc tct cag aga atc gag gag ttc gct aga aac cag gct     288
Glu Gln Leu Ile Ser Gln Arg Ile Glu Glu Phe Ala Arg Asn Gln Ala
                85                  90                  95 atc tct aga ctt gag gga ctt tct aat ctt tac aaa gtt tac gtt aga     336
Ile Ser Arg Leu Glu Gly Leu Ser Asn Leu Tyr Lys Val Tyr Val Arg
            100                 105                 110 gct ttc tct gac tgg gag aag gat cct act aac cct gct ctt aga gag     384
Ala Phe Ser Asp Trp Glu Lys Asp Pro Thr Asn Pro Ala Leu Arg Glu
        115                 120                 125 gag atg aga atc cag ttc aac gat atg aac tct gct ctt atc act gct     432
Glu Met Arg Ile Gln Phe Asn Asp Met Asn Ser Ala Leu Ile Thr Ala
```

```
              130                 135                 140
atc cct ctt ttc aga gtt cag aac tac gag gtt gct ctt ctt tct gtt      480
Ile Pro Leu Phe Arg Val Gln Asn Tyr Glu Val Ala Leu Leu Ser Val
145                 150                 155                 160 tac gtt cag gct gct aac ctt cat ctt tct atc ctt aga gat gtt tct      528
Tyr Val Gln Ala Ala Asn Leu His Leu Ser Ile Leu Arg Asp Val Ser
                165                 170                 175 gtt ttc gga gag aga tgg gga tac gat act gct act atc aac aac aga      576
Val Phe Gly Glu Arg Trp Gly Tyr Asp Thr Ala Thr Ile Asn Asn Arg
            180                 185                 190 tac tct gat ctt act tct ctt atc cat gtt tac act aac cat tgt gtt      624
Tyr Ser Asp Leu Thr Ser Leu Ile His Val Tyr Thr Asn His Cys Val
        195                 200                 205 gat act tac aac cag gga ctt aga aga ctt gag gga aga ttc ctt tct      672
Asp Thr Tyr Asn Gln Gly Leu Arg Arg Leu Glu Gly Arg Phe Leu Ser
    210                 215                 220 gac tgg atc gtt tac aac aga ttc aga aga cag ctt act atc tct gtt      720
Asp Trp Ile Val Tyr Asn Arg Phe Arg Arg Gln Leu Thr Ile Ser Val
225                 230                 235                 240 ctt gat atc gtt gct ttc ttc cct aac tac gat atc aga act tac cct      768
Leu Asp Ile Val Ala Phe Phe Pro Asn Tyr Asp Ile Arg Thr Tyr Pro
                245                 250                 255 atc cag act gct act cag ctt act aga gag gtt tac ctt gat ctt cct      816
Ile Gln Thr Ala Thr Gln Leu Thr Arg Glu Val Tyr Leu Asp Leu Pro
            260                 265                 270 ttc atc aac gag aac ctt tct cct gct gct tct tac cct act ttc tct      864
Phe Ile Asn Glu Asn Leu Ser Pro Ala Ala Ser Tyr Pro Thr Phe Ser
        275                 280                 285 gct gct gag tct gct atc atc aga tct cct cat ctt gtt gat ttc ctt      912
Ala Ala Glu Ser Ala Ile Ile Arg Ser Pro His Leu Val Asp Phe Leu
    290                 295                 300 aac tct ttc act atc tac act gat tct ctt gct aga tac gct tac tgg      960
Asn Ser Phe Thr Ile Tyr Thr Asp Ser Leu Ala Arg Tyr Ala Tyr Trp
305                 310                 315                 320 gga gga cat ctt gtt aac tct ttc aga act gga act aca act aac ctt     1008
Gly Gly His Leu Val Asn Ser Phe Arg Thr Gly Thr Thr Thr Asn Leu
                325                 330                 335 atc aga tct cct ctt tac gga aga gag gga aac act gag aga cct gtt     1056
Ile Arg Ser Pro Leu Tyr Gly Arg Glu Gly Asn Thr Glu Arg Pro Val
            340                 345                 350 act atc act gct tct cct tct gtt cct atc ttc aga act ctt tct tac     1104
Thr Ile Thr Ala Ser Pro Ser Val Pro Ile Phe Arg Thr Leu Ser Tyr
        355                 360                 365 atc act gga ctt gat aac tct aac cct gtt gct gga atc gag gga gtt     1152
Ile Thr Gly Leu Asp Asn Ser Asn Pro Val Ala Gly Ile Glu Gly Val
    370                 375                 380 gag ttc cag aac act atc tct aga tct atc tac aga aag tct gga cct     1200
Glu Phe Gln Asn Thr Ile Ser Arg Ser Ile Tyr Arg Lys Ser Gly Pro
385                 390                 395                 400 atc gat tct ttc tct gag ctt cct cct cag gat gct tct gtt tct cct     1248
Ile Asp Ser Phe Ser Glu Leu Pro Pro Gln Asp Ala Ser Val Ser Pro
                405                 410                 415 gct atc gga tac tct cat aga ctt tgt cat gct act ttc ctt gag aga     1296
Ala Ile Gly Tyr Ser His Arg Leu Cys His Ala Thr Phe Leu Glu Arg
            420                 425                 430 atc tct gga cct aga atc gct gga act gtt ttc tct tgg act cat aga     1344
Ile Ser Gly Pro Arg Ile Ala Gly Thr Val Phe Ser Trp Thr His Arg
        435                 440                 445 tct gct tct cct act aac gag gtt tct cct tct aga atc act cag atc     1392
```

```
Ser Ala Ser Pro Thr Asn Glu Val Ser Pro Ser Arg Ile Thr Gln Ile
        450                 455                 460 cct tgg gtt aag gct cat act ctt gct tct gga gct tct gtt atc aag    1440
Pro Trp Val Lys Ala His Thr Leu Ala Ser Gly Ala Ser Val Ile Lys
465                 470                 475                 480 gga cct gga ttc act gga gga gat atc ctt act aga aac tct atg gga    1488
Gly Pro Gly Phe Thr Gly Gly Asp Ile Leu Thr Arg Asn Ser Met Gly
                    485                 490                 495 gag ctt gga act ctt aga gtt act ttc act gga aga ctt cct cag tct    1536
Glu Leu Gly Thr Leu Arg Val Thr Phe Thr Gly Arg Leu Pro Gln Ser
                500                 505                 510 tac tac atc aga ttc aga tac gct tct gtt gct aac aga tct gga act    1584
Tyr Tyr Ile Arg Phe Arg Tyr Ala Ser Val Ala Asn Arg Ser Gly Thr
            515                 520                 525 ttc aga tac tct cag cct cct tct tac gga atc tct ttc cct aag act    1632
Phe Arg Tyr Ser Gln Pro Pro Ser Tyr Gly Ile Ser Phe Pro Lys Thr
530                 535                 540 atg gat gct gga gag cct ctt act tct aga tct ttc gct cat aca act    1680
Met Asp Ala Gly Glu Pro Leu Thr Ser Arg Ser Phe Ala His Thr Thr
545                 550                 555                 560 ctt ttc act cct atc act ttc tct aga gct cag gag gag ttc gat cta    1728
Leu Phe Thr Pro Ile Thr Phe Ser Arg Ala Gln Glu Glu Phe Asp Leu
                565                 570                 575 tac atc cag tct gga gtt tac atc gat aga atc gag ttc atc cct gtt    1776
Tyr Ile Gln Ser Gly Val Tyr Ile Asp Arg Ile Glu Phe Ile Pro Val
                580                 585                 590 act gct act ttc gag gct gag tac gat tta gag aga tga                1815
Thr Ala Thr Phe Glu Ala Glu Tyr Asp Leu Glu Arg
            595                 600

<210> SEQ ID NO 15
<211> LENGTH: 604
<212> TYPE: PRT
<213> ORGANISM: Artificial Sequence
<220> FEATURE:
<223> OTHER INFORMATION: Cry1D2 protein

<400> SEQUENCE: 15

Met Ala Glu Ile Asn Asn Gln Asn Gln Cys Val Pro Tyr Asn Cys Leu
1               5                   10                  15

Ser Asn Pro Lys Glu Ile Ile Leu Gly Glu Glu Arg Leu Glu Thr Gly
            20                  25                  30

Asn Thr Val Ala Asp Ile Ser Leu Gly Leu Ile Asn Phe Leu Tyr Ser
        35                  40                  45

Asn Phe Val Pro Gly Gly Gly Phe Ile Val Gly Leu Leu Glu Leu Ile
    50                  55                  60

Trp Gly Phe Ile Gly Pro Ser Gln Trp Asp Ile Phe Leu Ala Gln Ile
65                  70                  75                  80

Glu Gln Leu Ile Ser Gln Arg Ile Glu Glu Phe Ala Arg Asn Gln Ala
                85                  90                  95

Ile Ser Arg Leu Glu Gly Leu Ser Asn Leu Tyr Lys Val Tyr Val Arg
            100                 105                 110

Ala Phe Ser Asp Trp Glu Lys Asp Pro Thr Asn Pro Ala Leu Arg Glu
        115                 120                 125

Glu Met Arg Ile Gln Phe Asn Asp Met Asn Ser Ala Leu Ile Thr Ala
    130                 135                 140

Ile Pro Leu Phe Arg Val Gln Asn Tyr Glu Val Ala Leu Leu Ser Val
145                 150                 155                 160
```

```
Tyr Val Gln Ala Ala Asn Leu His Leu Ser Ile Leu Arg Asp Val Ser
                165                 170                 175

Val Phe Gly Glu Arg Trp Gly Tyr Asp Thr Ala Thr Ile Asn Asn Arg
            180                 185                 190

Tyr Ser Asp Leu Thr Ser Leu Ile His Val Tyr Thr Asn His Cys Val
        195                 200                 205

Asp Thr Tyr Asn Gln Gly Leu Arg Arg Leu Glu Gly Arg Phe Leu Ser
    210                 215                 220

Asp Trp Ile Val Tyr Asn Arg Phe Arg Arg Gln Leu Thr Ile Ser Val
225                 230                 235                 240

Leu Asp Ile Val Ala Phe Phe Pro Asn Tyr Asp Ile Arg Thr Tyr Pro
                245                 250                 255

Ile Gln Thr Ala Thr Gln Leu Thr Arg Glu Val Tyr Leu Asp Leu Pro
            260                 265                 270

Phe Ile Asn Glu Asn Leu Ser Pro Ala Ala Ser Tyr Pro Thr Phe Ser
        275                 280                 285

Ala Ala Glu Ser Ala Ile Ile Arg Ser Pro His Leu Val Asp Phe Leu
    290                 295                 300

Asn Ser Phe Thr Ile Tyr Thr Asp Ser Leu Ala Arg Tyr Ala Tyr Trp
305                 310                 315                 320

Gly Gly His Leu Val Asn Ser Phe Arg Thr Gly Thr Thr Asn Leu
                325                 330                 335

Ile Arg Ser Pro Leu Tyr Gly Arg Glu Gly Asn Thr Glu Arg Pro Val
            340                 345                 350

Thr Ile Thr Ala Ser Pro Ser Val Pro Ile Phe Arg Thr Leu Ser Tyr
        355                 360                 365

Ile Thr Gly Leu Asp Asn Ser Asn Pro Val Ala Gly Ile Glu Gly Val
    370                 375                 380

Glu Phe Gln Asn Thr Ile Ser Arg Ser Ile Tyr Arg Lys Ser Gly Pro
385                 390                 395                 400

Ile Asp Ser Phe Ser Glu Leu Pro Pro Gln Asp Ala Ser Val Ser Pro
                405                 410                 415

Ala Ile Gly Tyr Ser His Arg Leu Cys His Ala Thr Phe Leu Glu Arg
            420                 425                 430

Ile Ser Gly Pro Arg Ile Ala Gly Thr Val Phe Ser Trp Thr His Arg
        435                 440                 445

Ser Ala Ser Pro Thr Asn Glu Val Ser Pro Ser Arg Ile Thr Gln Ile
    450                 455                 460

Pro Trp Val Lys Ala His Thr Leu Ala Ser Gly Ala Ser Val Ile Lys
465                 470                 475                 480

Gly Pro Gly Phe Thr Gly Gly Asp Ile Leu Thr Arg Asn Ser Met Gly
                485                 490                 495

Glu Leu Gly Thr Leu Arg Val Thr Phe Thr Gly Arg Leu Pro Gln Ser
            500                 505                 510

Tyr Tyr Ile Arg Phe Arg Tyr Ala Ser Val Ala Asn Arg Ser Gly Thr
        515                 520                 525

Phe Arg Tyr Ser Gln Pro Pro Ser Tyr Gly Ile Ser Phe Pro Lys Thr
    530                 535                 540

Met Asp Ala Gly Glu Pro Leu Thr Ser Arg Ser Phe Ala His Thr Thr
545                 550                 555                 560

Leu Phe Thr Pro Ile Thr Phe Ser Arg Ala Gln Glu Glu Phe Asp Leu
                565                 570                 575

Tyr Ile Gln Ser Gly Val Tyr Ile Asp Arg Ile Glu Phe Ile Pro Val
```

```
                 580                 585                 590
Thr Ala Thr Phe Glu Ala Glu Tyr Asp Leu Glu Arg
            595                 600

<210> SEQ ID NO 16
<211> LENGTH: 372
<212> TYPE: DNA
<213> ORGANISM: Artificial Sequence
<220> FEATURE:
<223> OTHER INFORMATION: Optimized chloroplast transit peptide
<220> FEATURE:
<221> NAME/KEY: CDS
<222> LOCATION: (1)..(372)

<400> SEQUENCE: 16 atg gct tct atc tct tct tct gtt gct act gtt tct aga act gct cct         48
Met Ala Ser Ile Ser Ser Ser Val Ala Thr Val Ser Arg Thr Ala Pro
1               5                  10                  15 gct cag gct aac atg gtt gct cct ttc act gga ctt aag tct aac gct         96
Ala Gln Ala Asn Met Val Ala Pro Phe Thr Gly Leu Lys Ser Asn Ala
                20                  25                  30 gct ttc cct act act aag aag gct aac gat ttc tct act ctt cct tct        144
Ala Phe Pro Thr Thr Lys Lys Ala Asn Asp Phe Ser Thr Leu Pro Ser
            35                  40                  45 aac gga gga aga gtt cag tgt atg cag gtt tgg cct gct tac gga aac        192
Asn Gly Gly Arg Val Gln Cys Met Gln Val Trp Pro Ala Tyr Gly Asn
        50                  55                  60 aag aag ttc gag act ctt tct tac ctt cct cct ctt tct atg gct cct        240
Lys Lys Phe Glu Thr Leu Ser Tyr Leu Pro Pro Leu Ser Met Ala Pro
65                  70                  75                  80 act gtt atg atg gct tct tct gct act gct gtt gct cct ttc cag gga        288
Thr Val Met Met Ala Ser Ser Ala Thr Ala Val Ala Pro Phe Gln Gly
                85                  90                  95 ctt aag tct act gct tct ctt cct gtt gct aga aga tct tct aga tct        336
Leu Lys Ser Thr Ala Ser Leu Pro Val Ala Arg Arg Ser Ser Arg Ser
            100                 105                 110 ctt gga aac gtt tct aac gga gga aga atc aga tgt                        372
Leu Gly Asn Val Ser Asn Gly Gly Arg Ile Arg Cys
        115                 120

<210> SEQ ID NO 17
<211> LENGTH: 124
<212> TYPE: PRT
<213> ORGANISM: Artificial Sequence
<220> FEATURE:
<223> OTHER INFORMATION: Chloropolast transit peptide

<400> SEQUENCE: 17

Met Ala Ser Ile Ser Ser Ser Val Ala Thr Val Ser Arg Thr Ala Pro
1               5                  10                  15

Ala Gln Ala Asn Met Val Ala Pro Phe Thr Gly Leu Lys Ser Asn Ala
                20                  25                  30

Ala Phe Pro Thr Thr Lys Lys Ala Asn Asp Phe Ser Thr Leu Pro Ser
            35                  40                  45

Asn Gly Gly Arg Val Gln Cys Met Gln Val Trp Pro Ala Tyr Gly Asn
        50                  55                  60

Lys Lys Phe Glu Thr Leu Ser Tyr Leu Pro Pro Leu Ser Met Ala Pro
65                  70                  75                  80

Thr Val Met Met Ala Ser Ser Ala Thr Ala Val Ala Pro Phe Gln Gly
                85                  90                  95

Leu Lys Ser Thr Ala Ser Leu Pro Val Ala Arg Arg Ser Ser Arg Ser
```

```
             100                 105                 110
Leu Gly Asn Val Ser Asn Gly Gly Arg Ile Arg Cys
        115                 120

<210> SEQ ID NO 18
<211> LENGTH: 988
<212> TYPE: DNA
<213> ORGANISM: Subterranean clover stunt virus

<400> SEQUENCE: 18
ctagataatt gttattatca ataaaagaat ttttattgtt attgtgttat ttggtaattt      60
atgcttataa gtaattctat gattaattgt gaattaataa gactaatgag gataataatt     120
gaatttgatt aaattaactc tgcgaagcca tatgtctttc acgtgagagt cacgtgatgt     180
ctccgcgaca ggctggcacg gggcttagta ttaccccgt gccgggatca gagacatttg      240
actaaatgtt gacttggaat aatagccctt ggattagatg acacgtggac gctcaggatc     300
tgtgatgcta gtgaagcgct taagctgaac gaatctgacg gaagagcgga caaacgcaca     360
tggactatgg cccactgctt tattaaagaa gtgaatgaca gctgtctttg cttcaagacg     420
aagtaaagaa tagtggaaaa cgcgttaatt gttattatca ataaaagaat ttttattgtt     480
attgtgttat ttggtaattt atgcttataa gtaattctat gattaattgt gaattaataa     540
gactaatgag gataataatt gaatttgatt aaattaactc tgcgaagcta tatgtctttc     600
acgtgagagt cacgtgatgt ctccgcgaca ggctggcacg gggcttagta ttaccccgt      660 gccgggatca gagacatttg actaaatgtt gacttggaat aatagccctt ggattagatg     720
acacgtggac gctcaggatc tgtgatgcta gtgaagcgct taagctgaac gaatctgacg     780
gaagagcgga caaacgcaca tggactatgg cccactgctt tattaaagaa gtgaatgaca     840
gctgtctttg cttcaagacg aagtaaagaa tagtggaaaa cgcgtaaaga ataagcgtac     900
tcagtacgct tcgtggcttt ataaatagtg cttcgtctta ttcttcgttg tatcatcaac     960
gaagaagtta agctttgttc tgcgtttc                                        988

<210> SEQ ID NO 19
<211> LENGTH: 1042
<212> TYPE: DNA
<213> ORGANISM: Subterranean clover stunt virus

<400> SEQUENCE: 19
taattaatag taattatgat taattatgag ataagagttg ttattaatgc ttatgaggaa      60
taaagaatga ttaatattgt ttaatttat tccgcgaagc ggtgtgttat gttttgttg       120 gagacatcac gtgactctca cgtgatgtct ccgcgacagg ctggcacggg gcttagtatt     180 accccgtgc cggatcaga gacatttgac taaatattga cttggaataa tagcccttgg      240
attagatgac acgtggacgc tcaggatctg tgatgctagt gaagcgctta agctgaacga     300
atctgacgga agagcggaca tacgcacatg gattatggcc cacatgtcta agtgtatct      360 ctttacagct atatcgatgt gacgtaagat gctttacttc gcttcgaagt aaagtaggaa     420
attgctcgct aagttattct tttctgaaag aaattaattt aattctaatt aaattaaatg     480
agtggcctgc agtaattaat agtaattatg attaattatg ataagagt tgttattaat     540 gcttatgagg aataaagaat gattaatatt gtttaatttt attccgcgaa gcggtgtgtt     600 atgttttgt tggagacatc acgtgactct cacgtgatgt ctccgcgaca ggctggcacg     660
gggcttagta ttaccccgt gccgggatca gagacatttg actaaatatt gacttggaat    720
```

```
aatagccctt ggattagatg acacgtggac gctcaggatc tgtgatgcta gtgaagcgct    780
taagctgaac gaatctgacg gaagagcgga catacgcaca tggattatgg cccacatgtc    840
taaagtgtat ctctttacag ctatatcgat gtgacgtaag atgctttact tcgcttcgaa    900
gtaaagtagg aaattgctcg ctaagttatt cttttctgaa agaaattaat ttaattctaa    960
attaaattaa atgagtggct ataaatagtg tcgatgctac ctcacatcgt attcttcttc   1020
gcatcgtctg ttctggtttt aa                                            1042

<210> SEQ ID NO 20
<211> LENGTH: 28
<212> TYPE: DNA
<213> ORGANISM: Artificial Sequence
<220> FEATURE:
<223> OTHER INFORMATION: Cry1B gene primer

<400> SEQUENCE: 20
tacttcgaac agaaagaacg agaacgag                                        28

<210> SEQ ID NO 21
<211> LENGTH: 24
<212> TYPE: DNA
<213> ORGANISM: Artificial Sequence
<220> FEATURE:
<223> OTHER INFORMATION: Cry1B gene primer

<400> SEQUENCE: 21
gtccagcgaa aggaactcca agaa                                            24

<210> SEQ ID NO 22
<211> LENGTH: 21
<212> TYPE: DNA
<213> ORGANISM: Artificial Sequence
<220> FEATURE:
<223> OTHER INFORMATION: Cry1C gene primer

<400> SEQUENCE: 22
aaccttgagg gacttggaaa c                                               21

<210> SEQ ID NO 23
<211> LENGTH: 23
<212> TYPE: DNA
<213> ORGANISM: Artificial Sequence
<220> FEATURE:
<223> OTHER INFORMATION: Cry1C gene primer

<400> SEQUENCE: 23
aagatgaggg tttctgatag cag                                             23
```